(12) United States Patent
Liu et al.

(10) Patent No.: US 12,393,115 B2
(45) Date of Patent: Aug. 19, 2025

(54) POSITIVE WORKING PHOTOSENSITIVE MATERIAL

(71) Applicant: Merck Patent GmbH, Darmstadt (DE)

(72) Inventors: Weihong Liu, Branchburg, NJ (US); PingHung Lu, Bridgewater, NJ (US); Chunwei Chen, Whitehouse Station, NJ (US)

(73) Assignee: Merck Patent GmbH, Darmstadt (DE)

( * ) Notice: Subject to any disclaimer, the term of this patent is extended or adjusted under 35 U.S.C. 154(b) by 694 days.

(21) Appl. No.: 17/265,855

(22) PCT Filed: Sep. 3, 2019

(86) PCT No.: PCT/EP2019/073430
§ 371 (c)(1),
(2) Date: Feb. 4, 2021

(87) PCT Pub. No.: WO2020/048957
PCT Pub. Date: Mar. 12, 2020

(65) Prior Publication Data
US 2022/0019141 A1 Jan. 20, 2022

Related U.S. Application Data

(60) Provisional application No. 62/727,180, filed on Sep. 5, 2018.

(51) Int. Cl.
*G03F 7/023* (2006.01)
*C25D 7/00* (2006.01)
(Continued)

(52) U.S. Cl.
CPC .............. *G03F 7/0236* (2013.01); *C25D 7/00* (2013.01); *G03F 7/0045* (2013.01);
(Continued)

(58) Field of Classification Search
None
See application file for complete search history.

(56) References Cited

U.S. PATENT DOCUMENTS

| 3,953,408 A | 4/1976 | Hosoi et al. |
| 4,073,773 A * | 2/1978 | Banucci ............. C08G 73/1028 528/211 |

(Continued)

FOREIGN PATENT DOCUMENTS

| CN | 102981368 A | 3/2013 |
| CN | 108241256 A | 7/2018 |

(Continued)

OTHER PUBLICATIONS

Office Action received for Japanese Patent Application No. 2021-511604 mailing date Apr. 26, 2023, 6 Pages (4 Pages of English Translation & 2 Pages of Official Copy).

(Continued)

*Primary Examiner* — Martin J Angebrannndt
(74) *Attorney, Agent, or Firm* — EMD Performance Materials Corp.

(57) ABSTRACT

Disclosed herein is a photosensitive composition comprising a) at least one photoacid generator; b) at least one Novolak polymer; c) at least one acrylate polymer, comprising a component having structure (I); d) at least one glycidyl hydroxy benzoic acid condensate material comprising one or more compounds having structure (II); e) at least one heterocyclic thiol compound comprising a ring structure chosen from the general structures (III), (IIIa) or (IIIb); and f) at least one solvent. Disclose herein are also the methods of using this composition to form a resist pattern and the methods of using these resist patterns to produce metal lines. Disclosed herein are also compounds and mixtures of compounds having structure (II).

19 Claims, 2 Drawing Sheets

(51) Int. Cl.
  *G03F 7/004* (2006.01)
  *G03F 7/039* (2006.01)
  *G03F 7/20* (2006.01)
  *G03F 7/32* (2006.01)
  *G03F 7/40* (2006.01)
  *G03F 7/42* (2006.01)

(52) U.S. Cl.
  CPC .......... *G03F 7/0392* (2013.01); *G03F 7/2004* (2013.01); *G03F 7/32* (2013.01); *G03F 7/40* (2013.01); *G03F 7/42* (2013.01)

(56) References Cited

U.S. PATENT DOCUMENTS

| | | | |
|---|---|---|---|
| 4,073,775 A | 2/1978 | Matsuo | |
| 4,200,729 A | 4/1980 | Calbo | |
| 4,251,665 A | 2/1981 | Calbo | |
| 4,661,569 A * | 4/1987 | Kleine | C08F 2/004 528/109 |
| 4,806,450 A | 2/1989 | Hofmann et al. | |
| 4,956,035 A | 9/1990 | Sedlak | |
| 4,999,274 A * | 3/1991 | Seio | G03F 7/0233 430/326 |
| 5,055,374 A * | 10/1991 | Seio | G03F 7/0233 430/326 |
| 5,187,019 A | 2/1993 | Calbo et al. | |
| 5,401,604 A * | 3/1995 | Otsuka | G03F 7/164 430/168 |
| 5,817,722 A | 10/1998 | Yezrielev et al. | |
| 5,968,688 A | 10/1999 | Masuda et al. | |
| 6,042,988 A | 3/2000 | Sato et al. | |
| 6,210,846 B1 | 4/2001 | Rangarajan et al. | |
| 6,358,665 B1 | 3/2002 | Pawlowski et al. | |
| 6,635,400 B2 | 10/2003 | Kato et al. | |
| 6,783,912 B2 | 8/2004 | Cameron et al. | |
| 6,824,947 B2 | 11/2004 | Ishizuka et al. | |
| 6,908,722 B2 | 6/2005 | Ebata et al. | |
| 6,919,159 B2 | 7/2005 | Matsumoto et al. | |
| 7,255,970 B2 | 8/2007 | Toukhy et al. | |
| 7,601,482 B2 | 10/2009 | Pawlowski et al. | |
| 8,841,062 B2 | 9/2014 | Liu et al. | |
| 8,906,594 B2 | 12/2014 | Chen et al. | |
| 9,012,126 B2 | 4/2015 | Liu et al. | |
| 2001/0044075 A1 | 11/2001 | Nishimura et al. | |
| 2002/0058199 A1 | 5/2002 | Zampini et al. | |
| 2002/0061464 A1 | 5/2002 | Aoai et al. | |
| 2003/0113658 A1 | 6/2003 | Ebata et al. | |
| 2003/0235782 A1 | 12/2003 | Padmanaban et al. | |
| 2004/0005513 A1 | 1/2004 | Takahashi et al. | |
| 2004/0072420 A1 * | 4/2004 | Enomoto | G03F 7/091 430/271.1 |
| 2004/0110099 A1 | 6/2004 | Kozawa et al. | |
| 2004/0142280 A1 | 7/2004 | Iwanaga et al. | |
| 2004/0229155 A1 | 11/2004 | Rahman et al. | |
| 2004/0265733 A1 | 12/2004 | Houlihan et al. | |
| 2005/0019691 A1 | 1/2005 | Tseng et al. | |
| 2005/0019705 A1 | 1/2005 | Thackeray et al. | |
| 2005/0136341 A1 | 6/2005 | Park et al. | |
| 2005/0271974 A1 | 12/2005 | Rahman et al. | |
| 2007/0015080 A1 | 1/2007 | Toukhy et al. | |
| 2007/0190465 A1 | 8/2007 | Nishikawa et al. | |
| 2007/0275320 A1 | 11/2007 | Washio et al. | |
| 2008/0076044 A1 | 3/2008 | Mizukawa et al. | |
| 2008/0090172 A1 | 4/2008 | Hatakeyama et al. | |
| 2008/0318167 A1 * | 12/2008 | Kim | C09D 131/02 524/517 |
| 2009/0053647 A1 * | 2/2009 | Enomoto | G03F 7/11 430/319 |
| 2009/0176337 A1 | 7/2009 | Kang et al. | |
| 2009/0253073 A1 * | 10/2009 | Zahn | G03F 7/0381 430/285.1 |
| 2010/0047715 A1 | 2/2010 | Washio et al. | |
| 2010/0248146 A1 | 9/2010 | Tsuchihashi et al. | |
| 2011/0081612 A1 | 4/2011 | Fujii et al. | |
| 2011/0135749 A1 | 6/2011 | Sellinger et al. | |
| 2011/0214994 A1 | 9/2011 | Utsumi et al. | |
| 2011/0269071 A1 | 11/2011 | Fujimori et al. | |
| 2012/0003437 A1 | 1/2012 | Wada et al. | |
| 2012/0004341 A1 | 1/2012 | Kim et al. | |
| 2012/0040291 A1 * | 2/2012 | Sakamoto | H01L 21/3081 525/507 |
| 2012/0141940 A1 | 6/2012 | Shimizu et al. | |
| 2013/0337381 A1 | 12/2013 | Chen et al. | |
| 2014/0154624 A1 * | 6/2014 | Liu | G03F 7/0045 430/326 |
| 2016/0336189 A1 | 11/2016 | Kori | |
| 2019/0064662 A1 * | 2/2019 | Liu | G03F 7/0236 |
| 2020/0020927 A1 | 1/2020 | Sadakane | |

FOREIGN PATENT DOCUMENTS

| | | | |
|---|---|---|---|
| EP | 0935171 A1 | 8/1999 | |
| EP | 1757987 A1 | 2/2007 | |
| GB | 1323984 A | 7/1973 | |
| GB | 1325974 A | 8/1973 | |
| GB | 1334811 A | 10/1973 | |
| GB | 2390042 A | 12/2003 | |
| GB | 2415515 A | 12/2005 | |
| GB | 2390042 B | 11/2006 | |
| JP | S51146534 | 11/1976 | |
| JP | S6114982 A | 1/1986 | |
| JP | 06317902 A * | 11/1994 | |
| JP | 8-78318 A | 3/1996 | |
| JP | 09005990 A * | 1/1997 | ............. G03F 7/022 |
| JP | 2004212907 A * | 7/2004 | |
| JP | 2005062591 A * | 3/2005 | |
| JP | 2009-001792 A | 1/2009 | |
| JP | 2009-63824 A | 3/2009 | |
| JP | 2009-514913 A | 4/2009 | |
| JP | 2016216367 A | 12/2016 | |
| JP | 2018173521 A | 11/2018 | |
| KR | 10-2008-0075100 A | 8/2008 | |
| KR | 10-2008-0114492 A | 12/2008 | |
| TW | 201738655 A | 11/2017 | |
| WO | 2005/054951 A2 | 6/2005 | |
| WO | 2007/022124 A2 | 2/2007 | |
| WO | 2007/051646 A1 | 5/2007 | |
| WO | 2007/110773 A2 | 10/2007 | |
| WO | 2011/046192 A1 | 4/2011 | |
| WO | 2013/185989 A1 | 12/2013 | |
| WO | 2017/182441 A1 | 10/2017 | |
| WO | 2018178922 A1 | 10/2018 | |
| WO | 2020/048957 A1 | 3/2020 | |

OTHER PUBLICATIONS

International Preliminary Examination Report received for PCT Application No. PCT/EP2019/073430, mailed on Mar. 18, 2021, 10 pages.

International Search Report and Written Opinion received for PCT Application No. PCT/EP2019/073430 mailed on Jan. 7, 2020, 11 pages.

International Search Report and Written Opinion received in PCT Application No. PCT/EP2013/059771 mailed on Jul. 29, 2013, 10 pages.

International Search Report and Written Opinion received in PCT Application No. PCT/EP2013/059772 mailed on Jul. 15, 2013, 9 pages.

Coenjarts,"Mechanism of Reaction and Photoacid Generation of 1,2-di(Arylsulfonyl)hydrazine PAGs: A Laser Flash Photolytic Study", American Chemical Society, Chem. Mater., vol. 13, No. 7,, 2001, pp. 2305-2312.

Dammel Ralph, "Diazonaphthoquinone-based resists", Georgia Institute of Technology, SPIE vol. TT11 Chapter 2 & 3, 1993, pp. 9-28 & pp. 29-96.

Hiroshi Ito, "Chemical Amplification Resists for Microlithography", Adv. Polym. Sci. vol. 172, 2005, pp. 37-245.

Jan et al., "Photosensitive layers containing 1,3-diaryltriazenes and phenolic resins", American Chemical Society, SciFinder, 1972, 3 pages.

(56) References Cited

OTHER PUBLICATIONS

Pawloski et al., "Evaluation Of The Standard Addition Method To Determine Rate Constant For Acid Generation In Chemically Amplified Photoresist At 157nm", Advances in Resist Technology and Processing XVIII, Francis M. Houlihan, Editor, Proceedings of SPIE vol. 4345, 2001, pp. 1056-1065.

Reichmanis et al., "Chemical Amplification Mechanisms for Microlithography", Chem. Mater., vol. 3, No. 3, 1991, pp. 394-407.

Shirai et al., "i-Line Sensitive Photoacid Generators For UV Curing", Progress in Organic Coatings vol. 64 No. 2, Feb. 2009, pp. 175-181.

Solomon et al., "Electrochemically Deposited Solder Bumps For Wafer-level Packaging", Solid State Technology vol. 44 Issue 4, Apr. 2001, pp. 84-88.

Yoen Larry C. , "The Plating Forecast and Assurance Hardcover", Larry King Corporation, Jan. 1, 2004, pp. 5-56.

Office Action received for Chinese Patent Application No. 201980057768.3 mailing date Feb. 20, 2024, 14 Pages (7 Pages of English Translation & 7 Pages of Official Copy).

Office Action received for Korean Patent Application No. 10-2021-7009789 mailing date May 1, 2024, 24 Pages (12 Pages of English translation and 12 Pages of official copy).

Office Action received for Japanese Patent Application No. 2023-113648 mailing date Apr. 14, 2024, 8 Pages (6 Pages of English Translation and 2 Pages of Official copy).

E. Reichmanis et al_Chemical Amplification Mechanisms for Microlithography_Chern. Mater., vol. 3, No. 3, 1991_394.

Oskar Nuyken et al_Sulfur-containing azoinitiators and their properties_ Makromol, Chem. 190, 1015-1024 (1989).

Lee et al., "High-speed electrodeposition for Cu pillar fabrication and Cu pillar adhesion to an Ajinomoto build-up film (ABF)", Materials & Design, 206, May 13, 2021, pp. 109830-109840.

\* cited by examiner

POSITIVE WORKING PHOTOSENSITIVE MATERIAL

This application is a national stage application, filed under 35 U.S.C. § 371, of International Patent Application No. PCT/EP2019/073430 (filed on Sep. 3, 2019), which claims the benefit of U.S. Provisional Patent Application No. 62/727,180, filed Sep. 5, 2018, each of which applications is incorporated herein by reference in their entirety.

FIELD OF THE INVENTION

The present application for patent is in the field of photoresist imaging. More specifically, the present application for patent discloses and claims a positive working photosensitive material and additive therein which may, without limitation, be useful on copper, chalcophile, silicon, or reflective substrates.

BACKGROUND

Photoresist compositions are used in microlithography processes for making miniaturized electronic components such as in the fabrication of integrated circuit devices. Generally, in these processes, a coated film of a photoresist composition is applied to a substrate such as silicon wafers used for making integrated circuits, circuit boards and flat panel display substrates. The coated substrate is then baked to evaporate any solvent in the photoresist composition and to fix the coating onto the substrate. The baked coated surface of the substrate is next subjected to an image-wise exposure to actinic radiation.

This actinic radiation exposure causes a chemical transformation in the exposed areas of the coated surface. Visible light, ultraviolet (UV) light, extreme ultraviolet (EUV), electron beam and X-ray radiant energy are radiation types commonly used today in microlithographic processes. After this image-wise exposure, the coated substrate is treated with a developer solution to dissolve and remove either the radiation-exposed areas (for positive-type photoresists) or the unexposed areas (for negative-type photoresists) of the coated surface of the substrate.

After this development operation, the now partially unprotected substrate may be treated with a substrate-etchant solution, plasma gases or reactive ions, or have metal or metal composites deposited by sputtering or chemical vapor deposition or metal electroplated in the spaces of the substrate where the photoresist coating was removed during development. The areas of the substrate where the photoresist coating still remains are protected. Later, the remaining areas of the photoresist coating may be removed during a stripping operation, leaving a patterned substrate surface. In some instances, it is desirable to heat treat the remaining photoresist layer, after the development step and before the etching step, to increase its adhesion to the underlying substrate.

In the manufacture of patterned structures, such as wafer level packaging, displays, light emitting diode applications or microelectromechanical systems, electrochemical deposition of electrical interconnects has been used as the interconnect density increases. For example, see Solomon, Electrochemically Deposited Solder Bumps for Wafer-Level Packaging, Packaging/Assembly, Solid State Technology, pages 84-88, April 2001. Gold bumps, copper or other metal posts and copper traces for redistribution in wafer level packaging require a photoresist mold that can later be electroplated to form the final metal structures in advanced interconnect technologies. The photoresist layers are very thick compared to the photoresists used in the IC manufacturing of critical layers. Both feature size and photoresist thickness are typically in the range of 2 µm to 100 µm, (micrometers) so that high aspect ratios (photoresist thickness to line size) have to be patterned in the photoresist.

Positive-acting photoresists comprising Novolak polymers and quinone-diazide compounds as photoactive compounds are well known in the art. Novolak polymers may also be reacted with quinone diazides and combined with a polymer. It has been found that photoresists based on only Novolak/diazide do not have the photosensitivity or the steepness of sidewalls necessary for certain type of processes, especially for very thick films. Moreover, a high dark-film loss in the developer is often observed.

Known chemically amplified photoresists, such as those based on blocked poly-4-hydroxystyrene (PHOST), blocked copolymers comprising hydroxystyrene and a blocked (meth)acrylic acid repeat unit such as tert-butyl (meth)acrylate, or (meth)acrylic materials comprising alicyclic groups, acid cleavable groups, and dissolution modifying groups such as anhydrides or lactones may exhibit the required photosensitivity and even have additives to compensate for substrate reflectivity issues, acid diffusion issues, or dark film, but may unfortunately also exhibit adhesion failure, during subsequent certain unit operations such as electroplating or etching. In particular, for instance, during electroplating of metallic lines using patterned films of such resists, as a mask barrier, even resists that otherwise produce smooth lines at the substrate interphase, have a tendency to produce metallic line features that undergo adhesion loss either during or after the metal electroplating process. Also, it is important to have metallic lines electroplated which have a large contact area with the substrate to avoid electrical conductivity and thermal conductivity issues which arise when such electroplated lines have a narrow contact area with the substrate.

Therefore, there remains a need for a positive photoresist material that produce patterned photoresist film which may be used to form metallic lines with good adhesion during metal electroplating operations, and have high photosensitivity, even in thick film applications, even on reflective substrates, have process worthy development times, have low dark film loss in developers and basic electroplating solutions, and withstand wet electroplating and etching operations to produce features that can enable electroplating of metallic lines without loss of adhesion of these lines that also can enable electroplating of metal lines which maintain a large contact area with the substrate, thus avoiding conductivity and thermal issues which arise from a narrow contact area in metallic lines. The present disclosure and the accompanying claims address these needs.

SUMMARY OF THE INVENTION

The invention pertains to a positive working photosensitive composition comprising:
 a) at least one photoacid generator;
 b) at least one Novolak polymer;
 c) at least one acrylate polymer, comprising a component having structure (I),

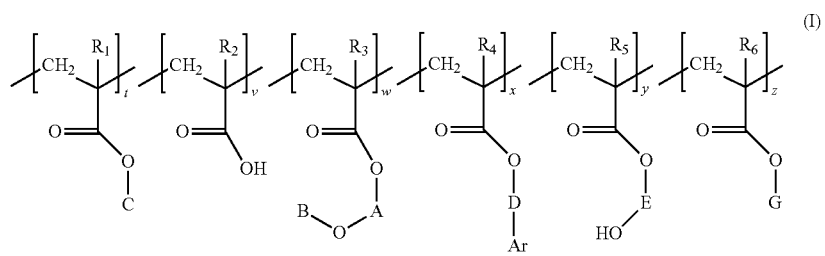

wherein $R_1$ to $R_6$ are, independently, —H, or —CH$_3$, A is a linear or branched $C_2$ to $C_{10}$ alkylene group, B is a $C_1$ to $C_{12}$ primary or secondary unsubstituted linear, branched, cyclic or alicyclic alkyl group, C is a $C_1$ to $C_{12}$ primary or secondary unsubstituted linear, branched, cyclic or alicyclic alkyl group, D is a linking group that is a direct valence bond, or a linear or branched $C_1$ to $C_{10}$, preferably $C_2$ to $C_{10}$ alkylene group, Ar is a substituted or unsubstituted aromatic group or heteroaromatic group, E is a linear or branched $C_2$ to $C_{10}$ alkylene group, G is an acid cleavable group, t is 0 mole % to about 40 mole %, v is 0 mole % to about 15 mole %, w is 0 mole % to about 45 mole %, x is 0 mole % to about 80 mole %, y is about 20 mole % to about 50 mole % and z is about 20 mole % to about 50 mole %, and further wherein the sum of t, v, w, x, y and z equals 100 mole %;

d) at least one glycidyl hydroxy benzoic acid condensate material comprising one or more compounds having structure (II),

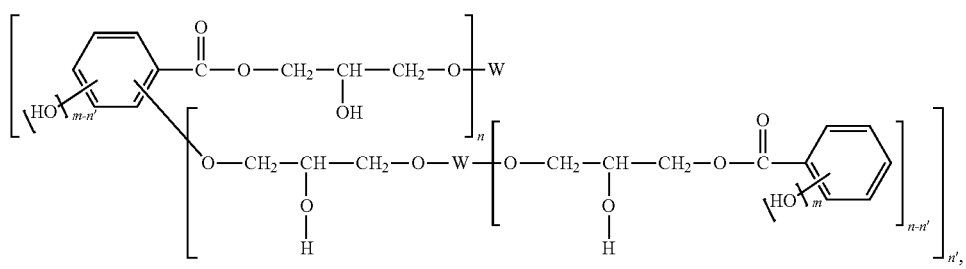

wherein,

W is an organic moiety having a molecular weight of 600 or less, wherein W forms an ether bond with the oxygen to which it is bound, m is an integer from 1 to 3 and n is an integer from 1 to 4, and further provided that when m is 1, n is 3 or 4, and when m is 2 or 3, n is an integer from 1 to 4, n' is 0 or 1, e) at least one heterocyclic thiol compound comprising a ring structure chosen from the general structures (III), (IIIa) or (IIIb), or tautomers thereof; and

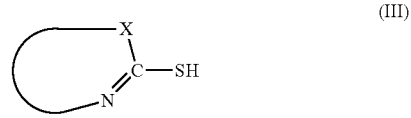

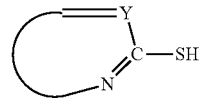

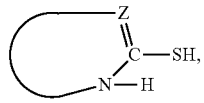

wherein, said ring structure is a single ring structure having from 4 to 8 atoms, or a multi ring structure having from 5 to 20 atoms; and wherein the single ring structure, or the multi ring structure comprises an aromatic, non-aromatic, or heteroaromatic ring, and in said structure (III), X is selected from the group consisting of $C(Rt_1)(Rt_2)$, O, S, Se, and Te;

in said structure (IIIa), Y is selected from the group consisting of $C(Rt_3)$ and N;

in said structure (IIIb), Z is selected from the group consisting of $C(Rt_3)$ and N; and $Rt_1$, $Rt_2$, and $Rt_3$ are independently selected from the group consisting of H, a substituted alkyl group having 1 to 8 carbon atoms, an unsubstituted alkyl group having 1 to 8 carbon atoms, a substituted alkenyl group having 2 to 8 carbon atoms, unsubstituted alkenyl group having 2 to 8 carbon atoms, a substituted alkynyl group having 2 to 8 carbon atoms, unsubstituted alkynyl group having 2 to 8 carbon atoms, a substituted aromatic group having 6 to 20 carbon atoms, a substituted heteroaromatic group having 3 to 20 carbon atoms, unsubstituted aromatic group having 6 to 20 carbon atoms and unsubstituted heteroaromatic group having 3 to 20 carbon atoms;

f) at least one solvent.

The invention also pertains to the method of applying the positive working photosensitive composition described herein to a substrate; image-wise exposing the photosensitive layer to actinic radiation to form a latent image; baking this latent image and developing the baked latent image in a developer.

The invention also pertains to compounds having at least one glycidyl hydroxy benzoic acid condensate material comprising one or more compounds having structure (II),

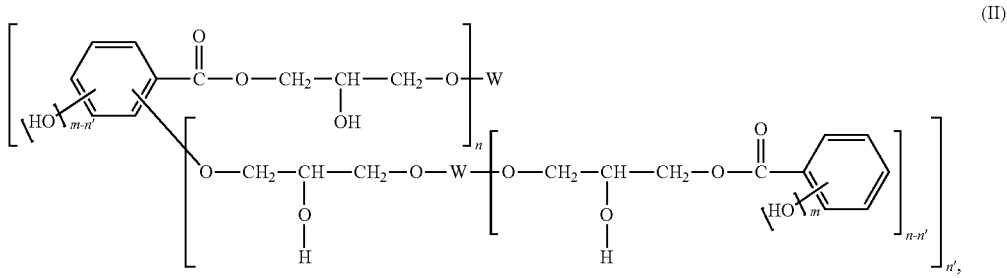

(II)

wherein,
W is an organic moiety having a molecular weight of 600 or less, wherein W forms an ether bond with the oxygen to which it is bound,
m is an integer from 1 to 3 and
n is an integer from 1 to 4, and further provided that when m is 1, n is 3 or 4,
and when m is 2 or 3, n is an integer from 1 to 4,
n' is 0 or 1.

DETAILED DESCRIPTION

Figure 1:
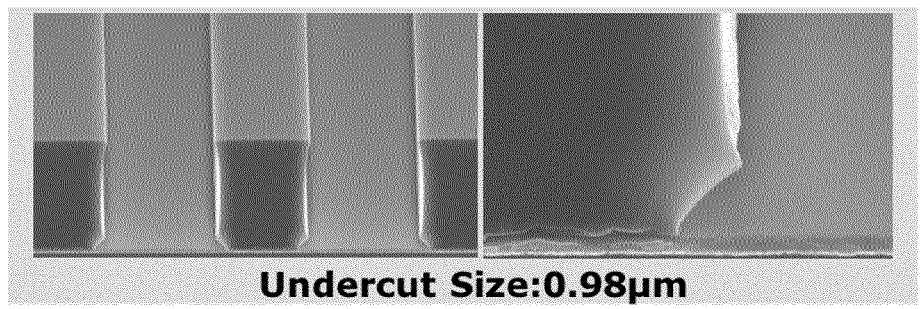
FIG. 1 Photoresist with undercut profile.

As used herein, the conjunction "or" is not intended to be exclusive unless otherwise indicated or required by the context. For example, the phrase "or, alternatively" is intended to be exclusive. As a further example, "or" may be exclusive when describing chemical substitution at a specific site.

As used herein, the term "chalcophile" is an element that has an affinity for the chalcogen elements, sulfur, selenium and tellurium. Other than the chalcogens themselves, these elements may include copper, zinc, gallium, germanium, arsenic, silver, cadmium, lanthanum, tin, antimony, gold, mercury, thallium, lead, and bismuth. Without limitation, these elements may form bonds with one or more of the chalcogen elements that are primarily covalent in character. A chalcophile substrate comprises one or more of the above listed chalcophiles.

As used herein, it is understood that a repeat unit within a polymer may be referred to by its corresponding monomer. For example, acrylate monomer (1) corresponds to its polymer repeat unit (2).

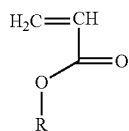

(1)

-continued

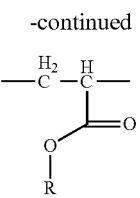

(2)

As used herein, the designation "(meth)acrylate repeat unit" may refer to an acrylate repeat unit or, alternatively, a methacrylate repeat unit. Accordingly, "acrylic acid" and "methacrylic acid" are collectively referred to as "(meth) acrylic acid", an "acrylic acid derivative" and a "methacrylic acid derivative" are collectively referred to as a "(meth) acrylic acid derivative", and "acrylate" and "methacrylate" are collectively referred to as "(meth)acrylate".

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms such as "includes" and "included", is not limiting. Also, terms such as "element" or "component" encompass both elements and components comprising one unit and elements or components that comprise more than one unit, unless specifically stated otherwise. As used herein, the conjunction "and" is intended to be inclusive and the conjunction "or" is not intended to be exclusive unless otherwise indicated. For example, the phrase "or, alternatively" is intended to be exclusive. As used herein, the term "and/or" refers to any combination of the foregoing elements including using a single element.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Herein, unless otherwise indicated, alkyl refers to hydrocarbon groups which can be linear, branched (e.g. methyl, ethyl, propyl, isopropyl, tert-butyl and the like) or cyclic (e.g. cyclohexyl, cyclopropyl, cyclopentyl and the like) multicyclic (e.g. norbornyl, adamantyl and the like). These alkyl moieties may be substituted or unsubstituted as described below. The term alkyl refers to such moieties with C-1 to C-20 carbons. It is understood that for structural reasons linear alkyls start with C-1, while branched alkyls and linear start with C-3 and multicyclic alkyls start with C-5. Moreover, it is further understood that moieties derived from alkyls described below such as alkyloxy, haloalkyloxy have the same carbon number ranges unless otherwise indicated. If the length of the alkyl group is specified as other than described above, the above described definition of alkyl still stands with respect to it encompassing all types of alkyl moieties as described above and that the structural consideration with regards to minimum number of carbon for a given type of alkyl group still apply.

Alkyloxy (a.k.a. Alkoxy) refers to an alkyl group as defined above on which is attached through an oxy (—O—) moiety (e.g. methoxy, ethoxy, propoxy, butoxy, 1,2-isopropoxy, cyclopentyloxy, cyclohexyloxy and the like). These alkyloxy moieties may be substituted or unsubstituted as described below.

Halo or halide refers to a halogen, F, Cl, Br, I which is linked by one bond to an organic moiety.

Haloalkyl refers to a linear, cyclic or branched saturated alkyl group such as defined above in which at least one of the hydrogens has been replaced by a halide selected from the group consisting of F, Cl, Br, I or mixture of these if more than one halo moiety is present. Fluoroalkyls are a specific subgroup of these moieties.

Fluoroalkyl refers to a linear, cyclic or branched saturated alkyl group as defined above in which the hydrogens have been replaced by fluorine either partially or fully (e.g. trifluoromethyl, perfluoroethyl, 2,2,2-trifluoroethyl, perfluoroisopropyl, perfluorocyclohexyl and the like). These fluoroalkyl moieties, if not perfluorinated, may be substituted or unsubstituted as described below.

Fluoroalkoxy refers to a fluoroalkyl group as defined above on which is attached through an oxy (—O—) moiety it may be completed fluorinated (a.k.a. perfluorinated) or alternatively partially fluorinated (e.g. trifluoromethoxy, perfluoroethoxy, 2,2,2-trifluoroethoxy, perfluorocyclohexyloxy and the like). These fluoroalkyl moieties, if not perfluorinated may, be substituted or unsubstituted as described below.

Herein when referring to an alkyl, alkyloxy, fluoroalkyl, fluoroalkoxy moieties with a possible range of carbon atoms which starts with C-1 such as for instance "C-1 to C-20 alkyl," or "C-1 to C-20 fluoroalkyl," as non-limiting examples, this range encompasses linear alkyls, alkyloxy, fluoroalkyl and fluoroalkoxy starting with C-1 but only designated branched alkyls, branched alkyloxy, cycloalkyl, cycloalkyloxy, branched fluoroalkyl, and cyclic fluoroalkyl starting with C-3.

Herein the term alkylene refers to hydrocarbon groups which can be a linear, branched or cyclic which has two or more attachment points (e.g. of two attachment points: methylene, ethylene, 1,2-isopropylene, a 1,4-cyclohexylene and the like; of three attachment points 1,1,1-substituted methane,1,1,2-substituted ethane, 1,2,4-substituted cyclohexane and the like). Here again, when designating a possible range of carbons, such as C-1 to C-20, as a non-limiting example, this range encompasses linear alkylenes starting with C-1 but only designates branched alkylenes, or cycloalkylene starting with C-3. These alkylene moieties may be substituted or unsubstituted as described below.

The term mono and oligomeric alkyleneoxyalkylene encompasses both simple alkyleneoxyalkylene moiety such as ethyleneoxyethylene (—CH$_2$—CH$_2$—O—CH$_2$—CH$_2$—), propyleneoxypropylene (—CH$_2$—CH$_2$—CH$_2$—O—CH$_2$—CH$_2$—CH$_2$—), and the like, and also oligomeric materials such as tri(ethyleneoxyethylene) (—CH$_2$—CH$_2$—O—CH$_2$—CH$_2$—O—CH$_2$—CH$_2$—), tri(propyleneoxypropylen), (—CH$_2$—CH$_2$—CH$_2$—O—CH$_2$—CH$_2$—CH$_2$—O—CH$_2$—CH$_2$—CH$_2$—), and the like.

Herein the term Aryl or aromatic groups refers to such groups which contain 6 to 24 carbon atoms including phenyl, tolyl, xylyl, naphthyl, anthracyl, biphenyls, bisphenyls, tris-phenyls and the like. These aryl groups may further be substituted with any of the appropriate substituents e.g. alkyl, alkoxy, acyl or aryl groups mentioned hereinabove.

The term Novolak if used herein without any other modifier of structure, refers to Novolak resins which are soluble in aqueous bases such as tetramethylammonium hydroxide and the like.

Herein the term arylene refers to a aromatic hydrocarbon moiety which has two or more attachment points (e.g. 2-5), this moiety may be a single benzene moiety (e.g. two attachment points 1,4-phenylene, 1,3-phenylene and 1,2-phenylene; three attachment points 1,2,4-substituted benzene, 1,3,5-substituted benzene and the like), a polycyclic aromatic moiety with two attachment points such derived from naphthalene, anthracene, pyrene and the like, or a multiple benzene rings in a chain which have two attachment point (e.g. biphenylene). In those instance, where the aromatic moiety is a fused aromatic ring, these may be called fused ring arylenes, and more specifically named, for instance, naphthacenylene, anthracenylene, pyrenylene, and the like. Fused ring arylenes may be substituted or unsubstituted as described below, additionally these fused ring arylenes may also contain a hydrocarbon substituent which has two attachment sites on the fused ring forming an additional aliphatic or unsaturated ring forming by attachment to the fused ring a ring having 5-10 carbon atoms.

Herein, the term "PAG," unless otherwise described, refers to a photoacid generator that can generate acid (a.k.a. photoacid) under deep UV or UV irradiation such as 200-300 nm, i-line, h-line, g-line and/or broadband irradiation. The acid may be a sulfonic acid, HCl, HBr, HAsF$_6$, and the like.

Herein, the term PAC, refers to a diazonaphthoquinone component wherein this moiety is further substituted with a sulfonyl moiety (—SO$_2$—) is attached to a phenolic compound through a sulfonate ester (—SO$_2$—O—) bond. The phenolic compound forming this sulfonate ester bond may be a phenolic compound substituted with more than one phenolic OH moiety, and consequently, the PAC may be such a phenolic compound wherein more than one of the phenol OH form this sulfonate bond. Non-limiting examples of these free PAC materials are described in "Diazonaphthoquinone-based Resist, Ralph Dammel, SPIE, Optical Engineering Press, Volume TT 11, Chapters 2 and 3.

Herein the term fused aromatic ring refers to a carbon based polycyclic aromatic compound comprising 2-8 carbon based aromatic rings fused together (e.g. naphthalene, anthracene, and the like) these fused aromatic ring which may have a single attachment point to an organic moiety as part of an aryl moiety such as a pendant fused aromatic ring aryl group on a photoacid generator (PAG) or have two attachment points as part of an arylene moiety, such as, for instance, a spacer in a substituent attached to a PAG. In PAG's, such substituents, along with other substituents that can interact by resonance delocalization, impart greater absorbance at 365 nm and/or broadband radiation and are more effective at these wavelengths.

Herein the term "arene," encompasses aromatic hydrocarbon moieties comprising 1 ring or 2-8 carbon based aromatic rings fused together.

Unless otherwise indicated in the text, the term "substituted" when referring to an aryl, alkyl, alkyloxy, fluoroalkyl, fluoroalkoxy, fused aromatic ring, arene, refers to one of these moieties which also contain one or more substituents, selected from the group consisting of unsubstituted alkyl, substituted alkyl, unsubstituted aryl, alkoxyaryl (alkyl-O-aryl-), dialkoxyaryl ((alkyl-O—)$_2$-aryl), haloaryl, alkyloxy, alkylaryl, haloalkyl, halide, hydroxyl, cyano, nitro, acetyl, alkylcarbonyl, formyl, ethenyl (CH$_2$=CH—), phenylethenyl (Ph-CH=CH—), arylethynyl (Aryl-CH=CH—), and substituents comprising ethenylenearylene moieties (e.g. Ar(—CH=CH—Ar—)$_z$ where z is 1-3. Specific, non-limiting examples of substituted aryl and substituted aryl ethenyl substituent are as follows, wherein ⌇⌇⌇ represents the point of attachment in structures (3), (4) and (5):

Otherwise, substituted aryl, and substituted ethenyls, where the substituent is selected from any of the above substituents. Similarly, the term "unsubstituted" refers to these same moieties, wherein no substituents apart from hydrogen is present.

The term "quencher" refers to a single basic component or an assembly of basic components, such as amines, or tetraalkylammonium carboxylate salts which in a resist formulation could act to capture an acid generated by a photoacid generator during exposure to i-line or broadband radiation.

The term bis[tetraalkylammonium], and tetraalkylammonium as used herein encompasses moieties in which different kinds of alkyl groups may be present as defined above, also it also encompasses moieties in which one or more of the alkyl groups is an alkyl with an aryl substituent such as benzyl (—CH$_2$-Ph), 2-phenylethyl (—CH$_2$—CH$_2$-Ph) and the like.

The term "solid components," refers to components in a photoresist formulation which are not the solvent. Such components may be solids or liquids.

It is understood that in the heterocyclic thiol compounds described herein the thiol form of these represents one of potentially several tautomeric forms. For example, without limitation, (6) may occur as its prototropic tautomer (7), whether in equilibrium or disequilibriated.

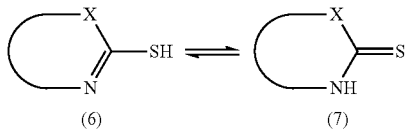

Moreover, interaction with a surface such as a chalcophilic surface or other components in solution may influence the relative concentrations of the ring structures, 3 and 4, and their respective tautomers. Accordingly, it is understood that prototropic tautomers (including annular tautomers) and valence tautomers may be referred to interchangeably by naming any of their tautomeric forms.

The inventive composition pertains to a positive working photosensitive composition comprising:

a) at least one photoacid generator;
b) at least one Novolak polymer;
c) at least one acrylate polymer, comprising a component having structure (I),

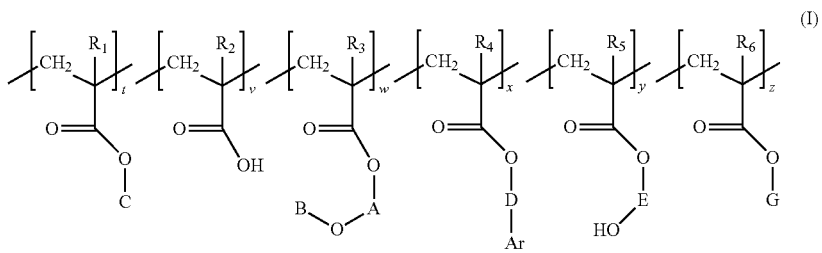

wherein $R_1$ to $R_6$ are, independently, —H, or —CH$_3$, A is a linear or branched $C_2$ to $C_{10}$ alkylene group, B is a $C_1$ to $C_{12}$ primary or secondary unsubstituted linear, branched, cyclic or alicyclic alkyl group, C is a $C_1$ to $C_{12}$ primary or secondary unsubstituted linear, branched, cyclic or alicyclic alkyl group, D is a linking group that is a direct valence bond, or a linear or branched $C_1$ to $C_{10}$, preferably $C_2$ to $C_{10}$ alkylene group, Ar is a substituted or unsubstituted aromatic group or heteroaromatic group, E is a linear or branched $C_2$ to $C_{10}$ alkylene group, G is an acid cleavable group, t is 0 mole % to about 40 mole %, v is 0 mole % to about 15 mole %, w is 0 mole % to about 45 mole %, x is 0 mole % to about 80 mole %, y is about 20 mole % to about 50 mole % and z is about 20 mole % to about 50 mole %, and further wherein the sum of t, v, w, x, y and z equals 100 mole %;

d) at least one glycidyl hydroxy benzoic acid condensate material comprising one or more compounds having structure (II),

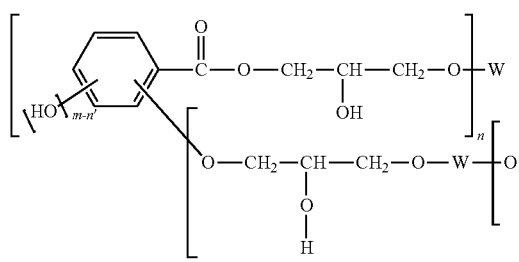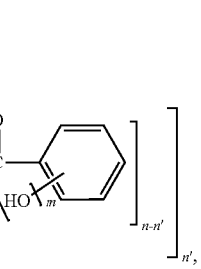

(II)

wherein,

W is an organic moiety having a molecular weight of 600 or less, wherein W forms an ether bond with the oxygen to which it is bound, m is an integer from 1 to 3 and n is an integer from 1 to 4, and further provided that when m is 1, n is 3 or 4, and when m is 2 or 3, n is an integer from 1 to 4, n' is 0 or 1, e) at least one heterocyclic thiol compound comprising a ring structure chosen from the general structures (III), (IIIa) or (IIIb), or tautomers thereof and

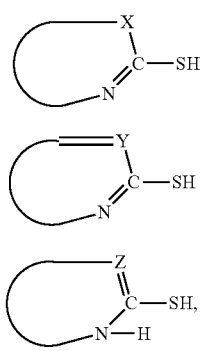

wherein, said ring structure is a single ring structure having from 4 to 8 atoms, or a multi ring structure having from 5 to 20 atoms; and wherein the single ring structure, or the multi ring structure comprises an aromatic, non-aromatic, or heteroaromatic ring, and in said structure (III), X is selected from the group consisting of $C(Rt_1)(Rt_2)$, O, S, Se, and Te;

in said structure (IIIa), Y is selected from the group consisting of $C(Rt_3)$ and N;

in said structure (IIIb), Z is selected from the group consisting of $C(Rt_3)$ and N; and $Rt_1$, $Rt_2$, and $Rt_3$ are independently selected from the group consisting of H, a substituted alkyl group having 1 to 8 carbon atoms, an unsubstituted alkyl group having 1 to 8 carbon atoms, a substituted alkenyl group having 2 to 8 carbon atoms, unsubstituted alkenyl group having 2 to 8 carbon atoms, a substituted alkynyl group having 2 to 8 carbon atoms, unsubstituted alkynyl group having 2 to 8 carbon atoms, a substituted aromatic group having 6 to 20 carbon atoms, a substituted heteroaromatic group having 3 to 20 carbon atoms, unsubstituted aromatic group having 6 to 20 carbon atoms and unsubstituted heteroaromatic group having 3 to 20 carbon atoms;

f) at least one solvent.

In a preferred embodiment, said glycidyl hydroxy benzoic acid condensate material having structure (II) is one wherein the moiety W is an aliphatic moiety selected from the group consisting an aliphatic hydrocarbon, an aliphatic alkyl ether, a bis(alkyl) sulfone, and a bis(alkyl)ketone. In another preferred embodiment, said glycidyl hydroxy benzoic acid condensate material having structure (II) is one wherein the moiety W is an aromatic moiety selected from an arene, a polycyclic arene, an bis(aryl)ether, a biphenyl, a bis(aryl) sulfone, bis(phenyl)alkylene, an (alkyl)(aryl)ketone, a bis (aryl)ketone, a bis(aryl)sulfone, and an (alkyl)(aryl)sulfone.

Component d) the glycidyl hydroxy benzoic acid condensate material comprising one or more compounds having structure (II) may be a single compound or a mixture of compounds resulting from the reaction of select glycidyl ether derivatives of an organic moiety W, with select hydroxybenzoic acid derivatives. Unexpectedly, only certain specific glycidyl hydroxy benzoic acid condensate materials, as are outlined by the structure (II), and its associated descriptive limitations, impart to the above described photoresist composition the ability to produce patterned photoresist film which may be used to form metallic lines with good adhesion during metal electroplating operations. These positive photoresist compositions also have a high photosensitivity, even in thick film applications, even on reflective substrates, and have process worthy development times. Additionally, this novel photoresist composition also has low dark film loss in developers. The resistance for adhesion failure for metallization can enable electroplating metallic lines without loss of adhesion and adhesion loss during subsequent lithographic etching processes.

As outlined above, the descriptive limitation described in the embodiment of glycidyl hydroxy benzoic acid condensate material is that W is an organic moiety having a molecular weight of 600 or less and where this organic moiety W forms an ether bond with the oxygen to which it is bound. Another limitation is that m, the number of hydroxy moieties on the benzoic acid part of structure (II), is an integer from 1 to 3 and that n the number of glycidyl derived moieties on the organic moiety, is an integer from 1 to 4. A further limitation to these parameters is that when m is 1, n must be 3, or 4, and that when m is 2 or 3, then n ranges from 1 to 4. The n' term specifies how many glycidyl derived moieties on W have reacted with a hydroxy phenolic moiety of a given hydroxybenzoic acid derivative instead of reacting with the carboxylic acid. The term n' may be 0 or 1.

In another embodiment of the above described positive working photosensitive composition said glycidyl hydroxy benzoic acid condensate material is one wherein m is 1. In yet another embodiment m is 2. In still another m is 3.

In another embodiment of the any of the above described positive working photosensitive compositions said glycidyl hydroxy benzoic acid condensate material is one wherein n is 1. In yet another n is 2. In still another aspect n is 3. In yet another aspect n is 4.

In another embodiment of the any of the above described positive working photosensitive compositions said glycidyl hydroxy benzoic acid condensate material is one wherein n' is 0. In yet another aspect n' is 1.

In another embodiment of the above described positive working photosensitive compositions component d), said glycidyl hydroxy benzoic acid condensate material, is one wherein it comprises at least one compound having structure (IVa-1), wherein n is 3 to 4, and Rw is OH or the moiety (Wb-1), wherein the term ∿ represents the point of attachment in the moiety (IVb-1) to the compound of structure (IVa-1).

(IVa-1)

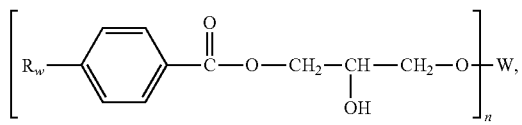

(IVb-1)

In another embodiment of the above described positive working photosensitive compositions said glycidyl hydroxy benzoic acid condensate material comprises at least one compound having structure (W-1), wherein n is 3 to 4.

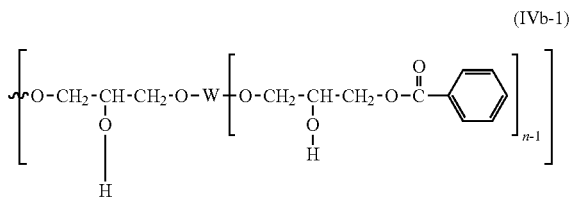

(IV-1)

In another embodiment of the above described positive working photosensitive compositions said glycidyl hydroxy benzoic acid condensate material comprises at least one compound having structure (IVa-2). Further, in this embodiment, n is 1 to 4, Rw1 is OH or the moiety (IVb-2), and the term ∿ represents the point of attachment in moiety (IVb-2) to said compound of structure (IVa-2).

(IVa-2)

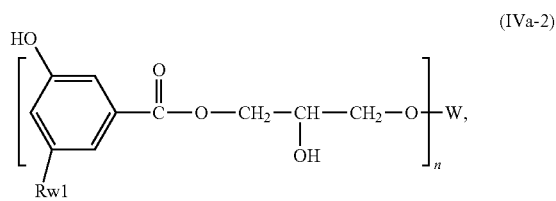

(IVb-2)

In another embodiment of the above described positive working photosensitive compositions said glycidyl hydroxy benzoic acid condensate material is one which comprises at least one compound having structure (IV-2), wherein n is 1 to 4.

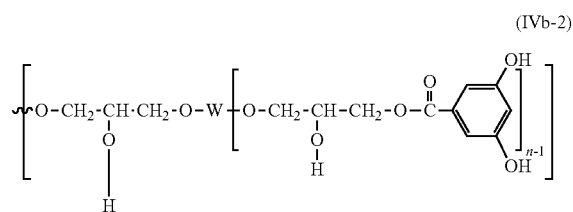

(IV-2)

In another embodiment of the above described positive working photosensitive compositions said glycidyl hydroxy benzoic acid condensate material comprises at least one compound having structure (IVa-3), wherein n is 1 to 4, and Rw2 is OH or the moiety (IVa), provided that no more than one Rw2 is the moiety (IVb-3), and ∿ represents the point of attachment in the moiety (IVb-3) in said compound of structure (IVa-3).

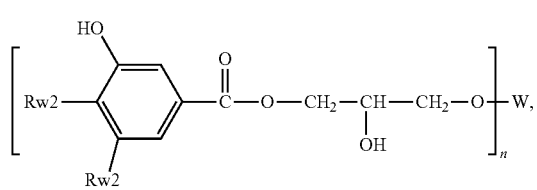
(IVa-3)

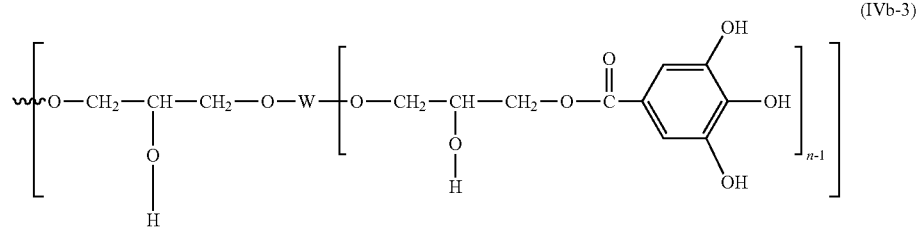
(IVb-3)

In another embodiment of the above described positive working photosensitive compositions said glycidyl hydroxy benzoic acid condensate material comprises at least one compound having structure (IV-3), wherein n is 1 to 4.

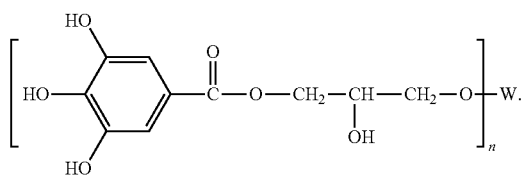
(IV-3)

In another embodiment of the above described positive working photosensitive compositions said organic moiety W is selected from the group consisting of moieties of structure (Wa), (Wb), (Wc), (Wd), (We) and (Wf). In this embodiment ⌇ represents an attachment point within each of these organic moieties, where it forms an ether bond with the oxygen in said glycidyl hydroxy benzoic acid condensate material of structure (II). Further, in this embodiment, Xa is a moiety selected from the group consisting of a direct valence bond, alkylene, —SO$_2$—, —C(=O)— and —O—; Ra1, Rb1 and Rc are independently selected from a C$_1$ to C$_5$ alkyl or C$_2$ to C$_5$ alkyleneoxyalkyl; Ra2 is selected from a C$_1$ to C$_5$ alkyl an C$_2$ to C$_5$ alkyleneoxyalkyl, a C$_1$ to C$_5$ alkyloxy, a halide, a C$_1$ to C$_5$ alkylsulfonyl a C$_1$ to C$_5$ alkylcarbonyl, and a C$_1$ to C$_5$ alkylcarbonyloxy, and n″ ranges from 0 to 12.

(Wa)

(Wb)

(Wc)

-continued

(Wd)

(We)

(Wf)

In another embodiment of the above described positive working photosensitive compositions said organic moiety W is selected from the group consisting of moieties of structures (Wa1), (Wb1), (Wc1), (Wd1) and (We1). In this embodiment ⌇ represents an attachment point within each of these organic moieties, where it forms an ether bond with the oxygen in said glycidyl hydroxy benzoic acid condensate material of structure (II).

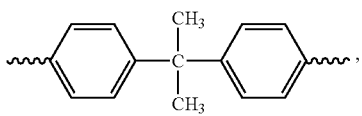
(Wa1)

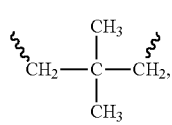
(Wb1)

(Wc1)

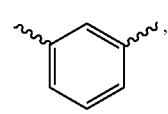
(Wd1)

-continued (We1)

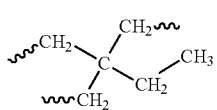

In another embodiment of the above described positive working photosensitive compositions said glycidyl hydroxy benzoic acid condensate material comprises at least one compound having structure (Va-1), wherein Rw3 is OH, or a moiety of structure (Vb-1), where ∿ represents the point of attachment in this moiety. Also, in this embodiment m is 2 to 3, n' is 0 or 1, and Xa is selected from the group consisting of a direct valence bond, alkylene, —SO$_2$—, —C(=O)— and —O—. In another aspect of this embodiment m is 2. In yet another aspect of this embodiment m is 3.

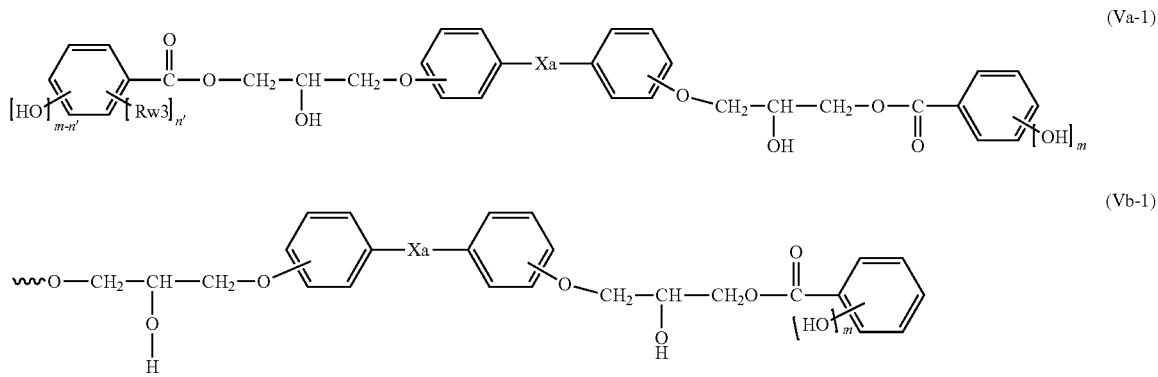

(Va-1)

(Vb-1)

In another embodiment of the above described positive working photosensitive compositions said glycidyl hydroxy benzoic acid condensate material comprises at least one compound having structure (V-1), wherein m is 2 to 3, and Xa is selected from the group consisting of a direct valence bond, alkylene, —SO$_2$—, —C(=O)— and —O—. In another aspect of this embodiment m is 2. In yet another aspect of this embodiment m is 3.

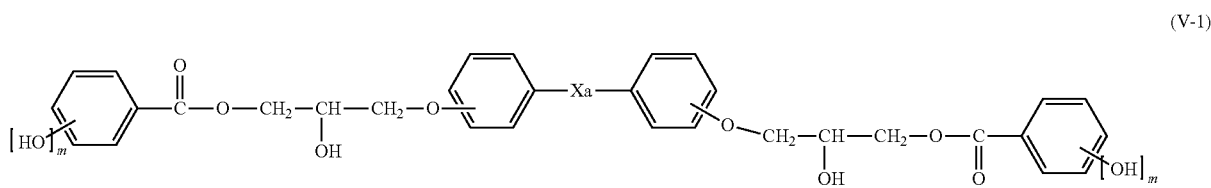

(V-1)

In another embodiment of the above described positive working photosensitive compositions said glycidyl hydroxy benzoic acid condensate material comprises at least one compound having structure (Va-2), wherein Rw4 is OH or a moiety of structure (Vb-2), wherein ∿ represents the point of attachment in this moiety. Further, in this embodiment and Xa is selected from the group consisting of a direct valence bond, alkylene, —SO$_2$—, —C(=O)— and —O—.

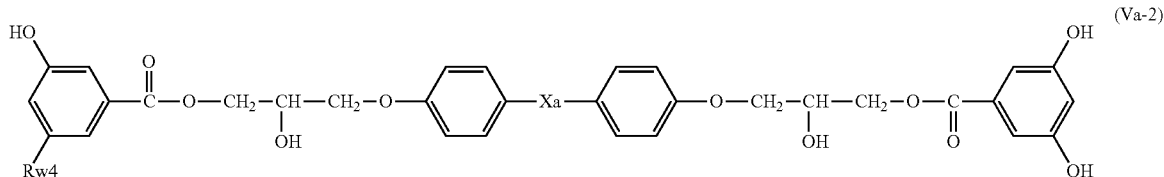

(Va-2)

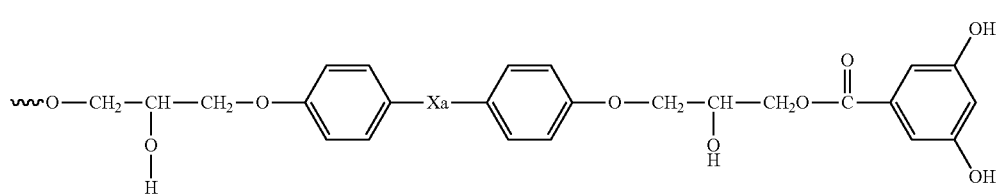
(Vb-2)

In another embodiment of the above described positive working photosensitive compositions said glycidyl hydroxy benzoic acid condensate material comprises at least one compound having structure (V-2), wherein, Xa is selected from the group consisting of a direct valence bond, alkylene, —$SO_2$—, —C(═O)— and —O—.

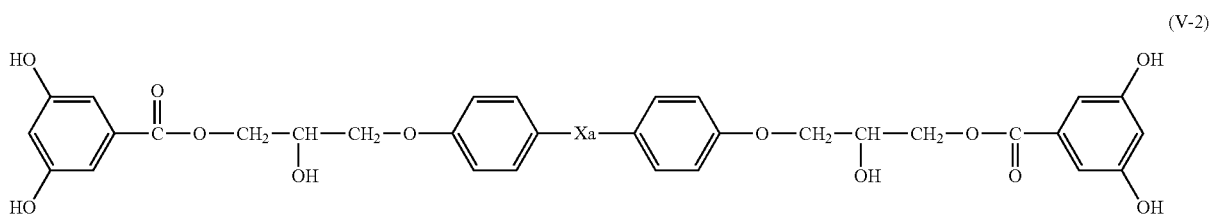
(V-2)

In another embodiment of the above described positive working photosensitive compositions said glycidyl hydroxy benzoic acid condensate material comprises at least one compound having structure (Va-3), wherein Rw5 is OH or a moiety of structure (Vb-3), wherein ～ represents the point of attachment in this moiety.

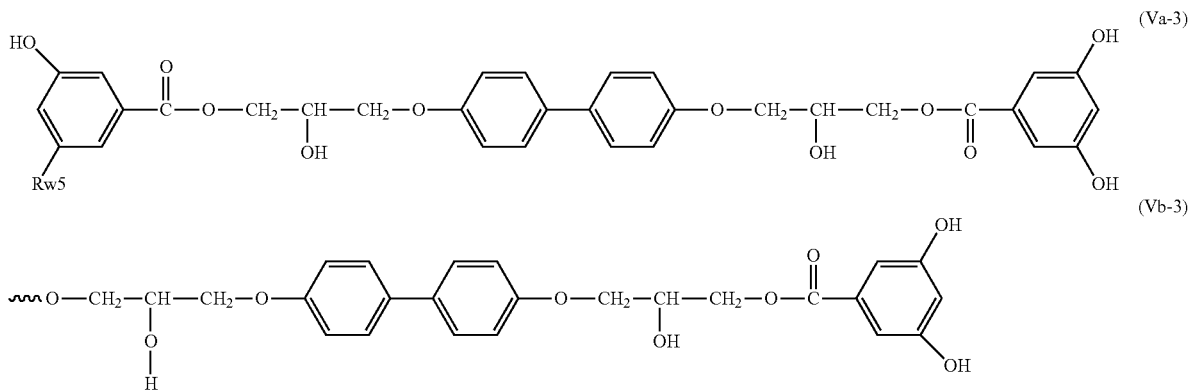

In another embodiment of the above described positive working photosensitive compositions said glycidyl hydroxy benzoic acid condensate material comprises at least one compound having structure (V-3). Preferably, in this embodiment said glycidyl hydroxyl benzoic acid condensate material is the compound (V-3).

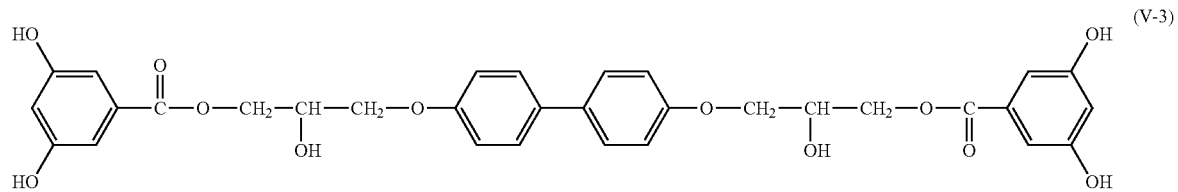 [SMILES: O=C(OCC(O)COc1ccc(-c2ccc(OCC(O)COC(=O)c3cc(O)cc(O)c3)cc2)cc1)c1cc(O)cc(O)c1]
(V-3)

In another embodiment of the above described positive working photosensitive compositions said glycidyl hydroxy benzoic acid condensate material comprises at least one compound having structure (Va-4), wherein Rw6 is OH or a moiety of structure (Vb-4), wherein ⁓ represents the point of attachment in this moiety.

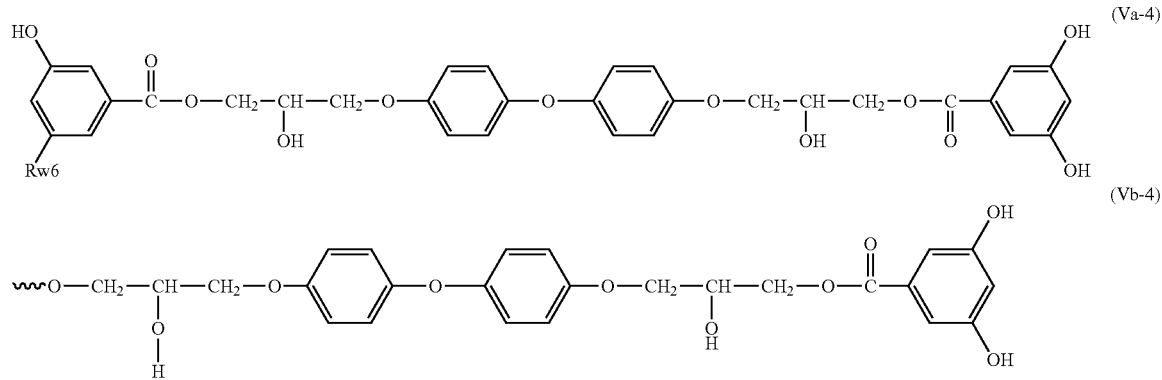

In another embodiment of the above described positive working photosensitive compositions said glycidyl hydroxy benzoic acid condensate material comprises at least one compound having structure (V-4). Preferably, in this embodiment said glycidyl hydroxy benzoic acid condensate material is the compound having structure (V-4).

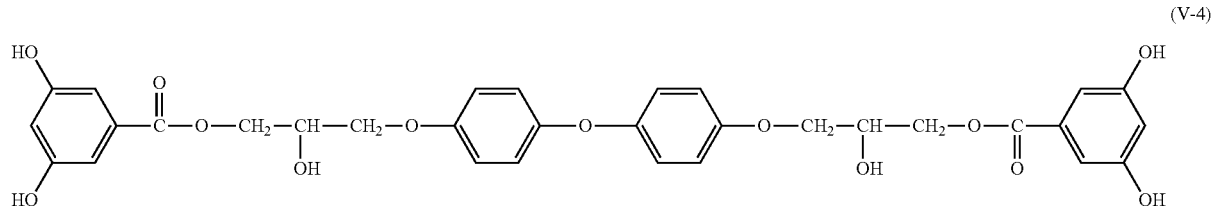 [SMILES: O=C(OCC(O)COc1ccc(Oc2ccc(OCC(O)COC(=O)c3cc(O)cc(O)c3)cc2)cc1)c1cc(O)cc(O)c1]

In another embodiment of the above described positive working photosensitive compositions said glycidyl hydroxy benzoic acid condensate material comprises at least one compound having structure (Va-5), wherein Rw7 is OH or a moiety of structure (Vb-5), wherein ⁓ represents the point of attachment in this moiety,

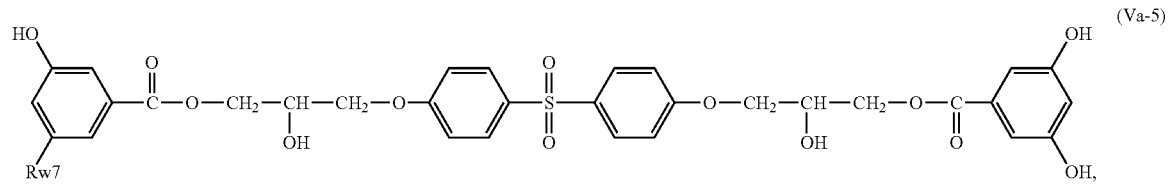

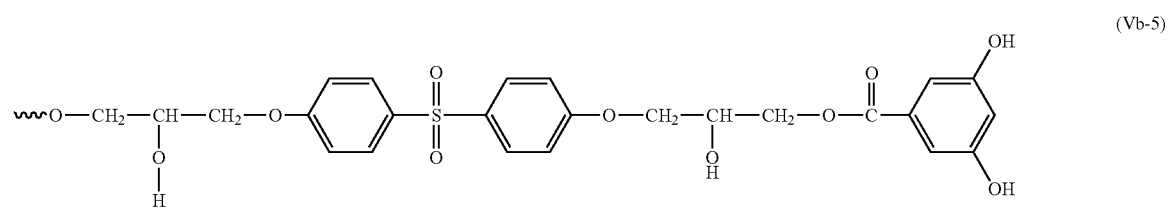

In another embodiment of the above described positive working photosensitive compositions said glycidyl hydroxy benzoic acid condensate material comprises at least one compound having structure (V-5). Preferably, in this embodiment said glycidyl hydroxy benzoic acid condensate material is the compound having structure (V-5).

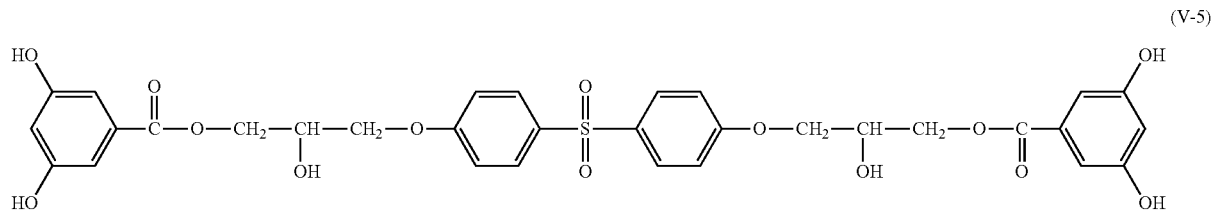 [SMILES: O=C(OCC(O)COc1ccc(S(=O)(=O)c2ccc(OCC(O)COC(=O)c3cc(O)cc(O)c3)cc2)cc1)c1cc(O)cc(O)c1]
(V-5)

In another embodiment of the above described positive working photosensitive compositions said glycidyl hydroxy benzoic acid condensate material comprises at least one compound having structure (Va-6), wherein Rw8 is OH or a moiety of structure (Vb-6), wherein ⌇ represents the point of attachment in this moiety.

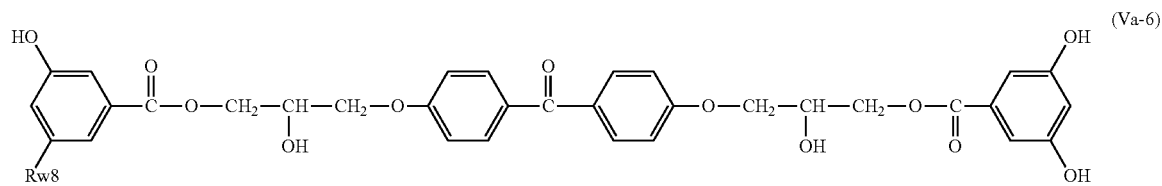
(Va-6)

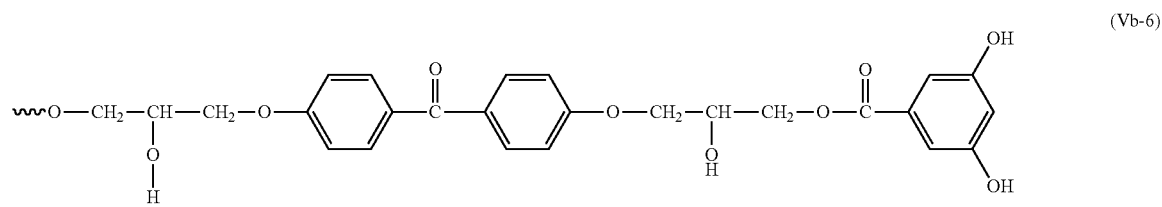
(Vb-6)

In another embodiment of the above described positive working photosensitive compositions said glycidyl hydroxy benzoic acid condensate material comprises at least one compound having structure (V-6).

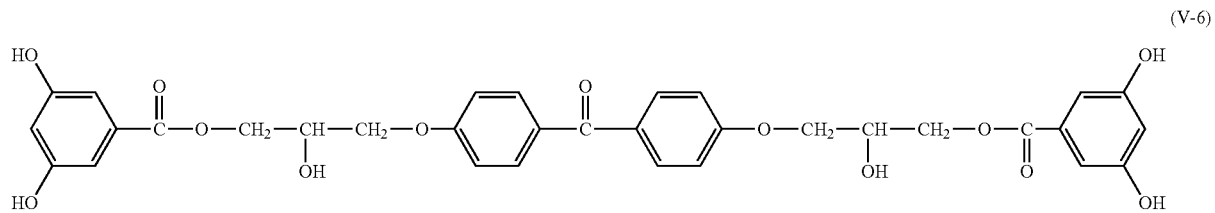
(V-6)

In another embodiment of the above described positive working photosensitive compositions said glycidyl hydroxy benzoic acid condensate material comprises at least one compound having structure (Va-7), wherein Rw9 is OH or a moiety of structure (Vb-7), wherein ⌇ represents the point of attachment in this moiety, and further wherein Xa is an alkylene moiety.

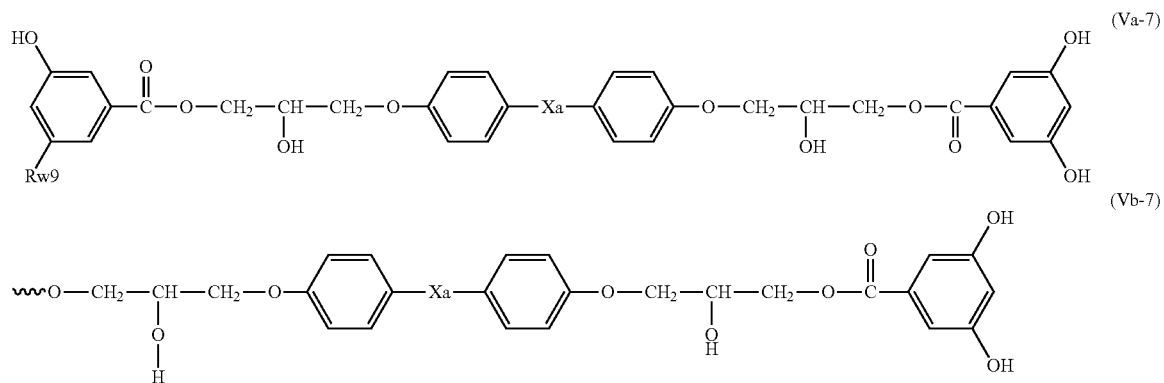

(Va-7)

(Vb-7)

In another embodiment of the above described positive working photosensitive compositions said glycidyl hydroxy benzoic acid condensate material comprises at least one compound having structure (V-7), wherein Xa is an alkylene moiety

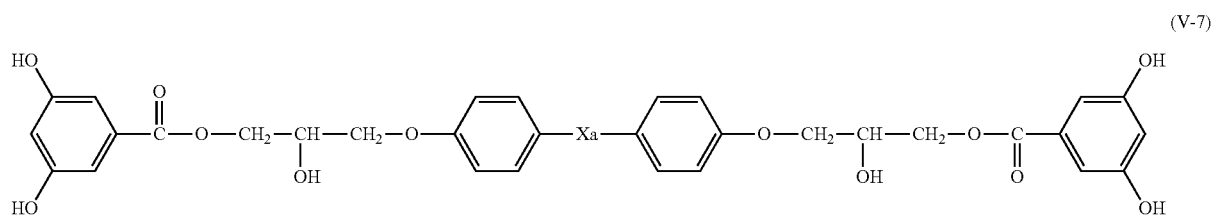

(V-7)

In another embodiment of the above described positive working photosensitive compositions said glycidyl hydroxy benzoic acid condensate material comprises at least one compound having structure (Va-8), wherein Ra and Rb are independently a $C_1$ to $C_5$ alkyl moiety, or a $C_2$ to $C_5$-alkylene-O-alkyl moiety, and Rw10 is OH or a moiety of structure (Vb-8), wherein ∿∿ represents the point of attachment in this moiety.

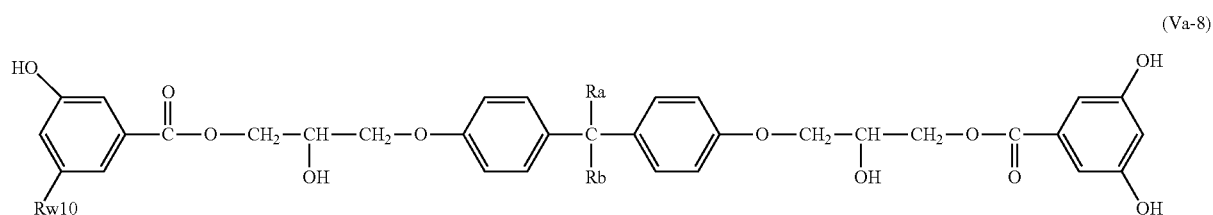

(Va-8)

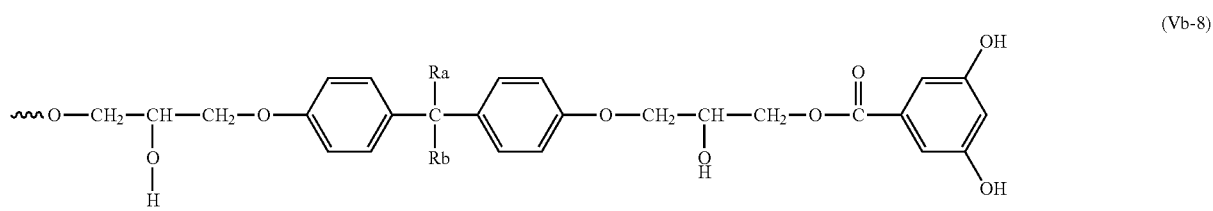

(Vb-8)

In another embodiment of the above described positive working photosensitive compositions said glycidyl hydroxy benzoic acid condensate material comprises at least one compound having structure (V-8), wherein Ra and Rb are independently a $C_1$ to $C_5$ alkyl moiety, or a $C_2$ to $C_5$-alkylene-O-alkyl moiety.

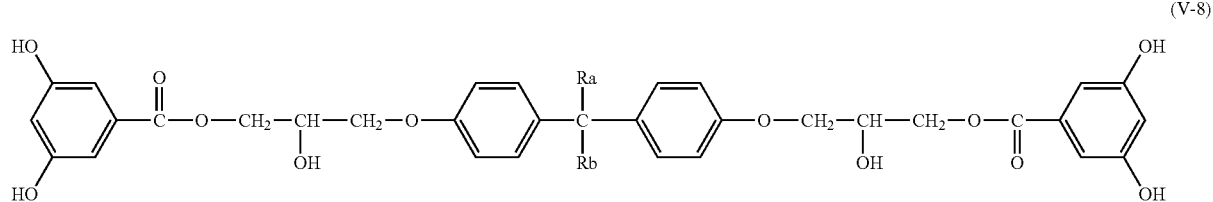

(V-8)

In another embodiment of the above described positive working photosensitive compositions said glycidyl hydroxy benzoic acid condensate material comprises at least one compound having structure (Va-9), wherein Rw11 is OH or a moiety of structure (Vb-9), wherein ⌇ represents the point of attachment in this moiety.

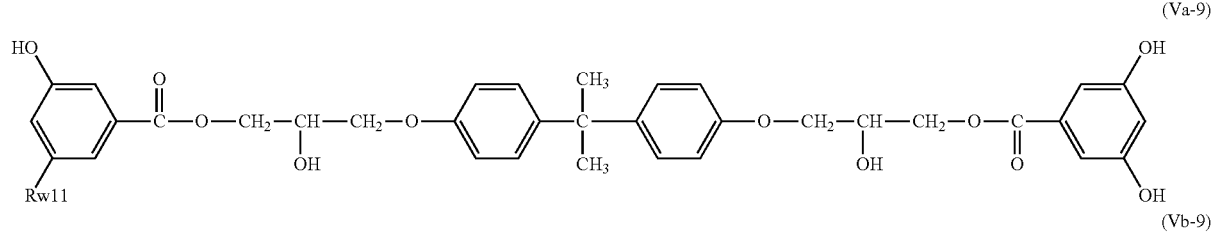

(Va-9)

(Vb-9)

In another embodiment of the above described positive working photosensitive compositions said glycidyl hydroxy benzoic acid condensate material comprises at least one compound having structure (V-9). Preferably, in this embodiment said glycidyl hydroxy benzoic acid condensate material is the compound having structure (V-9).

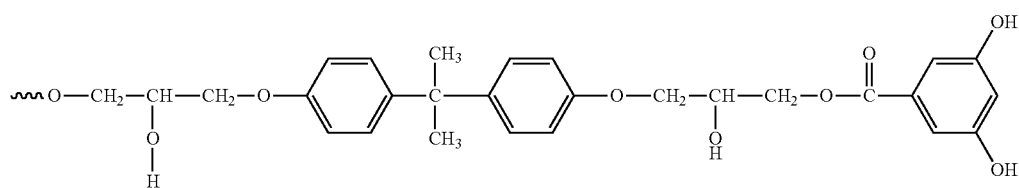

(V-9)

In another embodiment of the above described positive working photosensitive compositions said glycidyl hydroxy benzoic acid condensate material comprises at least one compound having structure (Va-10), wherein Rw12 is OH or the moiety (Vb-10), wherein ⌇ represents the point of attachment in this moiety, provided that no more than one Rw12 is the moiety (Vb-10), and further wherein, Xa is selected from the group consisting of a direct valence bond, alkylene, —$SO_2$—, —C(=O)— and —O—.

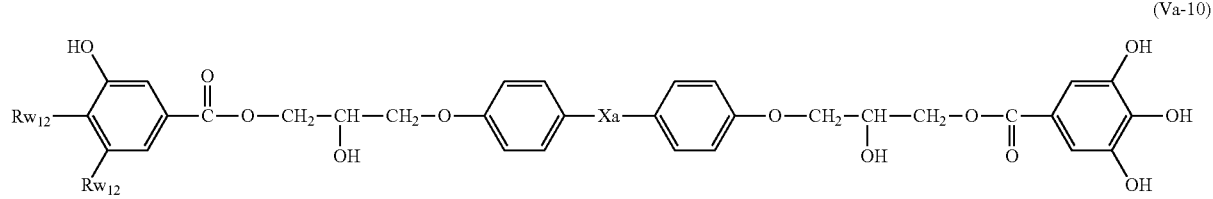

(Va-10)

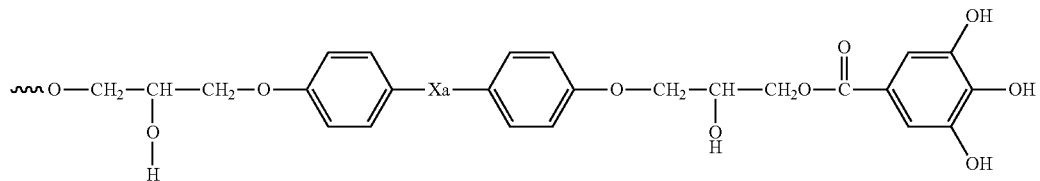
(Vb-10)

In another embodiment of the above described positive working photosensitive compositions said glycidyl hydroxy benzoic acid condensate material comprises at least one compound having structure (Va-11), wherein Rw13 is OH or the moiety (Vb-11), wherein ∿∿ represents the point of attachment in this moiety, provided that no more than one Rw13 is (Vb-11).

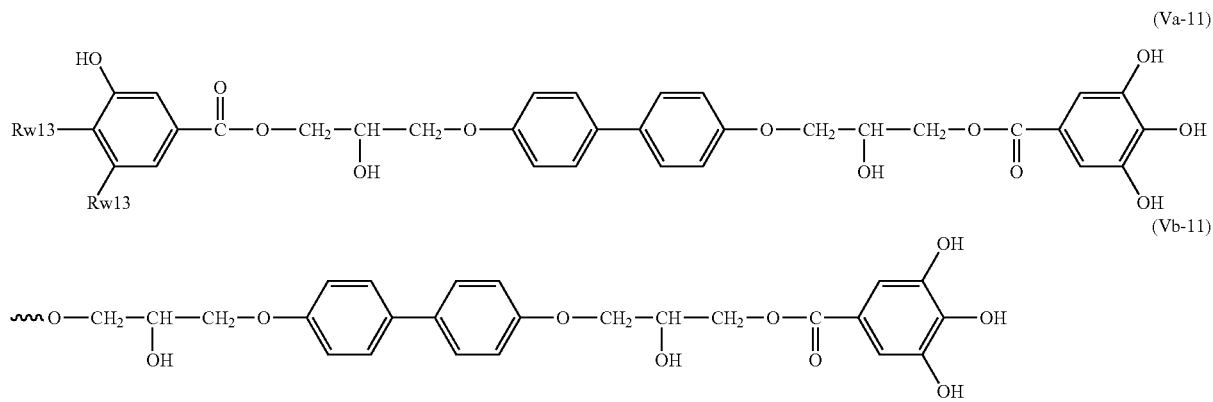

In another embodiment of the above described positive working photosensitive compositions said glycidyl hydroxy benzoic acid condensate material comprises at least one compound having structure (V-11),

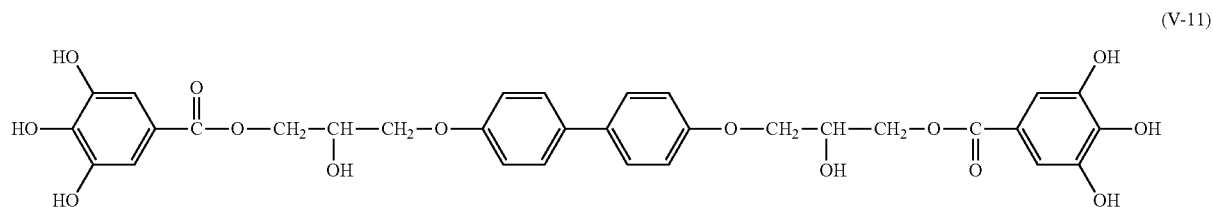 [SMILES: O=C(OCC(O)COc1ccc(-c2ccc(OCC(O)COC(=O)c3cc(O)c(O)c(O)c3)cc2)cc1)c1cc(O)c(O)c(O)c1]

In another embodiment of the above described positive working photosensitive compositions said glycidyl hydroxy benzoic acid condensate material comprises at least one compound having structure (Va-12), wherein Rw14 is OH or the moiety (Vb-12), wherein ∿∿ represents the point of attachment in this moiety, provided that no more than one Rw14 is the moiety (Vb-12).

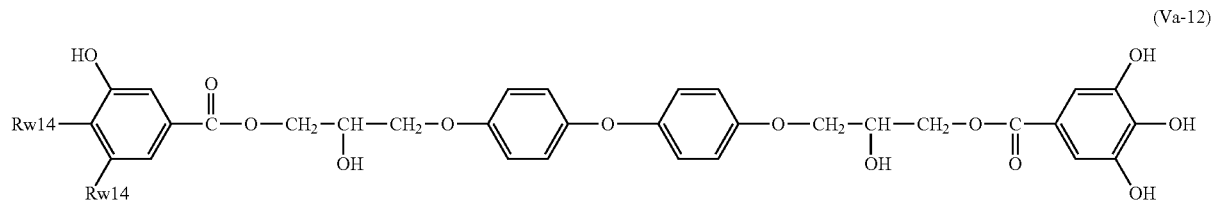

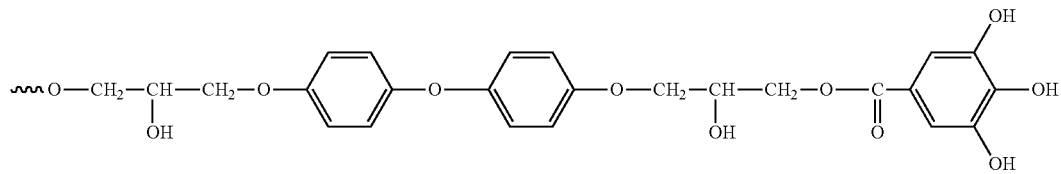
(Vb-12)

In another embodiment of the above described positive working photosensitive compositions said glycidyl hydroxy benzoic acid condensate material comprises at least one compound having structure (V-12),

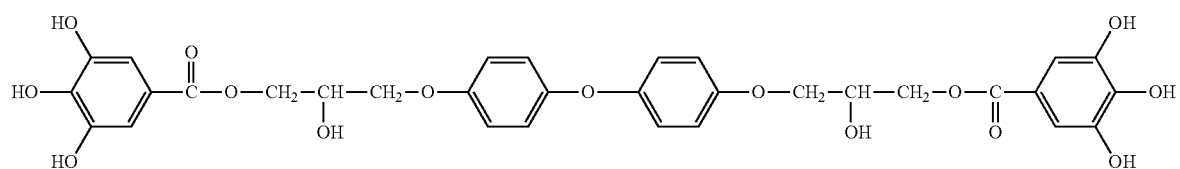
(V-12)

In another embodiment of the above described positive working photosensitive compositions said glycidyl hydroxy benzoic acid condensate material comprises at least one compound having structure (Va-13), wherein Rw15 is OH or the moiety (Vb-13), wherein ∿ represents the point of attachment in this moiety, provided that no more than one Rw15 is the moiety (Vb-13),

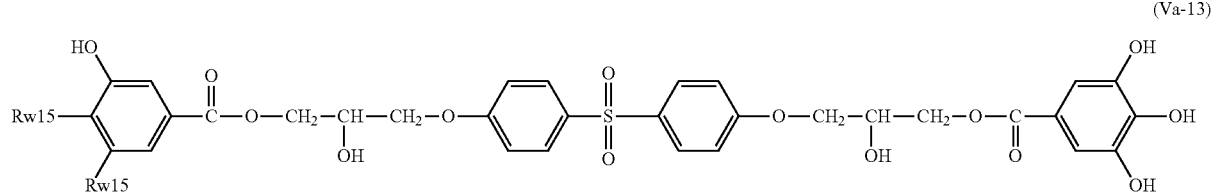
(Va-13)

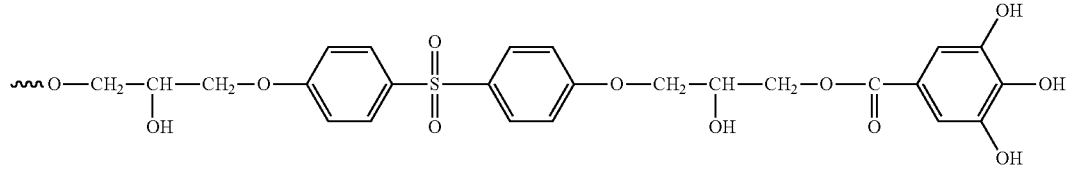
(Vb-13)

In another embodiment of the above described positive working photosensitive compositions said glycidyl hydroxy benzoic acid condensate material comprises at least one compound having structure (V-13). Preferably, in this embodiment said glycidyl hydroxy benzoic acid condensate material is the compound having structure (V-13).

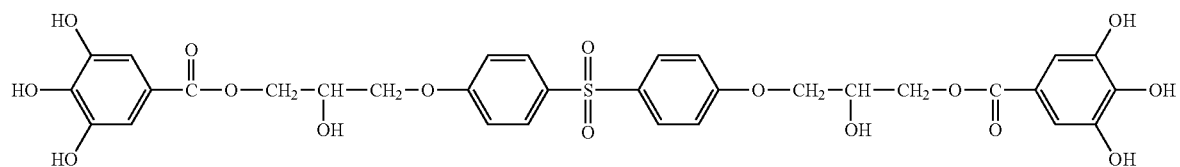
(V-13)

In another embodiment of the above described positive working photosensitive compositions said glycidyl hydroxy benzoic acid condensate material comprises at least one compound having structure (Va-14), wherein Rw16 is OH or the moiety (Vb-14), wherein ∿∿ represents the point of attachment in this moieties, provided that no more than one Rw16 is the moiety (Vb-14).

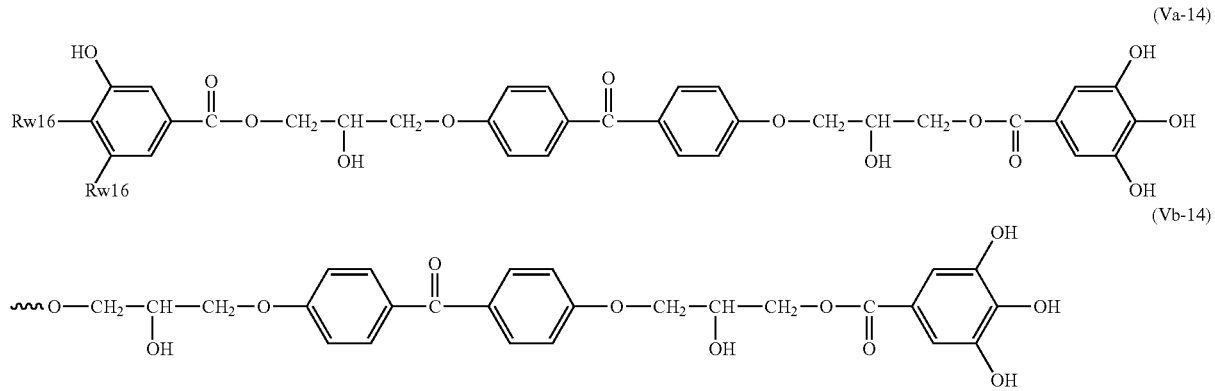

In another embodiment of the above described positive working photosensitive compositions said glycidyl hydroxy benzoic acid condensate material comprises at least one compound having structure (V-14). Preferably, in this embodiment said glycidyl hydroxy benzoic acid condensate material is the compound having structure (V-14).

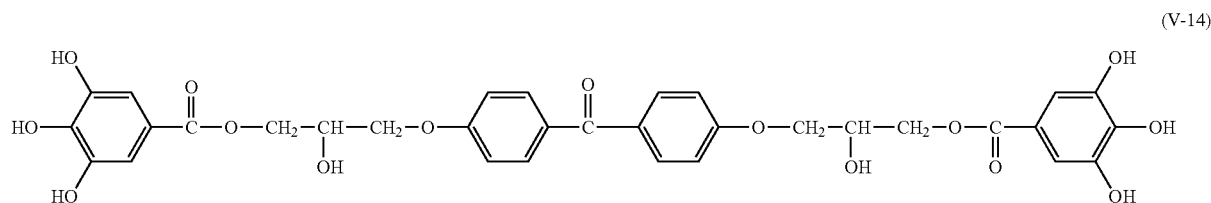 [SMILES: O=C(OCC(O)COc1ccc(C(=O)c2ccc(OCC(O)COC(=O)c3cc(O)c(O)c(O)c3)cc2)cc1)c1cc(O)c(O)c(O)c1]

In another embodiment of the above described positive working photosensitive compositions said glycidyl hydroxy benzoic acid condensate material comprises at least one compound having structure (Va-15), wherein Rw17 is OH or the moiety (Vb-15), wherein ∿∿ represents the point of attachment in this moiety, provided that no more than one Rw17 is the moiety (Vb-15), and further wherein Xa is an alkylene moiety.

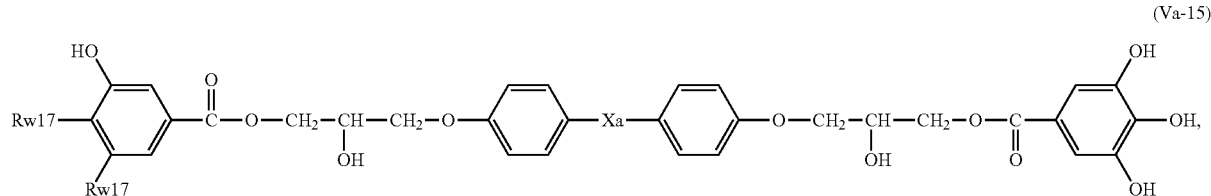

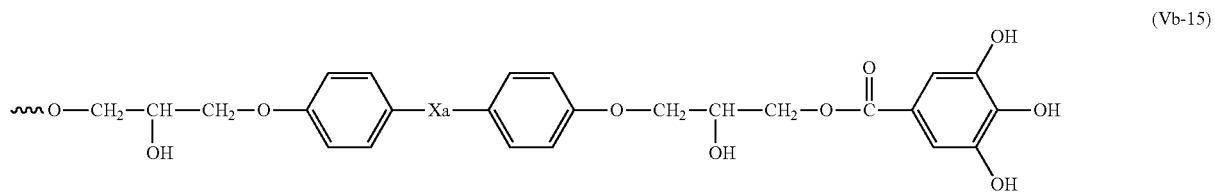

In another embodiment of the above described positive working photosensitive compositions said glycidyl hydroxy benzoic acid condensate material comprises at least one compound having structure (V-15), wherein Xa is an alkylene moiety. Preferably, in this embodiment said glycidyl hydroxy benzoic acid condensate material is the compound having structure (V-15).

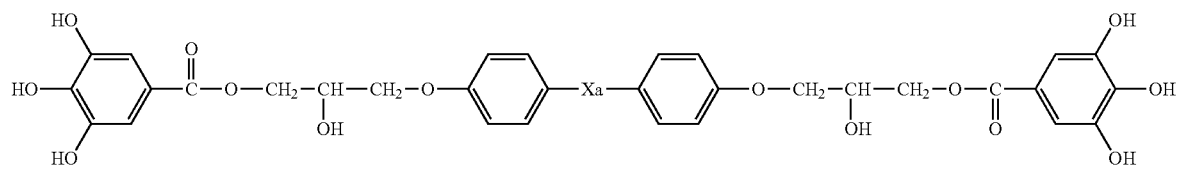

(V-15)

In another embodiment of the above described positive working photosensitive compositions said glycidyl hydroxy benzoic acid condensate material comprises at least one compound having structure (Va-16), wherein Rw18 is OH or the moiety (Vb-16), wherein ∿ represents the point of attachment in these moieties, provided that no more than one Rw18 is the moiety (Vb-16), and further wherein, Ra and Rb are independently a $C_1$ to $C_5$ alkyl moiety, or a $C_2$ to $C_5$-alkylene-O-alkyl moiety.

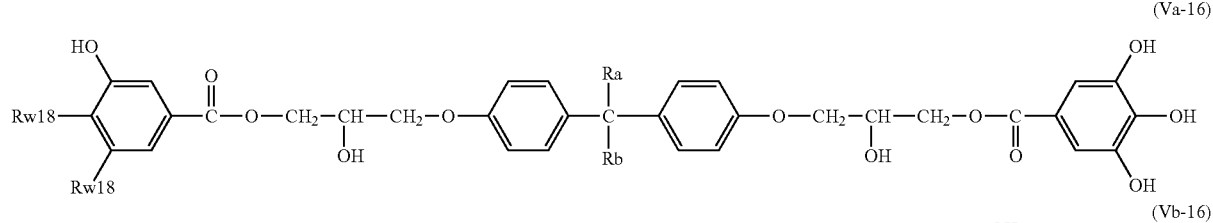

(Va-16)

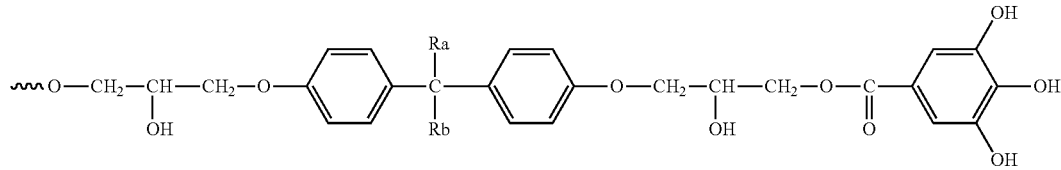

(Vb-16)

In another embodiment of the above described positive working photosensitive compositions said glycidyl hydroxy benzoic acid condensate material comprises at least one compound having structure (V-16), wherein Ra and Rb are independently a $C_1$ to $C_5$ alkyl moiety, or a $C_2$ to $C_5$-alkylene-O-alkyl moiety. Preferably, in this embodiment said glycidyl hydroxy benzoic acid condensate material is the compound having structure (V-16).

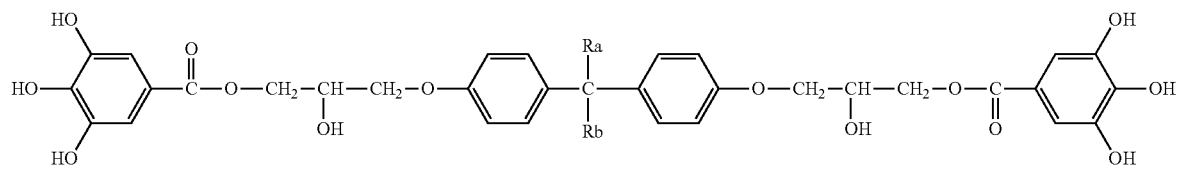

(V-16)

In another embodiment of the above described positive working photosensitive compositions said glycidyl hydroxy benzoic acid condensate material comprises at least one compound having structure (Va-17), wherein Rw19 is OH or the moiety (Vb-17), wherein ∿ represents the point of attachment in these moieties, provided that no more than one Rw19 is the moiety (Vb-17).

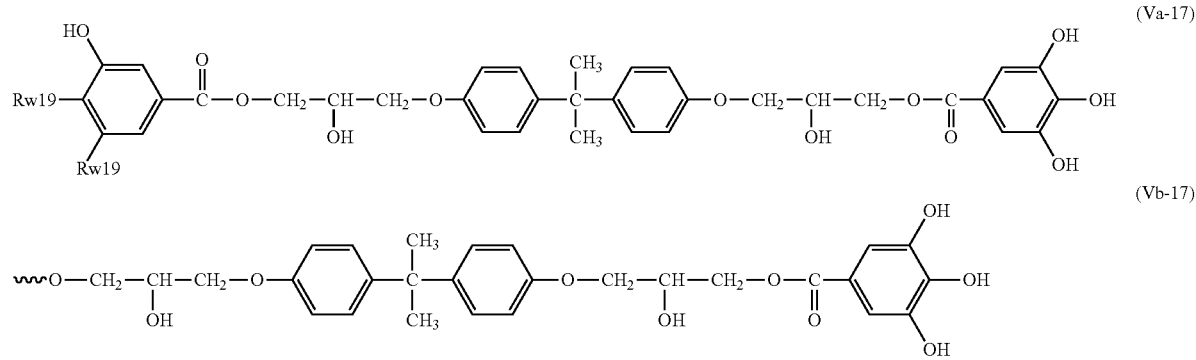

In another embodiment of the above described positive working photosensitive compositions said glycidyl hydroxy benzoic acid condensate material comprises at least one compound having structure (V-17). Preferably, in this embodiment said glycidyl hydroxy benzoic acid condensate material is the compound having structure (V-17).

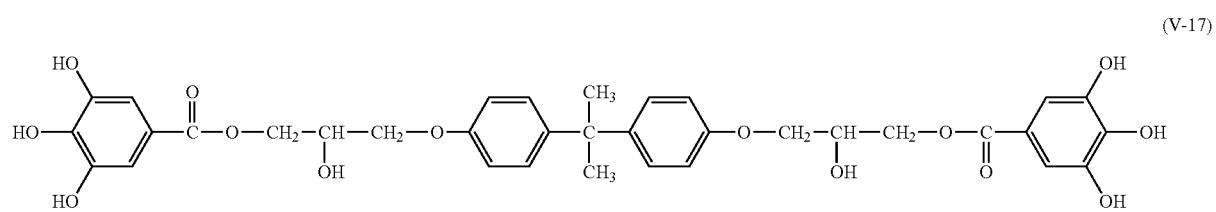 [SMILES: CC(C)(c1ccc(OCC(O)COC(=O)c2cc(O)c(O)c(O)c2)cc1)c1ccc(OCC(O)COC(=O)c2cc(O)c(O)c(O)c2)cc1]

In another embodiment of the above described positive working photosensitive compositions said glycidyl hydroxy benzoic acid condensate material comprises at least one compound having structure (VIa-1), wherein Rw20 is OH, or a moiety of structure (VIb-1), wherein ⁓ represents the point of attachment in this moiety. In this embodiment m is 2 to 3, and n' is 0 or 1. Also, in this embodiment Ra1 and Rb1 are independently selected from a $C_1$ to $C_5$ alkyl or a $C_2$ to $C_5$-alkylene-O-alkyl moiety.

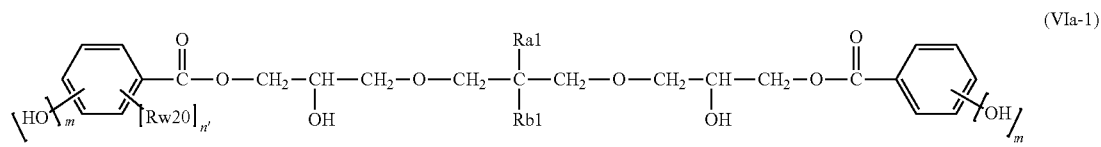

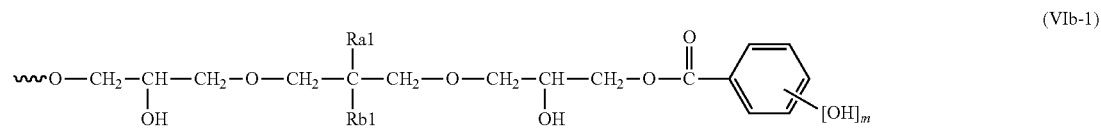

In another embodiment of the above described positive working photosensitive compositions said glycidyl hydroxy benzoic acid condensate material comprises at least one compound having structure (VI-1), wherein Ra1 and Rb1 are independently selected from a $C_1$ to $C_5$ alkyl or a $C_2$ to $C_5$-alkylene-O-alkyl moiety, and m is 2 or 3. In another aspect of this embodiment m is 3. In yet another aspect of this embodiment m is 2.

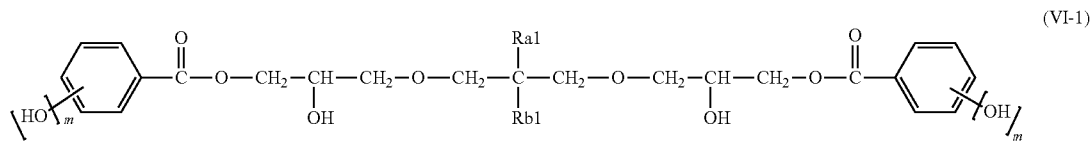

(VI-1)

In another embodiment of the above described positive working photosensitive compositions said glycidyl hydroxy benzoic acid condensate material comprises at least one compound having structure (VIa-2), wherein Rw21 is OH or a moiety of structure (VIb-2), wherein ∿∿ represents the point of attachment in this moiety, and further wherein Ra1 and Rb1 are independently selected from a $C_1$ to $C_5$ alkyl or a $C_2$ to $C_5$-alkylene-O-alkyl moiety.

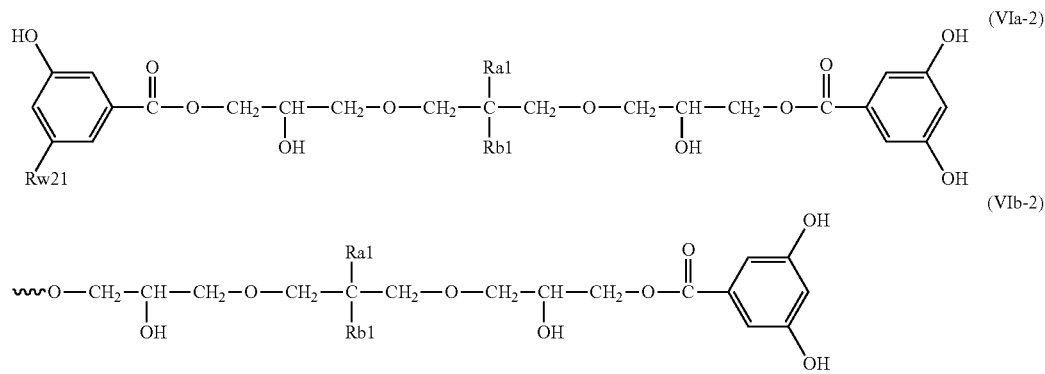

In another embodiment of the above described positive working photosensitive compositions said glycidyl hydroxy benzoic acid condensate material comprises at least one compound having structure (VI-2), wherein Ra1 and Rb1 are independently selected from a $C_1$ to $C_5$ alkyl or a $C_2$ to $C_5$-alkylene-O-alkyl moiety.

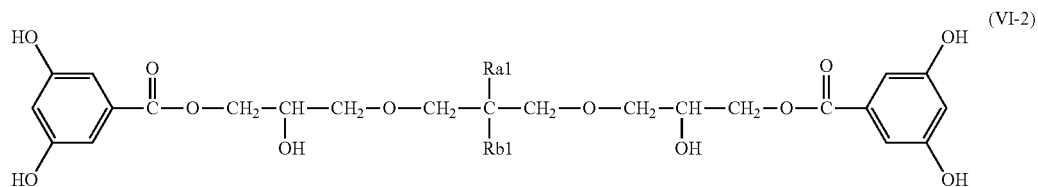

In another embodiment of the above described positive working photosensitive compositions said glycidyl hydroxy benzoic acid condensate material comprises at least one compound having structure (VIa-3), wherein Rw22 is OH or the moiety (VIb-3), wherein ∿∿ represents the point of attachment in this moiety, provided that no more than one Rw22 is the moiety (VIb-3). In this embodiment Ra1 and Rb1 are independently selected from a $C_1$ to $C_5$ alkyl or a $C_2$ to $C_5$-alkylene-O-alkyl moiety.

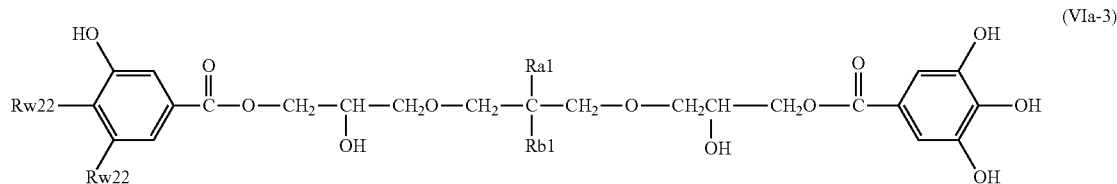

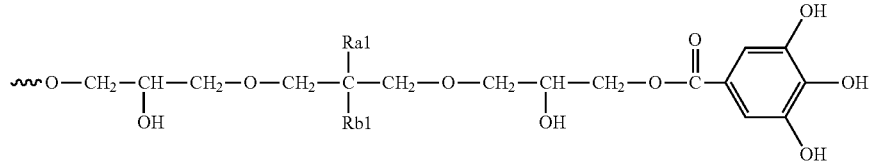
(VIb-3)

In another embodiment of the above described positive working photosensitive compositions said glycidyl hydroxy benzoic acid condensate material comprises at least one compound having structure (VI-3), wherein Ra1 and Rb1 are independently selected from a $C_1$ to $C_5$ alkyl or a $C_2$ to $C_5$-alkylene-O-alkyl moiety.

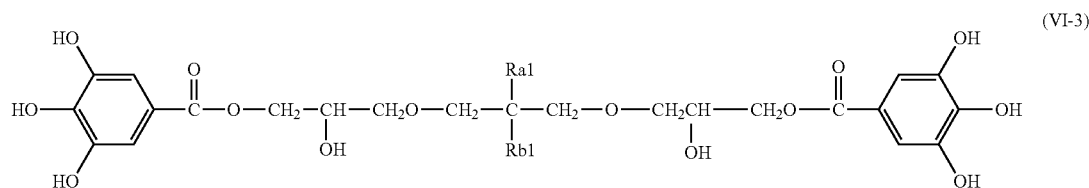
(VI-3)

In another embodiment of the above described positive working photosensitive compositions said glycidyl hydroxy benzoic acid condensate material comprises at least one compound having structure (VIIa-1), wherein Rw23 is OH, or a moiety of structure (VIIb-1), wherein ⁓ represents the point of attachment in this moiety. In this embodiment m is 1, 2 or 3, and n' is 0 or 1, and also, Ra2 is selected from a $C_1$ to $C_5$ alkyl or a $C_2$ to $C_5$-alkylene-O-alkyl moiety, and m is 1, 2 or 3. In another aspect of this embodiment m is 3. In yet another aspect of this embodiment m is 2. In still yet another aspect of this embodiment m is 1.

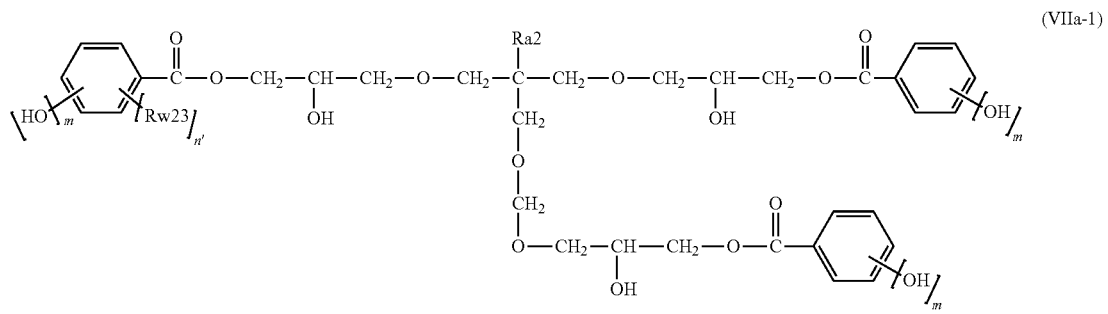
(VIIa-1)

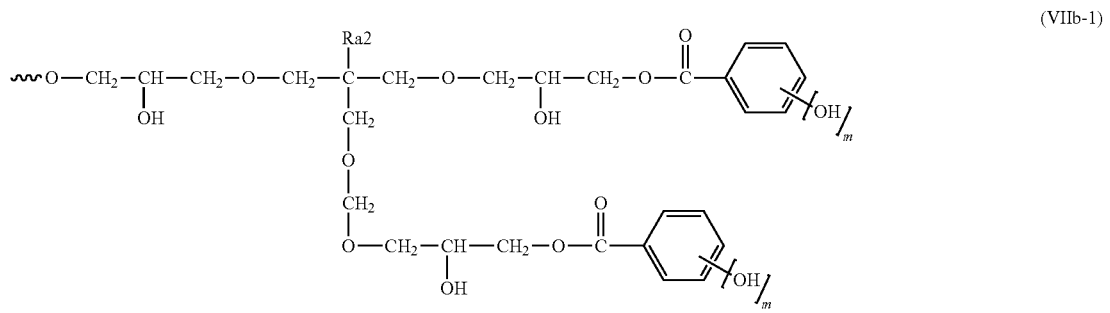
(VIIb-1)

In another embodiment of the above described positive working photosensitive compositions said glycidyl hydroxy benzoic acid condensate material comprises at least one compound having structure (VII-1), wherein Ra2 is selected from a $C_1$ to $C_5$ alkyl or a $C_2$ to $C_5$-alkylene-O-alkyl moiety, and m is 1, 2 or 3. In another aspect of this embodiment m is 3. In yet another aspect of this embodiment m is 2. In still yet another aspect of this embodiment m is 1.

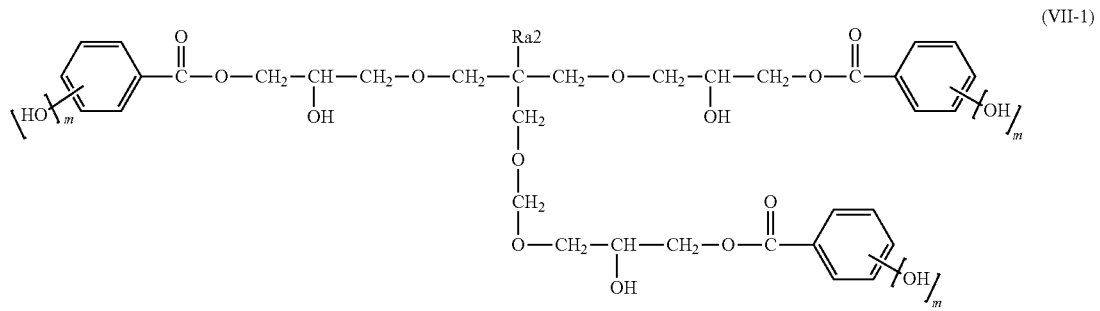

(VII-1)

In another embodiment of the above described positive working photosensitive compositions said glycidyl hydroxy benzoic acid condensate material comprises at least one compound having structure (VIIa-2), wherein Rw24 is OH or the moiety (VIIb-2), wherein ∿ represents the point of attachment in this moiety, provided that no more than one Rw24 is the moiety (VIIb-2). In this embodiment Ra2 is a $C_1$ to $C_5$ alkyl or a $C_2$ to $C_5$-alkylene-O-alkyl moiety.

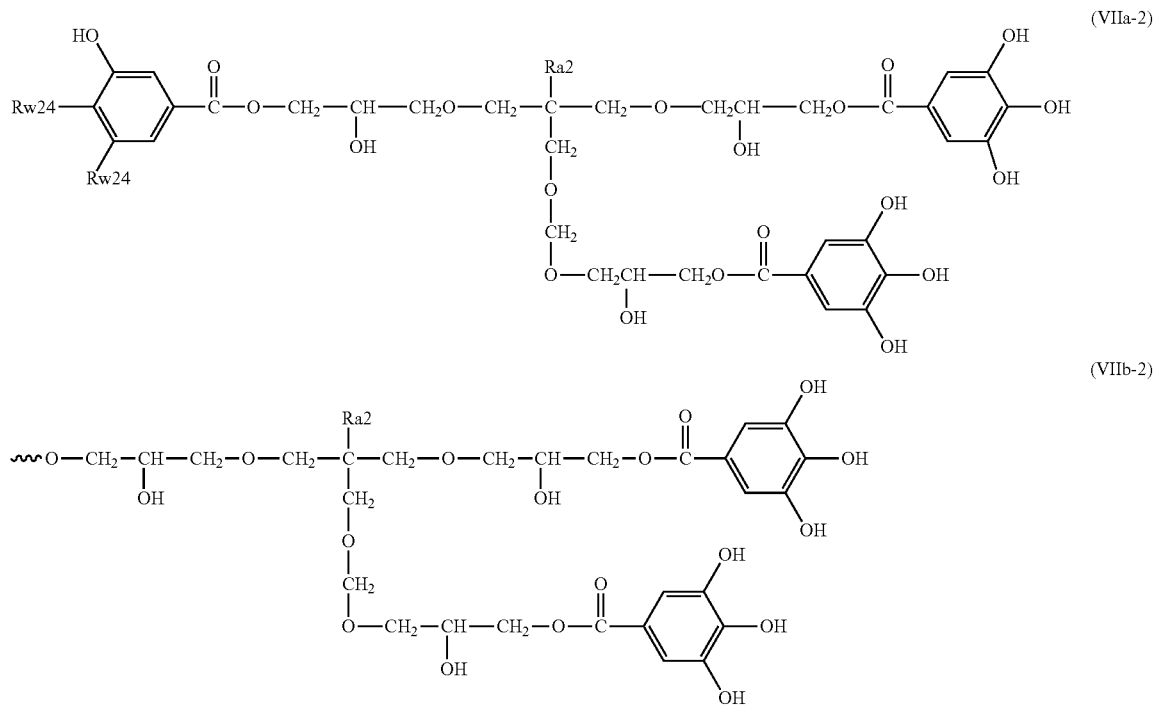

In another embodiment of the above described positive working photosensitive compositions said glycidyl hydroxy benzoic acid condensate material comprises at least one compound having structure (VII-2), wherein Ra2 is a $C_1$ to $C_5$ alkyl or a $C_2$ to $C_5$-alkylene-O-alkyl moiety.

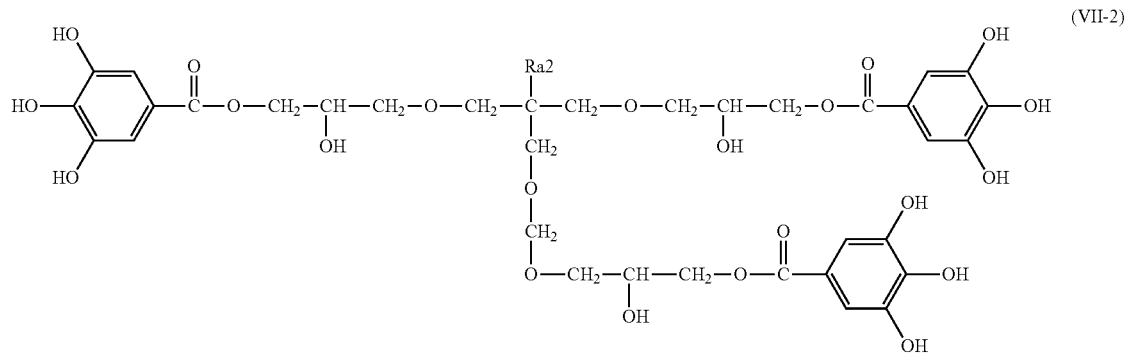

(VII-2)

In another embodiment of the above described positive working photosensitive compositions said glycidyl hydroxy benzoic acid condensate material comprises at least one compound having structure (VIIa-3), wherein Rw25 is OH or the moiety (VIIb-3), wherein ∼∼∼ represents the point of attachment in this moiety, provided that no more than one Rw25 is the moiety (VIIb-3). In this embodiment Ra2 is a $C_1$ to $C_5$ alkyl or a $C_2$ to $C_5$-alkylene-O-alkyl moiety.

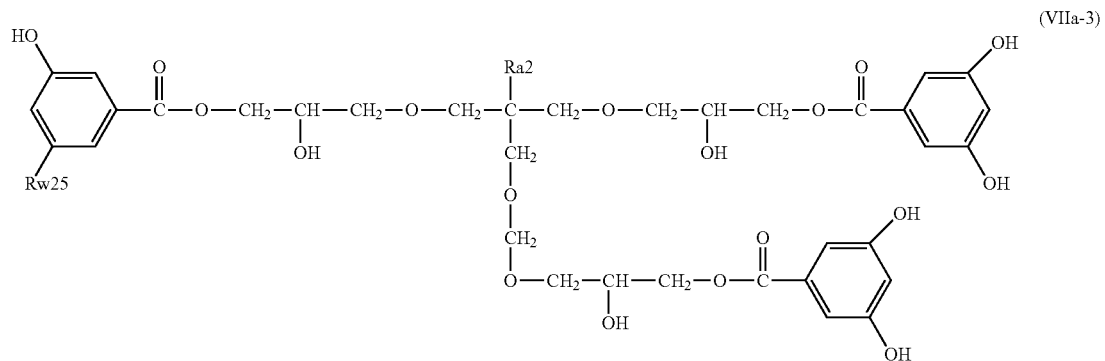

(VIIa-3)

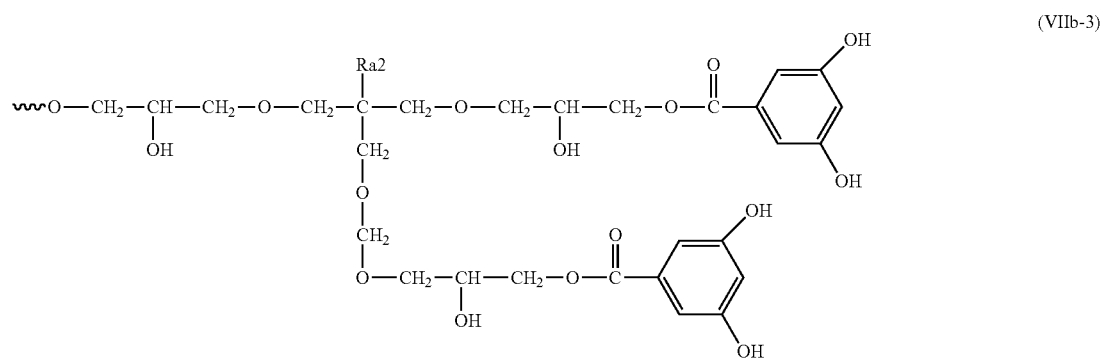

(VIIb-3)

In another embodiment of the above described positive working photosensitive compositions said glycidyl hydroxy benzoic acid condensate material comprises at least one compound having structure (VIIa-4), wherein Rw26 is OH or the moiety (VIIb-4), wherein ∼∼∼ represents the point of attachment in this moiety, provided that no more than one Rw26 is the moiety (VIIb-4). In this embodiment Ra2 is a $C_1$ to $C_5$ alkyl or a $C_2$ to $C_5$-alkylene-O-alkyl moiety.

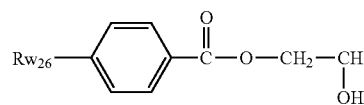
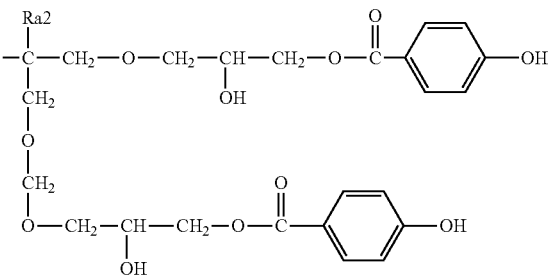
(VIIa-4)
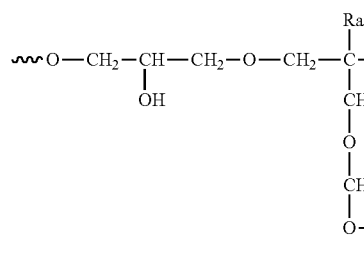
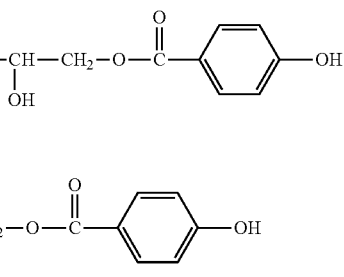
(VIIb-4)
In another embodiment of the above described positive working photosensitive compositions said glycidyl hydroxy benzoic acid condensate material comprises at least one compound selected from the group consisting of (VIII), (VIIIa), (VIIIb), (VIIIc), (VIIId) and (VIIIe).
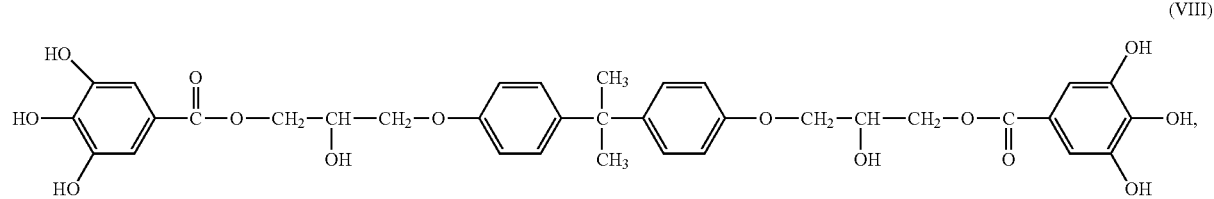
(VIII)
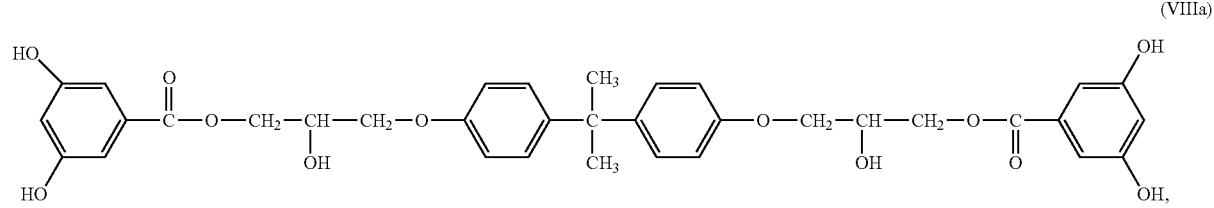
(VIIIa)
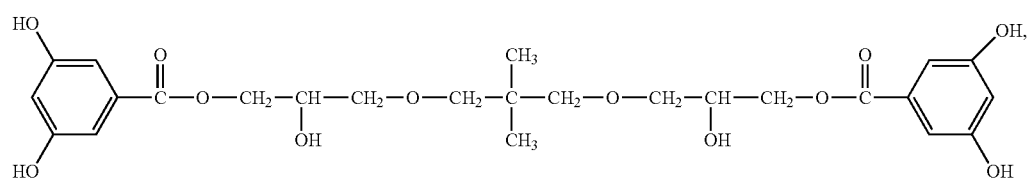
(VIIIb)

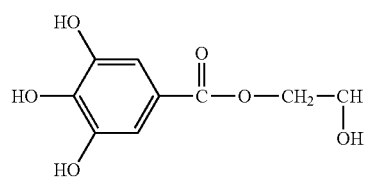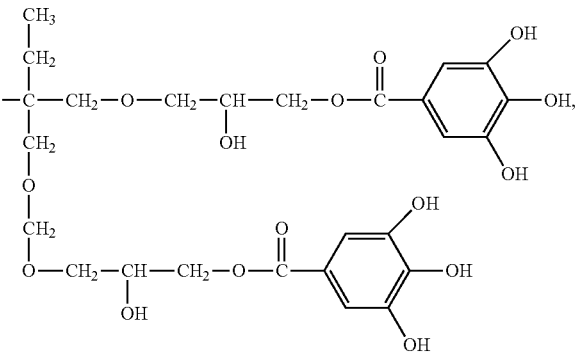

(VIIIc)

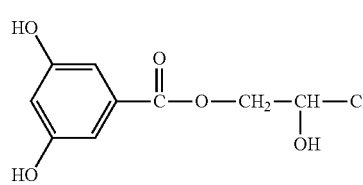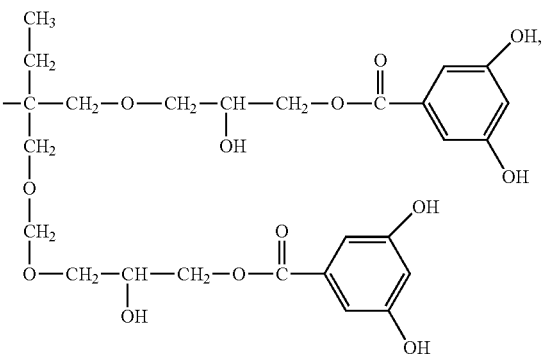

(VIIId)

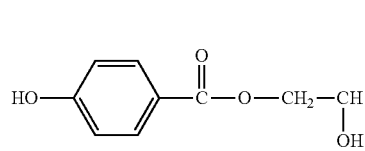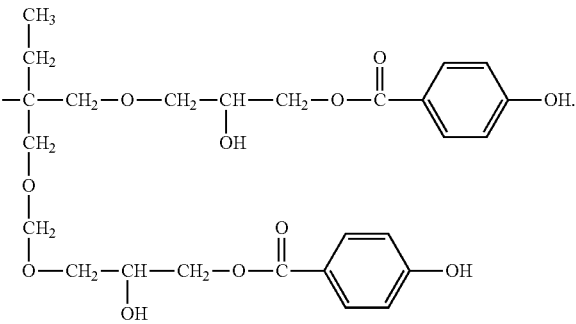

(VIIIe)

In another embodiment of the any of the above described positive working photosensitive compositions said component a) "at least one photoacid generator," is chosen from a variety of photoacid generators, such as onium salts, dicarboximidyl sulfonate esters (a.k.a. dicarboximide sulfonate esters or N-hydroxyamide sulfonate), oxime sulfonate esters, diazo(sulfonyl methyl) compounds(a.k.a. α,α-Bis (arylsulfonyl)diazomethanes, e.g. Ph-($SO_2$)—C(=$N_2$)— ($SO_2$)-Ph), disulfonyl methylene compounds (a.k.a. α,α-methylenedisulfone; e.g. Ph-($SO_2$)—$CH_2$—($SO_2$)-Ph) and disulfonyl hydrazine compounds (a.k.a. disulfonohydrazide PAGs, e.g. Ph-($SO_2$)—NH—NH—($SO_2$)-Ph)), nitrobenzyl sulfonate esters (e.g. 2-nitrobenzyl sulfonate ester derivatives), biimidazole compounds, diazomethane derivatives, glyoxime derivatives (e.g. $CH_3$—(C=N—O—$SO_2$-Ph)—(C=N—O—$SO_2$-Ph)-$CH_3$), β-ketosulfone derivatives (e.g. Ph-(C=O)—$CH_2$—$SO_2$-Ph), disulfone derivatives (e.g. Ph-$SO_2$—$SO_2$-Ph), sulfonic acid ester derivatives, imidoyl sulfonate derivatives (e.g. phthalimidyl triflate, phthalimidyl tosylate, 5-norbornene-2,3-dicarboxyimidoyl triflate, 5-norbornene-2,3-dicarboxyimidoyl tosylate and 5-norbornene-2,3-dicarboxylimidoyl n-butylsulfinate), diazonaphthoquinone sulfonate esters, halogenated triazine compounds or combinations thereof. The following publications show various examples of these different type of photoacid generators:

U.S. Pat. Nos. 6,042,988; 6,783,912; 6,908,722; "Evaluation of the standard addition method to determine rate constants for acid generation in chemically amplified photoresist at 157 nm," Adam R. Pawloski; Charles R. Szmanda; Paul F. Nealey, Proc. SPIE 4345, Advances in Resist Technology and Processing XVIII, Santa Clara CA, Feb. 25, 2001, Editor Francis Houlihan p 1056, Aug. 24, 2001; *"Chemically Amplification Resists for Microlithography,"* Hiroshi Ito, Adv. Polym. Sci. 172 p 37, 2005; "Chemical Amplification Mechanisms for Microlithography," E. Reichmanis et al., Chem. Mater. 13, 2305, 2001; *"i-Line sensitive Photoacid Generators for UV curring,"* Masumitsu Shirai et al, Progress in Organic coatings, 64, 175, 2009.

Onium salt photoacid generators may comprise, without limitation, alkyl sulfonate anions, substituted and unsubstituted aryl sulfonate anions, fluoroalkyl sulfonate anions, fluoarylalkyl sulfonate anions, fluorinated arylalkyl sulfonate anions, hexafluorophosphate anions, hexafluoroarsenate anions, hexafluoroantimonate anions, tetrafluoroborate anions, equivalents thereof or combinations thereof.

Specifically, without limitation, suitable photoacid generators may include triphenylsulfonium trifluoromethanesulfonate, triphenylsulfonium nonafluoro-n-butanesulfonate, triphenylsulfonium perfluoro-n-octanesulfonate, and triphenylsulfonium 2-(bicyclo[2.2.1]heptan-2-yl)-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-(bicyclo[2.2.1]heptan-2-yl)-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, and 4-methanesulfonylphenyldiphenylsulfonium 2-(bicyclo[2.2.1]heptan-2-yl)-1,1,2,2-tetrafluoroethanesulfonate, diphenyliodonium trifluoromethanesulfonate, diphenyliodonium nonafluoro-n-butanesulfonate, diphenyliodonium perfluoro-n-octanesulfonate, diphenyliodonium 2-(bicyclo[2.2.1]heptan-2-yl)-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-(bicyclo[2.2.1]heptan-2-yl)-1,1,2,2-tetrafluoroethanesulfonate, 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-(bicyclo[2.2.1]heptan-2-yl)-1,1,2,2-tetrafluoroethanesulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-(bicyclo[2.2.1]heptan-2-yl)-1,1,2,2-tetrafluoroethanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-(bicyclo[2.2.1]heptan-2-yl)-1,1,2,2-tetrafluoroethanesulfonate N-(trifluoromethanesulfonyloxy)bicyclo[2.2.1]hept-5-ene-2,3-dicarboximide, N-(nonafluoro-n-butanesulfonyloxy)bicyclo[2.2.1]hept-5-ene-2,3-dicarboximide, N-(perfluoro-n-octanesulfonyloxy)bicyclo[2.2.1]hept-5-ene-2,3-dicarboximide, N-[2-(bicyclo[2.2.1]heptan-2-yl)-1,1,2,2-tetrafluoroethanesulfonyloxy]bicyclo[2.2.1]hept-5-ene-2,3-dicarboximide, 1,3-dioxo-1H-benzo[de]isoquinolin-2(3H)-yl trifluoromethanesulfonate (naphthalene dicarboximidyl triflate), N-[2-(tetracyclo[4.4.0.1$^{2,5}$.1$^{7,10}$]dodecan-3-yl)-1,1-difluoroethanesulfonyloxy]bicyclo[2.2.1]hept-5-ene-2,3-dicarboximide, 1,3-dioxoisoindolin-2-yl trifluoromethanesulfonate, 1,3-dioxoisoindolin-2-yl nonafluoro-n-butane sulfonate, 1,3-dioxoisoindolin-2-yl perfluoro-n-octane sulfonate, 3-dioxoisoindolin-2-yl 2-(bicyclo[2.2.1]heptan-2-yl)-1,1,2,2-tetrafluoroethanesulfonate, 3-dioxoisoindolin-2-yl N-[2-(tetracyclo[4.4.0.1$^{2,5}$.1$^{7,10}$]dodecan-3-yl)-1,1-difluoroethanesulfonate, 1,3-dioxo-1H-benzo[de]isoquinolin-2(3H)-yl trifluoromethanesulfonate, 1,3-dioxo-1H-benzo[de]isoquinolin-2(3H)-yl nonafluoro-n-butane sulfonate, 1,3-dioxo-1H-benzo[de]isoquinolin-2(3H)-yl perfluoro-n-octanesulfonate, 1,3-dioxo-1H-benzo[de]isoquinolin-2(3H)-yl 2-(bicyclo[2.2.1]heptan-2-yl)-1,1,2,2-tetrafluoroethanesulfonate, or 1,3-dioxo-1H-benzo[de]isoquinolin-2(3H)-yl N-[2-(tetracyclo[4.4.0.1$^{2,5}$.1$^{7,10}$]dodecan-3-yl)-1,1-difluoroethanesulfonate, (E)-2-(4-methoxystyryl)-4,6-bis(trichloromethyl)-1,3,5-triazine, 2-(Methoxyphenyl)-4,6-bis-(trichloromethyl)-s-triazine, 2-[2-(Furan-2-yl)ethenyl]-4,6-bis(trichloromethyl)-s-triazine, 2-[2-(5-methylfuran-2-yl)ethenyl]-4,6-bis(trichloromethyl)-s-triazine, 2-[2-(3,4-Dimethoxyphenyl)ethenyl]-4,6-bis(trichloromethyl)-s-triazine, equivalents thereof or combinations thereof. Suitable photoacid generators may also include onium salts comprising anions and cations in combinations not shown supra.

In one embodiment of the above photoresist composition, said photoacid generator is chosen from ones which generates upon, upon 365 nm and/or broadband irradiation, a photo acid such as a sulfonic acid, such as alkylsulfonic acid, aryl sulfonic acid or fluoroalkylsulfonic acid, perfluorosulfonic acid, inorganic acid such as HAsF6, HSbF6, HPF6, or acid derived from tetraphenylborates, H(Ph)4B, or similar tetraarylborates, H(Aryl)4B. Non limiting examples of such PAG's are such photoacid generator include a variety of photoacid generators, such as onium salts, dicarboximidyl sulfonate esters, oxime sulfonate esters, diazo(sulfonyl methyl) compounds, disulfonyl methylene hydrazine compounds, nitrobenzyl sulfonate esters, biimidazole compounds, diazomethane derivatives, glyoxime derivatives, β-ketosulfone derivatives, disulfone derivatives, sulfonic acid ester derivatives, imidoyl sulfonate derivatives, diazonaphthoquinone sulfonate esters or combinations thereof. Such photoacid generators may inherently be sensitive to 365 nm and/or broadband radiation by appropriate substitution as known in the art. More specifically, these may, for instance, as non-limiting examples, be substituted or unsubstituted triarylsulfonium salts of organic sulfonic acids, wherein in the triarylsulfonium moiety or its corresponding acid the anion contains at least one aryl moiety which has a conjugated aryl, wherein the conjugated aryl moiety is either selected from a phenyl ring with at least one substituent selected from the aryloxy, alkyloxy, nitro, cyano, acetyl, aryl, alkenyl, alkoxyaryl (alkyl-O-aryl-), dialkoxyaryl ((alkyl-O—)2-aryl), or wherein the conjugated aryl moiety, alternatively, is a substituted or unsubstituted fused aromatic ring moiety containing 2 to 4 rings. Such substituents may be attached through a difunctional moiety capable of undergoing a resonance delocalization, such as arylene, including arylenes derived from a fused aromatic, or for example ethenylene (—C=C—) moieties. ethenyl (CH$_2$=CH—), phenylethenyl (Ph-CH=CH—), arylethynyl (Aryl-CH=CH—), and substituents containing ethenylenearylene moieties (e.g. Ar(—CH=CH—Ar—)$_z$ where z is 1-3. Specific non-limiting examples of substituted aryl and substituted aryl ethenyl substituent are as follows (3), (4) and (5):

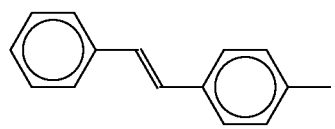

(3)

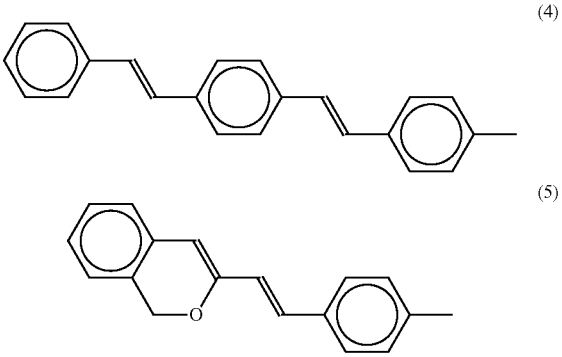

Other common PAG's sensitive to 365 nm and/or broadband radiation are substituted or unsubstituted 1,3-dioxo-1H-benzo[de]isoquinolin-2(3H)-yl ester organic sulfonic acids. FIG. 1 shows non-limiting examples of the above described PAG's. These PAG's may also have substituents as described above.

In another embodiment of this photoresist composition, the photoacid generator may also be one which is not directly sensitive to i-line or broadband radiation, but which has been sensitized to this radiation with photosensitizers that extend the effective wavelength and/or energy range. Such photosensitizers may be, without limitation, substituted and unsubstituted anthracenes, substituted and unsubstituted phenothiazines, substituted and unsubstituted perylenes, substituted and unsubstituted pyrenes, and aromatic carbonyl compounds, such as benzophenone and thioxanthone, fluorene, carbazole, indole, benzocarbazole, acridone chlorpromazine, equivalents thereof or combinations of any of the foregoing.

In another embodiment of the any of the above described positive working photosensitive compositions said component b) "at least one Novolak polymer;" is selected from Novolak polymers which comprise repeat units having bridges and phenolic compounds. Suitable phenol compounds include, without limitation, phenols, cresols, substituted and unsubstituted resorcinols, 2,5-xylenols, substituted and unsubstituted benzene triols and combinations thereof. Novolak polymers are produced, usually, with an acid catalyst, by condensation polymerization of phenolic compounds and aldehydes such as formaldehyde, acetaldehyde or substituted or unsubstituted benzaldehydes or condensation products of phenolic compounds and substituted or unsubstituted methylol compounds. Bridges described supra may comprise methylene groups or methyne groups. Novolak polymers can also be made as condensation products of ketones such as acetone, methyl ethyl ketone, acetophenone and the like. Catalysts may include Lewis acids, Brønstead acids, dicationic and tricationic metal ions and the like. For example, without limitation, aluminum chloride, calcium chloride, manganese chloride, oxalic acid, hydrochloric acid, sulfuric acid, methane sulfonic acid trifluoromethane sulfonic acid or combinations comprising any of the foregoing may be used.

Examples of suitable Novolak polymers include those obtained by the condensation reaction between a phenolic compound such as phenol, o-cresol, m-cresol, p-cresol, 2-5-xylenol and the like with an aldehyde compound such as formaldehyde in the presence of an acid or multivalent metal-ion catalyst. An exemplary weight average molecular weight for the alkali-soluble Novolak polymer may be in the range from 1,000 to 30,000 Daltons. A further exemplary weight average molecular weight may be from 1,000 to 20,000 Daltons. A still further exemplary weight average molecular weight may be from 1,500 to 10,000 Daltons. Exemplary bulk dissolution rates for Novolak polymers in 2.38% aqueous tetramethylammonium hydroxide are 10 Å/sec (Angstrom units per second) to 15,000 Å/sec. Further exemplary bulk dissolution rates are 100 Å/sec to 10,000 Å/sec. Still further exemplary bulk dissolution rates are 200 Å/sec to 5,000 Å/sec. A still further exemplary bulk dissolution rate of 1,000 Å/sec may be obtained from a single Novolak polymer or a blend of Novolak polymers, each comprising m-cresol repeat units.

Exemplary cresylic Novolak polymers may comprise, in cresol mole percentage terms, 0%-60% p-cresol, 0%-20% o-cresol, and 0%-80% m-cresol. Further exemplary cresylic Novolak polymers may comprise 0%-50% p-cresol, 0%-20% o-cresol, and 50%-100% m-cresol. Repeat units in Novolak polymers are defined by the composition of the polymer, so that, for example, p-cresol may be introduced by polymerization with an aldehyde or by dimethylol-p-cresol. Moreover, cresylic Novolak polymers may contain other phenolic compounds such as phenol, 2,5-xylenols, resorcinols, benzene triols and the like. Further, Novolak polymers can be branched or linear and may be blended to achieve a selected repeat unit mole percentage or dissolution rate. Bulk dissolution rates may be measured by the following procedure: (1) A 1-3 µm (micrometer) film of the Novolak resin is spin-coated from a solution on a silicon wafer and soft baked at 110° C. for 120 seconds on a contact hot plate. (2) The film thickness is measured using an optical method such as interferometry or ellipsometry or a mechanical profilometer. (3) The coated wafer is immersed in a solution of tetramethylammonium hydroxide (TMAH) developer and the time to dissolve completely the Novolak film ($t_c$) is detected visually or by means of optical interferometry (for example, a dissolution rate monitor). The bulk dissolution rate is calculated dividing the film thickness by $t_c$.

In another embodiment of the any of the above described positive working photosensitive compositions said component b) "at least one Novolak polymer;" is selected from a Novolak, polymer which comprises one or more cresylic repeat units chosen from o-cresol, p-cresol or m-cresol.

In another embodiment of the any of the above described positive working photosensitive compositions said component b) "at least one Novolak polymer;" is a cresylic Novolak comprising at least 80 mole percent m-cresol.

In another embodiment of the any of the above described positive working photosensitive compositions, this composition comprises only 1 Novolak polymer as part of said component b).

In another embodiment of the any of the above described positive working photosensitive compositions comprises 2 or more said Novolak polymers in component b).

As described above, Component c) said acrylate polymer, is one wherein in structure (I), $R_1$ to $R_6$ are, independently, —H, or —$CH_3$, A is a linear or branched $C_2$ to $C_{10}$ alkylene group, B is a $C_1$ to $C_{12}$ primary or secondary unsubstituted linear, branched, cyclic or alicyclic alkyl group, C is a $C_1$ to $C_{12}$ primary or secondary unsubstituted linear, branched, cyclic or alicyclic alkyl group, D is a linking group that is a direct valence bond, or a linear or branched $C_1$ to $C_{10}$, preferably $C_2$ to $C_{10}$ alkylene group, Ar is a substituted or unsubstituted aromatic group or heteroaromatic group, E is a linear or branched $C_2$ to $C_{10}$ alkylene group, G is an acid cleavable group, t is 0 mole % to about 40 mole %, v is 0 mole % to about 15 mole %, w is 0 mole % to about 45 mole %, x is 0 mole % to about 80 mole %, y is about 20 mole % to about 50 mole % and z is about 20 mole % to about 50 mole %, and further wherein the sum oft, v, w, x, y and z equals 100 mole %;

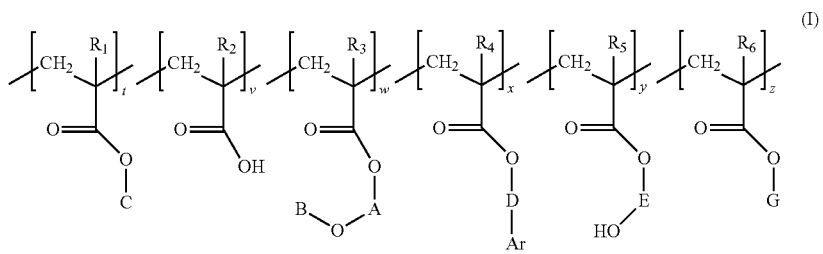

(I)

In another embodiment of any of the above described positive working photosensitive compositions, optionally, this structure (I) may contain other types of optional styrenic repeat units which have structure (Ia).

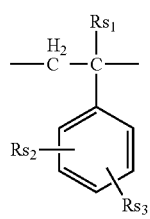

(Ia)

In structure (Ia), $Rs_1$ is chosen from H, Cl or $CH_3$ and $Rs_2$ and $Rs_3$ can be the same or different, and are chosen from H, OH, $OCOORs_4$, or $OCOCOORs_4$ (O—(C=O)—(C=O)—O-Rs4) and $Rs_4$ is an acid cleavable group. The polymer of the present invention may comprise (meth)acrylate units only or a mixture of (meth)acrylate and styrenic units. Acid labile groups may be present in the polymer. The polymer may comprise acid cleavable groups which may be esterified to a (meth)acrylate repeat unit via the carboxylate group or to a carbonate or oxylate group; which carbonate or oxylate group is, in turn, esterified to a phenol or an alcohol. For example, a monomer repeat unit, known in the art, is tert-butyl 4-vinylphenyl carbonate, in which a tert-butyl carbonate is esterified to 4-hydroxystyrene. Acid cleavable groups may include, without limitation, a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a 3-oxocyclohexyl group, a 2-methyl-2-adamantyl group, a 2-ethyl-2-adamantyl group, a 8-methyl-8-tricyclo[5.2.1.0 2,6]decyl group, a 1,2,7,7-tetramethyl-2-norbornyl group, a 2-acetoxymethyl group, a 2-hydroxymethyl group a 1-methyl-1-cyclohexylethyl group, a 4-methyl-2-oxotetrahydro-2H-pyran-4-yl group, a 2,3-dimethylbutan-2-yl group, a 2,3,3-trimethylbutan-2-yl group, a 1-methyl cyclopentyl group, a 1-ethyl cyclopentyl group, a 1-methyl cyclohexyl group, 1-ethyl cyclohexyl group, a 1,2,3,3-tetramethylbicyclo[2.2.1]heptan-2-yl group, a 2-ethyl-1,3,3-trimethylbicyclo[2.2.1]heptan-2-yl group, a 2,6,6-trimethylbicyclo[3.1.1]heptan-2-yl group, a 2,3-dimethylpentan-3-yl group, or a 3-ethyl-2-methylpentan-3-yl group. A monomer repeat unit with an acid cleavable group is said to be protected. Polymers may be fully protected, partially protected, partially deprotected or fully deprotected. Deprotection may occur, for example, during or after exposure of the photosensitive composition when photogenerated acid is present.

In another embodiment of any of the above described positive working photosensitive compositions, optionally, this structure (I), may contain other types of optional (meth) acrylate derived repeat, that impart additional etching resistance, modify the dissolution characteristics of the polymer in its protected, partially protected, partially deprotected or fully deprotected forms, modify photosensitivity, modify adhesion, provide a bound photoacid generator or impart other useful characteristics. Such (meth)acrylate derived repeat units may include, without limitation, certain chemical functionalities comprised within pendant groups on the meth(acrylate) derived repeat unit such as lactones, anhydrides, phenols, alcohols, carboxylic acids, substituted and unsubstituted benzyl groups, ethers, alicyclic esters, ester alcohols, ester ethers, aliphatic esters, aromatic esters and the like.

In another embodiment of the above described positive working photosensitive compositions said component c), said acrylate polymer, is one which only consists of the repeat units as described in structure (I).

In addition to optional styrenic units are ones which have structure (Ia).

Optionally, structure (I) may contain other types of optional styrenic repeat units.

Non-limiting examples of these optional styrenic units are ones which have structure (Ia).

In accordance with the above embodiments, at least one acrylate polymer, comprising a component having structure (I), may be synthesized using one or more feeds of the indicated monomers. At least some of the monomers may be introduced at the beginning of the polymerization reaction in whole or in part. Further, monomer feeds may be accomplished at selected feed rates during the reaction to accommodate different monomer co-reactivities or to control other polymer properties such as molecular weight or solubility. Polymerization may be initiated by free radical initiators, cationic polymerization initiators, anionic polymerization initiators or chelating catalysts.

In another embodiment of the any of the above described positive working photosensitive compositions said component c), said acrylate polymer, is one wherein A said linear or branched $C_2$ to $C_{10}$ alkylene group, is selected from without limitation, from ethylene, 1,2-propylene, 1,3-propylene or the like. Exemplary groups for B may be, without limitation, methyl, ethyl, propyl, isopropyl, butyl, isobutyl or the like. Exemplary groups for E may be, without limitation, ethylene, 1,2-propylene, 1,3-propylene or the like.

In another embodiment of the any of the above described positive working photosensitive compositions said component c), said acrylate polymer, is one wherein B, said $C_1$ to $C_{12}$ primary or secondary unsubstituted linear, branched, cyclic or alicyclic alkyl group, is selected from methyl, ethyl, propyl, butyl, isopropyl, isobutyl, cyclopropyl, cyclobutyl, cyclopentyl, cyclohexyl, norbornyl, tetrahydrodicyclopentadienyl, adamantyl, and the like.

In another embodiment of the any of the above described positive working photosensitive compositions said component c), said acrylate polymer, is one wherein C, a $C_1$ to $C_{12}$ primary or secondary unsubstituted linear, branched, cyclic or alicyclic alkyl group, is selected from methyl, ethyl, propyl, butyl, isopropyl, isobutyl, cyclopropyl, cyclobutyl, cyclopentyl, cyclohexyl, norbornyl, tetrahydrodicyclopentadienyl and the like.

In another embodiment of the any of the above described positive working photosensitive compositions said component c), said acrylate polymer, is one wherein D, $C_1$ to $C_{12}$ primary or secondary unsubstituted linear, branched, cyclic or alicyclic alkyl group, is selected from methyl, ethyl, propyl, butyl, isopropyl, isobutyl, cyclopropyl, cyclobutyl, cyclopentyl, cyclohexyl, norbornyl, tetrahydrodicyclopentadienyl and the like. In another embodiment of the any of the above described positive working photosensitive compositions said component c), said acrylate polymer, is one wherein E, a is a linear or branched $C_2$ to $C_{10}$ alkylene group, is selected from ethylene, 1,2-propylene, 1,3-propylene and the like.

In another embodiment of the any of the above described positive working photosensitive compositions said component c), said acrylate polymer, is one wherein A is a methylene group, an ethylene group or a 1,2-propylene group, B is a methyl group, an ethyl group, a propyl group, or a butyl group, C is a methyl group, an ethyl group, a propyl group, a butyl group, a cyclohexyl group, an isobornyl group or a tetrahydrodicyclopentadienyl group, D is a direct valence bond, a methylene or an ethylene group, E is a methylene group, an ethylene group or a 1,2-propylene group.

In another embodiment of the any of the above described positive working photosensitive compositions said component c), said acrylate polymer, is one wherein, said acrylate polymer in one wherein G is a high activation energy acid labile group selected from a tertiary alkyl which has at least one vicinal hydrogen to the tertiary attachment point of the oxygen of the carboxylate in the repeat unit designated by z forming a tertiary ester, or a low activation energy protection group selected from an acetal or ketal formed with the oxygen of the carboxylate in the repeat unit designated by z.

In another embodiment of the any of the above described positive working photosensitive compositions said component c), said acrylate polymer, is one wherein G is an acid cleavable group chosen from a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a 3-oxocyclohexyl group, a 2-methyl-2-adamantyl group, a 2-ethyl-2-adamantyl group, a 8-methyl-8-tricyclo[5.2.1.0 2,6]decyl group, a 1,2,7,7-tetramethyl-2-norbornyl group, a 2-acetoxymethyl group, a 2-hydroxymethyl group a 1-methyl-1-cyclohexylethyl group, a 4-methyl-2-oxotetrahydro-2H-pyran-4-yl group, a 2,3-dimethylbutan-2-yl group, a 2,3,3-trimethylbutan-2-yl group, a 1-methyl cyclopentyl group, a 1-ethyl cyclopentyl group, a 1-methyl cyclohexyl group, 1-ethyl cyclohexyl group, a 1,2,3,3-tetramethylbicyclo[2.2.1]heptan-2-yl group, a 2-ethyl-1,3,3-trimethylbicyclo[2.2.1]heptan-2-yl group, a 2,6,6-trimethylbicyclo[3.1.1]heptan-2-yl group, a 2,3-dimethylpentan-3-yl group, or a 3-ethyl-2-methylpentan-3-yl group.

In another embodiment of the any of the above described positive working photosensitive compositions said component c), said acrylate polymer, is one wherein t is 0 mole %, v is about 2 mole % to about 15 mole %, w is 0 mole %, x is about 5 mole % to about 30 mole %, y is about 20 mole % to about 45 mole %, and z is about 20 mole % to about 45 mole %, $R_2$ is methyl, $R_4$ and $R_5$ are methyl, and $R_6$ is H.

In another embodiment of the any of the above described positive working photosensitive compositions said component c), said acrylate polymer, is one wherein D is methylene, Ar is Phenyl, E is a —$CH_2$—$CH(CH_3)$— group, wherein the —$CH_2$— part of this group is attached to the carboxylate oxygen of the repeat unit designated by y, and G is a tert-butyl group.

In another embodiment of the any of the above described positive working photosensitive compositions said component c), said acrylate polymer, is one wherein t is 0 mole %, v is about 2 mole % to about 15 mole %, w is about 5 mole % to about 20 mole %, x is about 5 mole % to about 50 mole %, y is about 20 mole % to about 45 mole %, and z is about 20 mole % to about 45 mole %, $R_2$ and $R_3$ are H and $R_3$, $R_4$ and $R_6$ are methyl.

In another embodiment of the any of the above described positive working photosensitive compositions said component c), said acrylate polymer, is one wherein A is an ethylene group, B is methyl, D is methylene, Ar is Phenyl, E is a —$CH_2$—$CH(CH_3)$— group wherein the —$CH_2$— part of this group is attached to the carboxylate oxygen of the repeat unit designated by y, and G is a tert-butyl group or a 1-ethylcyclopentyl group.

In another embodiment of the any of the above described positive working photosensitive compositions said component c), said acrylate polymer is one wherein t is about 5 mole % to about 30 mole %, v is about 2 mole % to about 15 mole %, w is 0 mole %, x is 0 mole %, y is about 20 mole % to about 45 mole %, and z is about 20 mole % to about 45 mole %, $R_1$ is methyl, $R_2$ is H, $R_5$ and $R_6$ are methyl.

In another embodiment of the any of the above described positive working photosensitive compositions said component c), said acrylate polymer, is one wherein C is methyl, E is a —$CH_2$—$CH(CH_3)$— group wherein the —$CH_2$— part of this group is attached to the carboxylate oxygen of the repeat unit designated by y, and G is a tert-butyl group or a 1-ethylcyclopentyl group.

In another embodiment of the any of the above described positive working photosensitive compositions said component c), said acrylate polymer is one wherein t is about 5 mole % to about 30 mole %, v is about 2 mole % to about 15 mole %, w is 0 mole %, x is about 10 mole % to about 30 mole %, y is about 20 mole % to about 45 mole %, and z is about 20 mole % to about 45 mole %, $R_1$, $R_2$, $R_4$ and $R_5$, are methyl, and $R_6$ is H.

In another embodiment of the any of the above described positive working photosensitive compositions said component c), said acrylate polymer, is one wherein C is isobornyl, or tetrahydrodicyclopentadienyl, E is a —$CH_2$—$CH (CH_3)$— group wherein the —$CH_2$— part of this group is attached to the carboxylate oxygen of the repeat unit designated by y, and G is a tert-butyl group or a 1-ethylcyclopentyl group.

In another embodiment of the any of the above described positive working photosensitive compositions said component c), said acrylate polymer is one wherein t is 0 mole %, v is 0 mole %, w is about 5 mole % to about 20 mole %, x is about 5 mole % to about 30 mole %, y is about 20 mole % to about 45 mole %, and z is about 20 mole % to about 45 mole %, $R_3$ is H, $R_4$, $R_5$ and $R_6$ are methyl.

In another embodiment of the any of the above described positive working photosensitive compositions said component c), said acrylate polymer, is one wherein A is an ethylene group, B is methyl, D is methylene, Ar is Phenyl, E is a —CH₂—CH(CH₃)— group wherein the —CH₂— part of this group is attached to the carboxylate oxygen of the repeat unit designated by y, and G is a tert-butyl group or a 1-ethylcyclopentyl group.

In another embodiment of the any of the above described positive working photosensitive compositions said component c), is comprised of said acrylate polymer comprising structure (I) which has an Mw as measured by GPC (using polystyrene standards) which may, without limitation, range from 800 Daltons to 30,000 Daltons. Further exemplary weight average molecular weights of the structure (I) may, without limitation, range from 1,500 Daltons to 20,000 Daltons. Still further exemplary weight average molecular weights of the structure (I) may, without limitation, range from 2,500 Daltons to 20,000 Daltons.

In another embodiment of the any of the above described positive working photosensitive compositions said component c), is comprised of said acrylate polymer comprising structure (I) which has a polydispersity (Mw/Mn) as measured by GPC (using polystyrene standards) ranging between 1 and about 2.5. In another aspect of this embodiment the polydispersity may range from about 1.3 to about 2.5. In yet another aspect of this embodiment the polydispersity may range from about 1.5 to about 2.3.

In another embodiment of the any of the above described positive working photosensitive compositions said component e), which is comprised of at least one heterocyclic thiol compound comprising a ring structure chosen from the general structures (III), (IIIa) or (IIIb), or tautomers thereof; may include, without limitation, substituted or unsubstituted triazole thiols, substituted or unsubstituted imidazole thiols, substituted or unsubstituted triazine thiols, substituted or unsubstituted mercapto pyrimidines, substituted or unsubstituted thiadiazole-thiols, substituted or unsubstituted indazole thiols, tautomers thereof or combinations thereof. Substituents may include, without limitation, saturated or unsaturated hydrocarbon groups, substituted or unsubstituted aromatic rings, aliphatic, aromatic or heteroaromatic alcohols, amines, amides, imides carboxylic acids, esters, ethers, halides, and the like. Such substituents may be used in concert with the heterocyclic thiol to improve solubility, to modify interaction with the substrate, to enhance exposure to light or to act as an annihilation dye.

In another embodiment of the any of the above described positive working photosensitive compositions said component e), such heterocyclic thiols may include, without limitation the following compounds (VIV to VIVp) in unsubstituted or substituted form:

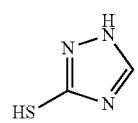

1H-1,2,4-triazole-3-thiol
(VIV)

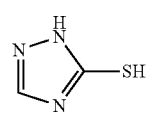

1H-1,2,4-triazole-5-thiol
(VIVa)

-continued

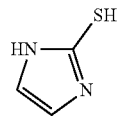

1H-imidazole-2-thiol
(VIVb)

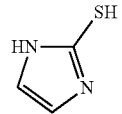

1H-imidazole-2-thiol
(VIVc)

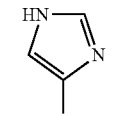

1H-imidazole-4-thiol
(VIVd)

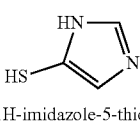

1H-imidazole-5-thiol
(VIVe)

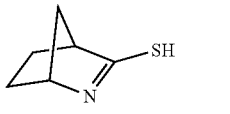

2-azabicyclo[2.2.1]hept-2-ene-3-thiol
(VIVf)

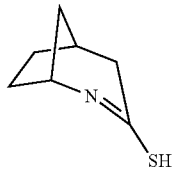

2-azabicyclo[3.2.1]oct-2-ene-3-thiol
(VIVg)

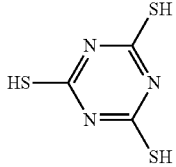

1,3,5-triazine-2,4,6-trithiol
(VIVh)

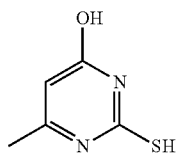

2-mercapto-6-methylpyrimidin-4-ol
(VIVi)

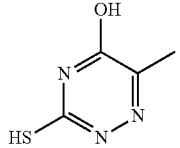

3-mercapto-6-methyl-1,2,4-traizin-5-ol
(VIVj)

-continued

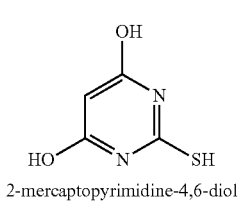
2-mercaptopyrimidine-4,6-diol (VIVk)

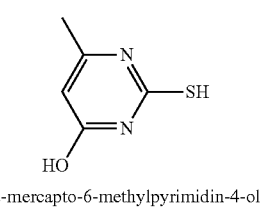
2-mercapto-6-methylpyrimidin-4-ol (VIVl)

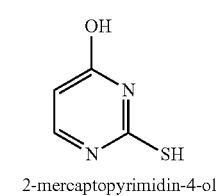
2-mercaptopyrimidin-4-ol (VIVm)

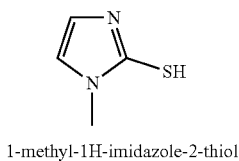
1-methyl-1H-imidazole-2-thiol (VIVn)

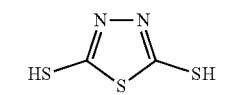
1,3,4-thiadiazole-2,5-dithiol (VIVo)

1H-indazole-3-thiol (VIVp)

In another embodiment of the any of the above described positive working photosensitive compositions said component e), such heterocyclic thiols may include thiouracil derivatives such as 2-thiouracil are further examples. These include, without limitation, 5-methyl-2-thiouracil, 5,6-dimethyl-2-thiouracil, 6-ethyl-5-methyl-2-thiouracil, 6-methyl-5-n-propyl-2-thiouracil, 5-ethyl-2-thiouracil, 5-n-propyl-2-thiouracil, 5-n-butyl-2-thiouracil, 5-n-hexyl-2-thiouracil, 5-n-butyl-6-ethyl-2-thiouracil, 5-hydroxy-2-thiouracil, 5,6-dihydroxy-2-thiouracil, 5-hydroxy-6-n-propyl-2-thiouracil, 5-methoxy-2-thiouracil, 5-n-butoxy-2-thiouracil, 5-methoxy-6-n-propyl-2-thiouracil, 5-bromo-2-thiouracil, 5-chloro-2-thiouracil, 5-fluoro-2-thiouracil, 5-amino-2-thiouracil, 5-amino-6-methyl-2-thiouracil, 5-amino-6-phenyl-2-thiouracil, 5,6-diamino-2-thiouracil, 5-allyl-2-thiouracil, 5-allyl-3-ethyl-2-thiouracil, 5-allyl-6-phenyl-2-thiouracil, 5-benzyl-2-thiouracil, 5-benzyl-6-methyl-2-thiouracil, 5-acetamido-2-thiouracil, 6-methyl-5-nitro-2-thiouracil, 6-amino-2-thiouracil, 6-amino-5-methyl-2-thiouracil, 6-amino-5-n-propyl-2-thiouracil, 6-bromo-2-thiouracil, 6-chloro-2-thiouracil, 6-fluoro-2-thiouracil, 6-bromo-5-methyl-2-thiouracil, 6-hydroxy-2-thiouracil, 6-acetamido-2-thiouracil, 6-n-octyl-2-thiouracil, 6-dodecyl-2-thiouracil, 6-tetradodecyl-2-thiouracil, 6-hexadecyl-2-thiouracil, 6-(2-hydroxyethyl)-2-thiouracil, 6-(3-isopropyloctyl)-5-methyl-2-thiouracil, 6-(m-nitrophenyl)-2-thiouracil, 6-(m-nitrophenyl)-5-n-propyl-2-thiouracil, 6-α-naphthyl-2-thiouracil, 6-α-naphthyl-5-t-butyl-2-thiouracil, 6-(p-chlorophenyl)-2-thiouracil, 6-(p-chlorophenyl)-2-ethyl-2-thiouracil, 5-ethyl-6-eicosyl-2-thiouracil, 6-acetamido-5-ethyl-2-thiouracil, 6-eicosyl-5-allyl-2-thiouracil, 5-amino-6-phenyl-2-thiouracil, 5-amino-6-(p-chlorophenyl)-2-thiouracil, 5-methoxy-6-phenyl-2-thiouracil, 5-ethyl-6-(3,3-dimethyloctyl)-2-thiouracil, 6-(2-bromoethyl)-2-thiouracil.

In another embodiment of the above described positive working photosensitive compositions, said component e), the heterocyclic thiol component is selected from a group consisting of unsubstituted triazole thiol, substituted triazole thiol, unsubstituted imidazole thiol, substituted imidazole thiol, substituted triazine thiol, unsubstituted triazine thiol, a substituted mercapto pyrimidine, unsubstituted mercapto pyrimidine, a substituted thiadiazole-thiol, unsubstituted thiadiazole-thiol, substituted indazole thiol, unsubstituted indazole thiol, tautomers thereof, and combinations thereof.

In another embodiment of the above described positive working photosensitive compositions said component e), the heterocyclic thiol is selected from a group consisting of 1,3,5-triazine-2,4,6-trithiol, 2-mercapto-6-methylpyrimidin-4-ol, 3-mercapto-6-methyl-1,2,4-triazin-5-ol, 2-mercaptopyrimidine-4,6-diol, 1H-1,2,4-triazole-3-thiol, 1H-1,2,4-triazole-5-thiol, 1H-imidazole-2-thiol, 1H-imidazole-5-thiol, 1H-imidazole-4-thiol, 2-azabicyclo[3.2.1]oct-2-ene-3-thiol, 2-azabicyclo[2.2.1]hept-2-ene-3-thiol, 1H-benzo[d]imidazole-2-thiol, 2-mercapto-6-methylpyrimidin-4-ol, 2-mercaptopyrimidin-4-ol, 1-methyl-1H-imidazole-2-thiol, 1,3,4-thiadiazole-2,5-dithiol, 1H-indazole-3-thiol, tautomers thereof and combinations thereof.

In another embodiment of the any of the above described positive working photosensitive compositions an optional basic quencher may be present. In one aspect of this embodiment said basic quencher may be selected from an amine, or a tetraalkylammonium carboxylate salt. In another aspect of this embodiment, said basic quencher is selected from amine. In another aspect of this embodiment said basic quencher is a tetraalkylammonium carboxylate salt.

In one embodiment of the above described positive working photosensitive compositions, when an optional basic quencher is present and is an amine, this amine may be selected from an amine compound or a mixture of amine compounds having a boiling point above 100° C., at atmospheric pressure, and a $pK_a$ of at least 1. In another aspect of this embodiment said amine quencher, is either selected from the group consisting of compounds having structures (Xa), (Xb), (Xc) (Xd), (Xe), (Xf), (Xg), (Xh), (Xi) and (Xj), or a mixture of compounds from this group; wherein $R_{b1}$ is C-1 to C-20 saturated alkyl chain or a C-2 to C-20 unsaturated alkyl chain; $R_{b2}$, $R_{b3}$, $R_{b4}$, $R_{b5}$, $R_{b6}$, $R_{b7}$, $R_{b8}$, $R_{b9}$, $R_{b10}$, $R_{b11}$, $R_{b12}$, and $R_{b13}$, are independently selected from the group consisting of H, and a C-1 to C-1 to C-20 alkyl.

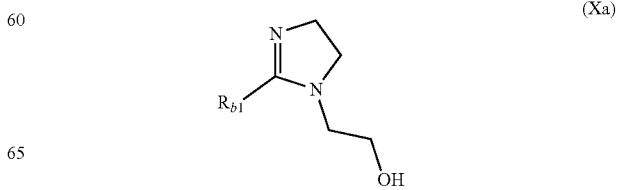
(Xa)

-continued

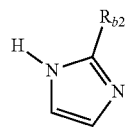
(Xb)

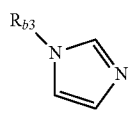
(Xc)

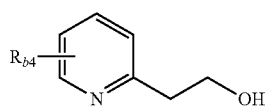
(Xd)

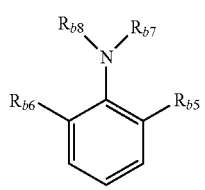
(Xe)

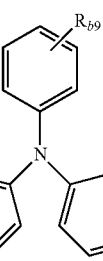
(Xf)

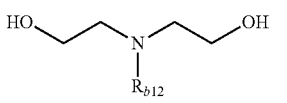
(Xe)

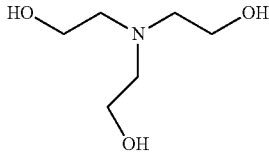
(Xf)

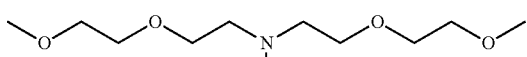
(Xg)

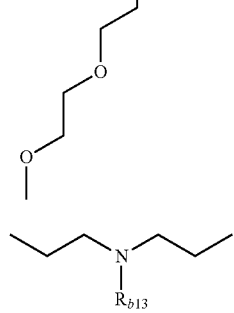
(Xh)

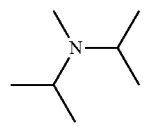
(Xi)

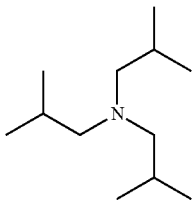
(Xj)

In one embodiment of the above described positive working photosensitive compositions, when an optional basic quencher is present and is a tetraalkylammonium carboxylate salt, this salt may be that of a mono functional aliphatic carboxylic acid or a bis[tetraalkylammonium] salt of an aliphatic dicarboxylic acid. In one aspect of this embodiment the basic quencher is a carboxylate salt of a mono functional aliphatic carboxylic acid. In another aspect of this embodiment the basic quencher is a bis[tetraalkylammonium] salt of an aliphatic dicarboxylic acid.

In one embodiment of the above described positive working photosensitive compositions, when an optional basic quencher is present and is a tetraalkylammonium salt of an aliphatic mono functional carboxylic acid it may be selected from the salts wherein the tetraalkylammonium moiety is selected from tetramethylammonium, tetraethylammonium, tetrapropylammonium, tetrabutylammonium, tetrapentylammonium, tetrahexylammonium, tetraheptylammonium, tetraoctylammonium, benzyltrimethylammonium, benzyltriethylammonium, benzyltripropylammonium, benzyltributylammonium and the carboxylate moiety may be selected from formate, acetate, propionate, butyrate, pentanoate, hexanoate, heptanoate, octanoate, cyclohexanecarboxylate, and the like. In one aspect of this embodiment said tetraalkylammonium salt of an aliphatic carboxylic acid is selected from the salts wherein the tetraalkylammonium moiety is selected from tetramethylammonium, tetraethylammonium, tetrapropylammonium, tetrabutylammonium, tetrapentylammonium, and benzyltrimethylammonium, and the aliphatic carboxylate is selected from acetate, propionate, butyrate, pentanoate and cyclohexylcarboxyate.

In one embodiment of the above described positive working photosensitive compositions, when an optional basic quencher is present and is a bis[tetraalkylammonium] salt of an aliphatic dicarboxylic acid, non-limiting examples of such salts are ones wherein the bis[tetraalkylammonium] moiety is selected from bis[tetramethylammonium], bis[tetraethylammonium], bis[tetrapropylammonium], bis[tetrabutylammonium], bis[tetrapentylammonium], bis[tetrahexylammonium], bis[tetraheptylammonium], bis[tetraoctylammonium], bis-[benzyltrimethylammonium], bis-[benzyltripropylammonium], bis-[benzyltributylammonium] and the like; and wherein the aliphatic dicarboxylate moiety may be chose from oxalate, malonate, succinate, adipate, heptadienoate, octanedioate, nonanedioate, fumarate, maleate, gluconate, itaconate, and the like. In one aspect of this embodiment said bis[tetraalkylammonium] salt of an aliphatic dicarboxylic acid is selected from the salts wherein the bis[tetraalkylammonium] moiety is selected from bis[tetramethylammonium], bis[tetraethylammonium], bis[tetrapropylammonium], bis[tetrabutylammonium], bis[tetrapentylammonium], and bis[benzyltrimethylammonium], and the aliphatic dicarboxylate is selected from oxalate, malonate, succinate, adipate, and heptadienoate.

In one embodiment of the above described positive working photosensitive compositions, when an optional basic quencher is present and is a bis[tetraalkylammonium]oxalate.

In one embodiment of the above described positive working photosensitive compositions, when an optional basic quencher is present and is a bis[tetraalkylammonium] salt of an aliphatic dicarboxylic acid it is selected from the salts wherein the bis[tetraalkylammonium] moiety is selected from bis[tetramethylammonium], bis[tetraethylammonium], bis[tetrapropylammonium], bis[tetrabutylammonium], bis[tetrapentylammonium], and bis[benzyltrimethylammonium], and the dicarboxylate is oxalate.

In another embodiment of the any of the above described positive working photosensitive compositions, herein, the solvent component f) may be chosen from the following non-limiting examples of suitable organic solvents: butyl acetate, amyl acetate, cyclohexyl acetate, 3-methoxybutyl acetate (MBA), methyl ethyl ketone, methyl amyl ketone, cyclohexanone, cyclopentanone, ethyl-3-ethoxy propanoate, methyl-3-ethoxy propanoate, methyl-3-methoxy propanoate, methyl acetoacetate, ethyl acetoacetate, diacetone alcohol, methyl pivalate, ethyl pivalate, propylene glycol monomethyl ether (a.k.a. 1-methoxypropan-2-ol) (PGME), propylene glycol monoethyl ether, propylene glycol monomethyl ether acetate (a.k.a. 1-methoxy-2-propanyl acetate) (PGMEA), propylene glycol propyl ether acetate, propylene glycol monoethyl ether propanoate, ethylene glycol monomethyl ether, ethylene glycol monoethyl ether, diethylene glycol monomethyl ether, diethylene glycol monoethyl ether, 3-methyl-3-methoxybutanol, N-methyl-2-pyrrolidone, anisole, dimethyl sulfoxide, gamma-butyrolactone, methyl lactate, ethyl lactate, propyl lactate, tetramethylene sulfone, propylene glycol dimethyl ether, dipropylene glycol dimethyl ether, ethylene glycol dimethyl ether or diethylene glycol dimethyl ether, gamma butyrolactone. These solvents may be used singly or in a mixture of two or more. In another aspect of this embodiment said solvent component f) is selected from butyl acetate, amyl acetate, cyclohexyl acetate, 3-methoxybutyl acetate, methyl ethyl ketone, methyl amyl ketone, cyclohexanone, ethyl-3-ethoxy propanoate, methyl-3-ethoxy propanoate, methyl-3-methoxy propanoate, propylene glycol monomethyl ether (a.k.a. 1-methoxypropan-2-ol) (PGME), propylene glycol monoethyl ether, propylene glycol monomethyl ether acetate (a.k.a. 1-methoxy-2-propanyl acetate) (PGMEA), propylene glycol monoethyl ether propanoate, methyl lactate, ethyl lactate, propylene glycol dimethyl ether. In another aspect of this embodiment said solvent component f) is propylene glycol monomethyl ether acetate (a.k.a. 1-methoxy-2-propanyl acetate) (PGMEA) or a mixture of propylene glycol monomethyl ether acetate and 3-methoxybutyl acetate.

Other optional additives, which have compatibility with and can be added to the composition disclosed and claimed herein according to need, include auxiliary resins, plasticizers, surface leveling agents and stabilizers to improve the properties of the resist layer, coloring agents to increase the visibility of the patterned resist layer formed by development, annihilation dyes, tetraalkylammonium salts such as tetrabutylammonium oxalate and the like.

Surface leveling agents may include surfactants. There is no particular restriction with regard to the surfactant, and the examples of it include a polyoxyethylene alkyl ether such as polyoxyethylene lauryl ether, polyoxyethylene stearyl ether, polyoxyethylene cetyl ether, and polyoxyethylene olean ether; a polyoxyethylene alkylaryl ether such as polyoxyethylene octylphenol ether and polyoxyethylene nonylphenol ether; a polyoxyethylene polyoxypropylene block copolymer; a sorbitane fatty acid ester such as sorbitane monolaurate, sorbitane monopalmitate, and sorbitane monostearate; a nonionic surfactant of a polyoxyethylene sorbitane fatty acid ester such as polyoxyethylene sorbitane monolaurate, polyoxyethylene sorbitane monopalmitate, polyoxyethylene sorbitane monostearate, polyethylene sorbitane trioleate, and polyoxyethylene sorbitane tristearate; a fluorinated surfactant such as F-Top EF301, EF303, and EF352 (manufactured by Jemco Inc.), Megafac F171, F172, F173, R08, R30, R90, and R94 (manufactured by Dainippon Ink & Chemicals, Inc.), Florad FC-430, FC-431, FC-4430, and FC-4432 (manufactured by Sumitomo 3M Ltd.), Asahi Guard AG710, Surflon S-381, S-382, S-386, SC101, SC102, SC103, SC104, SC105, SC106, Surfinol E1004, KH-10, KH-20, KH-30, and KH-40 (manufactured by Asahi Glass Co., Ltd.); an organosiloxane polymer such as KP-341, X-70-092, and X-70-093 (manufactured by Shin-Etsu Chemical Co., Ltd.); and an acrylic acid or a methacrylic acid polymer such as Polyflow No. 75 and No. 95 (manufactured by Kyoeisha Yushikagaku Kogyo K. K.).

In another embodiment of the any of the above described positive working photosensitive compositions, the total loading of the two polymer components namely component b) said Novolak, and said component c), said acrylate polymer comprising structure (I), are ones wherein said Novolak polymers component b) may comprise from about 20 wt % to about 80 wt % of the total weight of the Novolak polymer component and the acrylate polymer component. In another aspect of this embodiment, component b) said Novolak polymer may comprise from about 30 wt % to about 75 wt % of the total weight of the Novolak polymer component and the acrylate polymer component. As a still further example and without limitation, Novolak polymers may comprise from about 40% to about 65% w/w of the total weight of the Novolak polymer component and the acrylate polymer component.

In all the embodiments described herein for the positive working photosensitive composition, the wt % of each solid component as a part of the total mass of solid components, when these are added up, must equal 100 wt %; this includes mandatory solid components a), b), c) d) and e) and any optional components such as the basic quencher or any impurities which may be present. Further, The term "solid component," as used herein refers to any component in the above described positive working photosensitive compositions, which is not the solvent component f) regardless of the actual physical state of these "solid component," which may be either a solid or a liquid.

In all the embodiments described herein for the positive working photosensitive composition, the wt % of component a), said photoacid generator, as a part of the total mass of solid components, may range from about 0.1 wt % to about 6 wt %. In an aspect of this embodiment it may range from about 0.1 wt % to about 4 wt %. In still another aspect of this embodiment it may range from about 0.2 wt % to about 2 wt %.

In all the embodiments described herein for the positive working photosensitive composition, the wt % of component b), said Novolak polymer, as a part of the total mass of solid components, may range from about 14 wt % to about 80 wt %. In an aspect of this embodiment it may range from about 30 wt % to about 60 wt %. In still another aspect of this embodiment it may range from about 40 wt % to about 60 wt %.

In all the embodiments described herein for the positive working photosensitive composition, the wt % of component c), said acrylate polymer(s), as a part of the total mass of solid components, may range from about 14 wt % to about 80 wt %. In an aspect of this embodiment it may range from about 25 wt % to about 60 wt %. In still another aspect of this embodiment it may range from about 25 wt % to about 50 wt %.

In all the embodiments described herein for the positive working photosensitive composition, the wt % of component d) said glycidyl hydroxy benzoic acid condensate material(s), as a part of the total mass of solid components, may range from about 1 wt % to about 30 wt %. In an aspect of this embodiment it may range from about 3 wt % to about 20 wt %. In still another aspect of this embodiment it may range from about 5 wt % to about 15 wt %.

In all the embodiments described herein for the positive working photosensitive composition, the wt % of component e) said heterocyclic thiol compound(s), as a part of the total mass of solid components, may range from about 0.01 wt % to about 0.5 wt %. In an aspect of this embodiment it may range from about 0.02 wt % to about 0.4 wt %. In still another aspect of this embodiment it may range from about 0.05 wt % to about 0.25 wt %.

In all the embodiments described herein for the positive working photosensitive composition, the wt %, as a part of the total mass of solid components, of an optional base quencher component(s), when it is present, may range from about 0.01 wt % to about 0.5 wt %. In an aspect of this embodiment it may range from about 0.02 wt % to about 0.3 wt %. In still another aspect of this embodiment it may range from about 0.05 wt % to about 0.2 wt %.

In all the embodiments described herein for the positive working photosensitive composition, the wt %, as a part of the total mass of solid components, of an optional surfactant component(s), when it is present, may range from about 0.001 wt % to about 1 wt %. In an aspect of this embodiment it may range from about 0.001 wt % to about 0.2 wt %. In still another aspect of this embodiment it may range from about 0.005 wt % to about 0.15 wt %. In still another aspect of this embodiment it may range from about 0.005 wt % to about 0.30 wt %.

In all the embodiments described herein, the positive working photosensitive composition, the wt % of solids component of in the total composition including solvent may range from about 0.05 wt % to about 65 wt %. In another aspect of this embodiment this may range from about 20 wt % to about 60 wt %. In yet another aspect of this embodiment this may range from about 35 wt % to about 60 wt %.

In all the described embodiment the total wt % of each component as part of the total mass of all components, including mandatory components a), b), c) d) e) and f)(a.k.a. solvent, and any optional components or present impurities in the composition must equal 100 wt %.

The term "solid component," as used herein refers to any component in the above described positive working photosensitive compositions, which is not a solvent component regardless of the actual physical state of these "solid component," which may be either a solid or a liquid.

Further disclosed herein is a method of forming a positive relief image comprising: forming a photosensitive layer by applying the positive working photosensitive composition described herein to a substrate, thus forming a film and then baking; image-wise exposing the photosensitive layer to actinic radiation to form a latent image; and developing the latent image in a developer. Optionally, the image-wise exposed photosensitive layer may be thermally treated, depending on the chemistry of deprotection.

The procedure for the preparation of a patterned photoresist layer by using the photosensitive composition disclosed herein can be conventional. For example, a substrate such as a semiconductor silicon wafer or one with a metal coating as described previously, is evenly coated with the photosensitive composition in the form of a solution by using a suitable coating machine such as a spin-coater followed by baking in a convection oven or on a hotplate to form a photoresist layer which is then exposed pattern-wise to actinic radiation such as deep ultraviolet light, near ultraviolet light, or visible light emitted from low-pressure, high-pressure and ultra-high-pressure mercury lamps, arc lamps, xenon lamps, ArF, KrF and $F_2$ excimer lasers, electron beams, x-rays, extreme UV sources, and the like through a photomask or a from a reflective mask bearing a desired pattern on an exposure apparatus and electron beams scanned in accordance with a desired pattern to build up a latent image of the pattern in the resist layer. The actinic radiation may range from 250 nm to 450 nm or be a broadband radiation. Thereafter, the latent image in the photoresist layer may optionally be baked in a convection oven or on a hotplate, developed using an alkaline developer solution such as an aqueous solution of tetra ($C_1$-$C_4$ alkyl) ammonium hydroxide, choline hydroxide, lithium hydroxide, sodium hydroxide, or potassium hydroxide, for example, tetramethyl ammonium hydroxide (TMAH), in a concentration of 1 to 10% w/w, to yield a patterned photoresist layer having good fidelity to the pattern of the photomask. Thicknesses may range from 20 nm to 200 microns. To achieve these thicknesses, a combination of different spin speeds and total solids concentrations may be employed as noted above may be used. Depending on the size of the substrate, spin speeds of from 500 rpm to 10,000 rpm may be used. In some instances, in order to achieve the higher coating thicknesses of about 100 to about 200 microns, a double spin coating may be employed.

Depositing the metal on a patterned resist on substrate formed by the photosensitive composition disclosed herein may be accomplished by using metal electroplating (a.k.a. metal electro deposition, electrolytic plating).

Generally, methodologies for electroplating of various metals with different processes and metals are described in "The plating Forecast and Assurance, Larry G Yeon, Larry King Corporation, Chapter 1, pages 5 to 56, 2004." This metal electroplating may be done by Electrolytic plating processes such as rack plating, barrel plating, brush plating, continuous plating, electroforming, pulse current plating.

As applied to this invention, metal electroplating onto said patterned resist on substrate formed by the inventive photosensitive compositions disclosed herein may be done for a variety of metals non-limiting examples are gold, copper, silver, tungsten, cadmium, Chromium, Indium, Iron, Lead, Nickel, Palladium, Platinum, Rhodium, Ruthenium, Tin, Zinc, Aluminum, Tantalum, and Niobium. In one aspect of this, the electroplating may be done with gold, copper, silver, tungsten, Chromium, Indium, Nickel, Palladium, Rhodium, Tantalum, Niobium and Tin/Silver alloys deposited by electroplating. In one aspect of this embodiment, the electroplating may be done with gold, copper, silver, tungsten, Chromium, Indium, Nickel, Palladium, Rhodium, Tantalum, and Niobium. In another aspect of this the electroplating may be done with copper, tungsten, Chromium, Nickel, Tantalum, Niobium and Tin/Silver alloys deposited by electroplating. In one particular aspect of this, the electroplating can be done with copper.

Once the metal has been selectively electroplated onto said patterned photoresist on the substrate, the resist may be removed leaving behind a metal pattern on the substrate. This removal of said resist pattern is accomplished by using a chemical stripper (a.k.a. remover) or a solvent. Suitable strippers for removing the resist pattern are as non-limiting examples, materials such as AZ® 400T Remover or AZ® Kwik Strip, or other strippers which are based on a polar aprotic solvent such as N-Methyl-2-pyrrolidone (NMP), dimethylsulfoxide (DMSO) and the like, either alone or in combination with other components selected from other solvents, water and bases (e.g. TMAH).

Suitable solvent for removing the resist pattern are any organic solvent which will dissolve the unpatterned resist, examples of such solvent are alkyl ketones such as acetone, and also any of the solvent described above which have been described as suitable solvents for these inventive compositions. A non-limiting example for instance is PGMEA.

Another aspect of this invention is a method of forming a relief image (a.k.a resist pattern on a substrate) which comprises the following steps:
a) forming a photosensitive layer by applying any of the positive working photosensitive composition described herein on a substrate thus forming a film and then baking the film;
b) image-wise exposing the photosensitive layer to actinic radiation to form a latent image;
c) developing the latent image in a developer.

In another aspect of this invention the method of forming a relief image comprises the following steps:
a') forming a photosensitive layer by applying any of the positive working photosensitive composition as described herein to a substrate forming thus a film and then baking the film;
b') image-wise exposing the photosensitive layer to actinic radiation to form a latent image;
c') thermally treating the image-wise exposed photosensitive layer forming a baked latent image;
d') developing the baked latent image in a developer.

In another aspect of this invention it comprised a method of forming a relief image, which is then used as a mask in metal deposition to form metal patterns which comprises the following steps:
a") forming a photosensitive layer by applying any of the positive working photosensitive composition described herein on a substrate thus forming a film and then baking the film;
b") image-wise exposing the photosensitive layer to actinic radiation to form a latent image;
c") developing the latent image in a developer to form a resist pattern on the substrate.

d") selectively electroplating on the substrate using the resist pattern as a barrier
e") stripping the resist pattern leaving behind the selectively electroplated metal, thereby creating a metal pattern on the substrate.

In another aspect of this invention it comprised as method of forming a relief image, which is then used as a mask in metal deposition to form metal patterns which comprises the following steps:
a''') forming a photosensitive layer by applying any of the positive working photosensitive composition described herein on a substrate thus forming a film and then baking the film;
b''') image-wise exposing the photosensitive layer to actinic radiation to form a latent image;
c''') thermally treating the image-wise exposed photosensitive layer forming a baked latent image.
d''') developing the baked latent image in a developer to form a resist pattern on the substrate.
e''') selectively electroplating on the substrate using the resist pattern as a barrier
f''') stripping the resist pattern leaving behind the selectively electroplated metal, thereby creating a metal pattern on the substrate.

Another aspect of this invention is a glycidyl hydroxy benzoic acid condensate material comprising one or more compounds having structure (II),

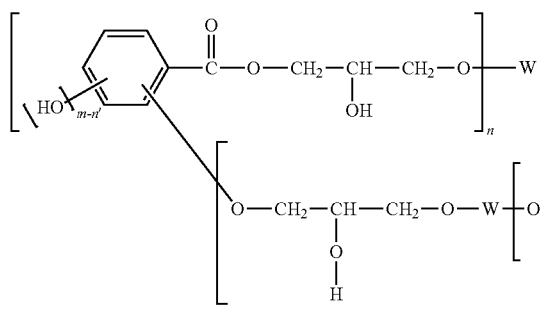
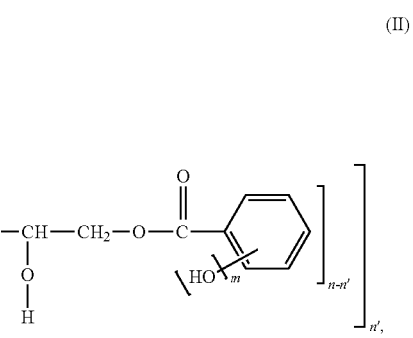

(II)

wherein, W is an organic moiety having a molecular weight of 600 or less,
wherein W forms an ether bond with the oxygen to which it is bound,
m is an integer from 1 to 3 and
n is an integer from 1 to 4, and further provided that when m is 1, n is 3 or 4,
and when m is 2 or 3, n is an integer from 1 to 4,
n' is 0 or 1.

In another embodiment of the above glycidyl hydroxy benzoic acid condensate material it is any one of the variations of component d) as described above in for the positive working photosensitive compositions.

Another aspect of this invention is the use of a glycidyl hydroxy benzoic acid condensate material comprising one or more compounds having structure (II) as described above, or of the positive working photosensitive composition of the invention, as described above, for forming a positive relief image on a substrate.

Each of the documents referred to above are incorporated herein by reference in its entirety, for all purposes. The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

Additive Synthesis Example 1

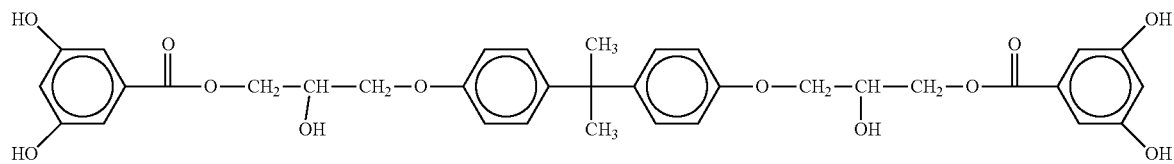

61.6 g of 3,5-dihydroxy benzoic acid, 68.08 g of bisphenol A diglycidyl ether, 0.45 g of benzyl triethylammonium chloride were mixed in 130 g of propylene glycol methyl ether (PGME) solvent. The reaction proceeded at 110° C. under nitrogen for 15 hours. After cooling down to room temperature, the reaction mixture was precipitated in DI water. The solid glycidyl hydroxy benzoic acid condensate material was washed and dried under vacuum at 50° C. yielding 130.0 g (100% yield) with a Gel permeation chromatograph (GPC) (using polystyrene standards) weight average molecular weight of Mw=1151 and a number average molecular weight Mn=1090. Thus, a glycidyl hydroxy benzoic acid condensate material was obtained which has a dissolution rate in AZ® 300 MT developer is: 5400 Å/sec. Proton NMR analysis shows that this compound is ~95% pure containing ~5% of a side product in which one of the hydroxy phenols has also undergone condensation with a glycidyl moiety. This was ascertained by analysis by Proton NMR. This NMR was run in Acetone-d6. In this spectra the two aromatic hydrogens of the dihydroxybenzoic unit aromatic hydrogens which are ortho to the carbonyl are seen 7.06 ppm while the 8 aromatic protons in the bisphenol A derived unit are seen 7.173 and 7.152, 6.901 and 6.879 ppm, If 100% pure this compound would give a proton ratio of 2/1 for the aromatic protons in the bisphenol-A derivative versus the two ortho dihydroxybenzoic aromatic protons. The ratio observed was 2.036 which indicated at least a 94.6% purity. The presence of this small impurity is also confirmed by GPC and HPLC data. The GPC and high-pressure liquid chromatograph (HPLC) data also confirmed the absence of any residual starting materials. The slight impurity represents a slight side reaction of the phenolic hydroxy moieties with the epoxide moiety during synthesis.

Additive Synthesis Example 2

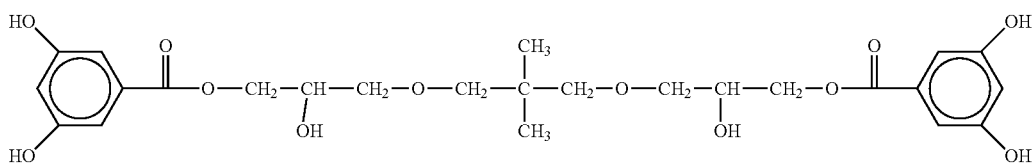

15.4 g of 3,5-dihydroxy benzoic acid, 10.81 g of neopentyl glycol diglycidyl ether, 0.01 g of benzyl triethylammonium chloride were mixed in 26 g of 1-Methoxy-2-propanyl acetate (PGMEA) solvent. The reaction proceeded at 110° C. under nitrogen for 8 hours. After cooling down to room temperature, the reaction mixture was transferred to a bottle for use. The GPC (using polystyrene standards) shows it has a weight average molecular weight of Mw=736 and a number average molecular weight Mn=505. The dissolution rate in AZ® 300 MIF developer is: 5500 Å/sec. The GPC data also confirmed the absence of any residual starting materials.

Additive Synthesis Example 3

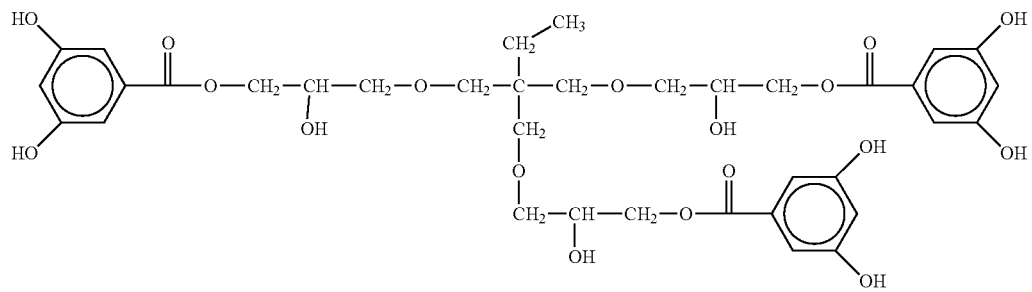

46.2 g of 3,5-dihydroxybenzoic acid, 30.2 g of trimethylolpropanetriglycidyl ether, 0.45 g of benzyl triethylammonium chloride were mixed in 76.4 g of propyleneglycol monomethylether acetate(PGMEA) solvent. The reaction proceeded at 110° C. under nitrogen for 12 hours. After cooling down to room temperature, the reaction mixture was transferred to a bottle for use. The GPC (using polystyrene standards) shows it has a weight average molecular weight of Mw=1084 and a number average molecular weight Mn=794. The dissolution rate in AZ® 300 MT developer is: 7400 Å/sec. The GPC data also confirmed the absence of any residual starting materials.

Additive Synthesis Example 4

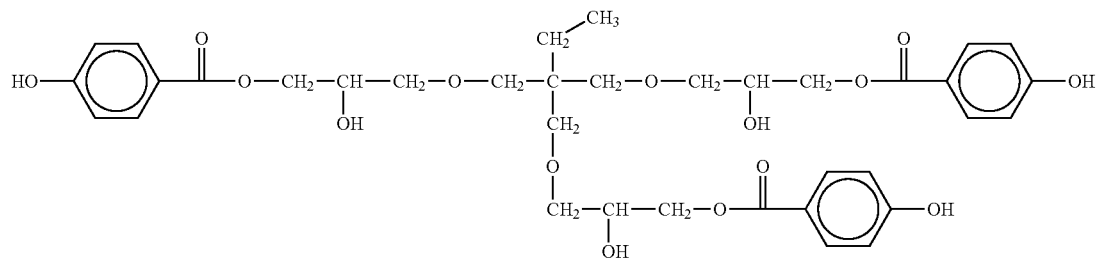

41.4 g of 4-hydroxybenzoic acid, 30.2 g of trimethylolpropanetriglycidyl ether, 0.14 g of benzyl triethylammonium chloride were mixed in 107.5 g of propyleneglycol monomethylether acetate(PGMEA) solvent. The reaction proceeded at 140° C. under nitrogen for 17 hours. After cooling down to room temperature, the reaction mixture was transferred to a bottle for use. The GPC (using polystyrene standards) shows it has a weight average molecular weight of Mw=1409 and a number average molecular weight Mn=1181. The dissolution rate in AZ® 300 MIF developer is: 6700 Å/sec.

Additive Synthesis Example 5: (Comparative Material)

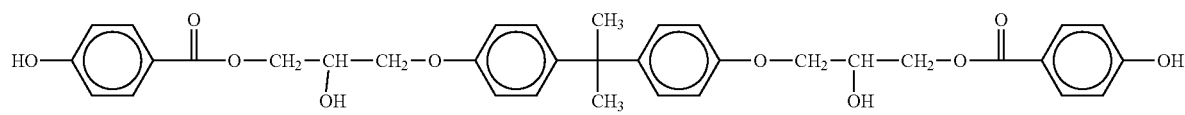

26.24 g (0.19 mol) of 4-hydroxy benzoic acid, 34.04 g (0.1 mol) of bisphenol A diglycidyl ether, 0.1 g of benzyl triethylammonium chloride were mixed in 60.28 g of propyleneglycol monomethylether acetate (PGMEA) solvent. The reaction proceeded at 110° C. under nitrogen for 15 hours. After cooling down to room temperature, the reaction mixture was transferred to a bottle for use. The GPC (using polystyrene standards) shows it has a weight average molecular weight of Mw=1538, a number average molecular weight Mn=1098. The dissolution rate in AZ® 300 MIF developer is: 5 Å/sec.

Additive Synthesis Example 6: (Comparative Material)

15.4 g (0.1 mol) of 3,5-dihydroxy benzoic acid, 53.75 g of poly(bisphenol A-co-epichlorohydrin), glycidyl end-capped (average Mn~1075), 0.1 g of benzyl triethylammonium chloride were mixed in 104 g of propylene glycol methyl ether (PGME) solvent. The reaction proceeded at 110° C. under nitrogen for 10 hours. After cooling down to room temperature, the reaction mixture was precipitated in DI water. The solid glycidyl hydroxy benzoic acid condensate material was washed and dried under vacuum at 50° C. yielding 69.0 g (99.8% yield) with a GPC (using polystyrene standards) weight average molecular weight of Mw=3829, a number average molecular weight Mn=1895. Thus, the glycidyl hydroxy benzoic acid condensate material was obtained. The dissolution rate in AZ® 300 MIF developer is: 6 Å/sec.

Additive Synthesis Example 7

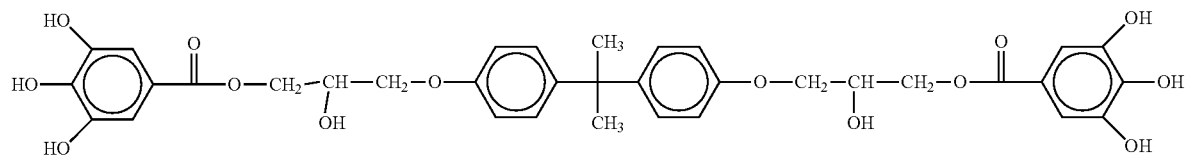

25.0 g (0.147 mol) of gallic acid, 23.76 g (0.0698 mol) of bisphenol A diglycidyl ether, 0.18 g of benzyl triethylammonium chloride were mixed in 114 g of mixed solvent of propyleneglycol monomethylether acetate and propylene glycol methyl ether (PGMEA/PGME:1.85/1). The reaction proceeded at 110° C. under nitrogen for 15 hours. After cooling down to room temperature, the reaction mixture was transferred to a bottle for use. The GPC (using polystyrene standards) shows it has a weight average molecular weight of Mw=1867 and a number average molecular weight Mn=1024. The dissolution rate in AZ® 300 MIF developer is: 10500 Å/sec.

Additive Synthesis Example 8

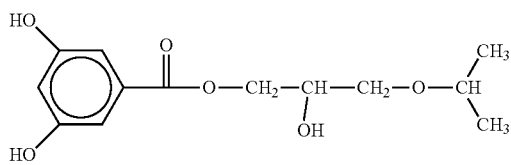

30.8 g of 3,5-dihydroxy benzoic acid, 23.23 g of glycidyl isopropyl ether, 0.13 g of benzyl triethylammonium chloride were mixed in 81 g of 1-Methoxy-2-propanyl acetate (PGMEA) solvent. The reaction proceeded at 135° C. under nitrogen for 18 hours. Then the solvent was evaporated at 50° C. under vacuum. The GPC (using polystyrene standards) shows it has a weight average molecular weight of Mw=429 and a number average molecular weight Mn=407. The dissolution rate in AZ 300 MIF developer is: 10645 Å/sec Dissolution Rate Testing of Phenolic Additives:

All glycidyl hydroxy benzoic acid condensate material was dissolved in PGMEA to make a solution 50%. Then coatings were prepared by spin coating the resist samples and applying a soft bake for 180 seconds at 110° C. on standard wafer track hot plate in contact mode. The spin speed was adjusted to obtain 10-micron thick resist films. All film thickness measurements were conducted on Si wafers using optical measurements. The film was soaked in AZ® 300 MIF developer (0.26N aqueous solution of tetramethyl ammonium hydroxide=TMAH) (EMD Performance Materials, AZ Products, Somerville, NJ) at 23° C. The dissolution rate was determined by measuring the film loss in a specific time.

Acrylic Polymer Synthesis Example 1

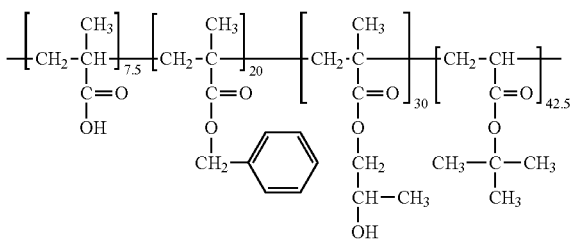

Monomer repeat unit percentages are given as mole percentages. In this example, 6.46 g of methacrylic acid, 35.24 g of benzyl methacrylate, 43.25 g of hydroxypropyl methacrylate, 54.47 g of tert-butyl acrylate are mixed in 209.1 g of PGME solvent. The polymerization reaction proceeds in the presence of 2.3 g of AIBN at 90° C., under nitrogen for 18 hours. After cooling down to room temperature, the reaction mixture is precipitated in DI water. The polymer solid is washed and dried under vacuum at 45° C., yielding 137.1 g (98% yield) with a GPC (using polystyrene standards) weight average molecular weight of 15,072 Daltons and a number average molecular weight of 7345 Daltons.

Acrylic Polymer Synthesis Example 2

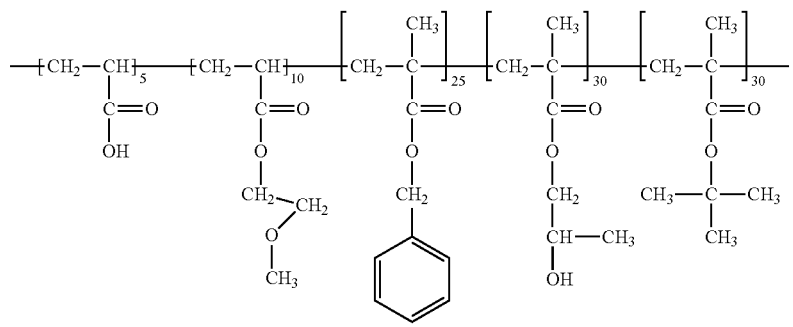

1.8 g of acrylic acid, 6.5 g of methoxyethyl acylate, 22.0 g of benzyl methacrylate, 21.6 g of hydroxypropyl methacrylate, 21.3 g of tert-butyl methacrylate were mixed in 179.6 g of PGME solvent. The polymerization reaction proceeded in the presence of 3.3 g of AIBN at 80° C., under nitrogen for 18 hours. After cooling down to room temperature, the reaction mixture was precipitated in DI water. The white polymer solid was washed and dried under vacuum at 45° C., yielding 73.5 g (>99% yield) with a GPC (using polystyrene standards) weight average molecular weight of 11,868 Daltons and a number average molecular weight of 5382.

Acrylic Polymer Synthesis Example 3

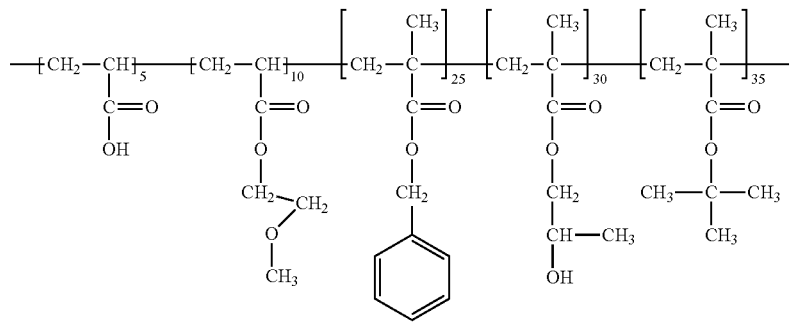

1.8 g of acrylic acid, 6.5 g of methoxyethyl acylate, 17.6 g of benzyl methacrylate, 21.6 g of hydroxypropyl methacrylate, 24.9 g of tert-butyl methacrylate were mixed in 172.9 g of PGME solvent. The polymerization reaction proceeded in the presence of 1.6 g of AIBN at 90° C., under nitrogen for 18 hours. After cooling down to room temperature, the reaction mixture was precipitated in DI water. The white polymer solid was washed and dried under vacuum at 45° C., yielding 71.6 g (99% yield) with a GPC (using polystyrene standards) weight average molecular weight of 17,205 Daltons and a number average molecular weight of 8407.

Acrylic Polymer Synthesis Example 4

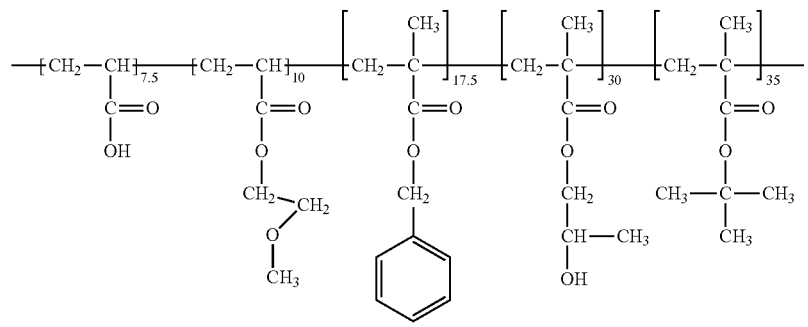

2.7 g of acrylic acid, 6.5 g of methoxyethyl acylate, 15.4 g of benzyl methacrylate, 21.6 g of hydroxypropyl methacrylate, 24.9 g of tert-butyl methacrylate were mixed in 135.2 g of PGME solvent. The polymerization reaction proceeded in the presence of 1.6 g of AIBN at 90° C., under nitrogen for 18 hours. After cooling down to room temperature, the reaction mixture was precipitated in DI water. The white polymer solid was washed and dried under vacuum at 45° C., yielding 70.3 g (99% yield) with a GPC (using polystyrene standards) weight average molecular weight of 17,153 Daltons and a number average molecular weight of 9424.

Acrylic Polymer Synthesis Example 5

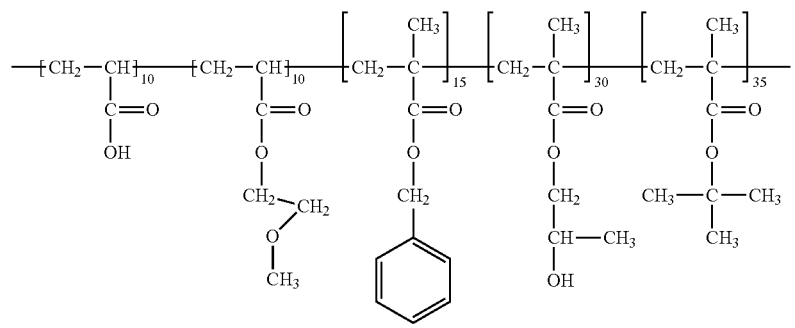

3.6 g of acrylic acid, 6.5 g of methoxyethyl acylate, 13.2 g of benzyl methacrylate, 21.6 g of hydroxypropyl methacrylate, 24.9 g of tert-butyl methacrylate were mixed in 135.8 g of PGME solvent. The polymerization reaction proceeded in the presence of 3.3 g of AIBN at 90° C., under nitrogen for 18 hours. After cooling down to room temperature, the reaction mixture was precipitated in DI water. The white polymer solid was washed and dried under vacuum at 45° C., yielding 70.8 g (>99% yield) with a GPC (using polystyrene standards) weight average molecular weight of 11,913 Daltons and a number average molecular weight of 5564.

Acrylic Polymer Synthesis Example 6

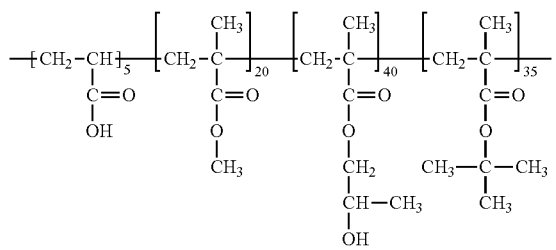

Acrylic Polymer Synthesis Example 7

1.8 g of acrylic acid, 10.0 g of methyl methacrylate, 28.8 g of hydroxypropyl methacrylate, 24.9 g of tert-butyl methacrylate were mixed in 124.7 g of PGME solvent. The polymerization reaction proceeded in the presence of 1.6 g of AIBN at 90° C., under nitrogen for 18 hours. After cooling down to room temperature, the reaction mixture was precipitated in DI water. The white polymer solid was washed and dried under vacuum at 45° C., yielding 64.4 g (98% yield) with a GPC (using polystyrene standards) weight average molecular weight of 16,650 Daltons. and a number average molecular weight of 7919.

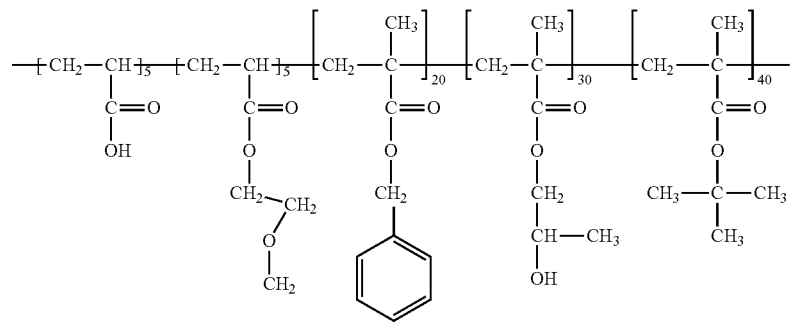

1.8 g of acrylic acid, 3.3 g of methoxyethyl acylate, 17.6 g of benzyl methacrylate, 21.6 g of hydroxypropyl methacrylate, 28.4 g of tert-butyl methacrylate were mixed in 138.2 g of PGME solvent. The polymerization reaction proceeded in the presence of 1.6 g of AIBN at 90° C., under nitrogen for 18 hours. After cooling down to room temperature, the reaction mixture was precipitated in DI water. The white polymer solid was washed and dried under vacuum at 45° C., yielding 71.9 g (99% yield) with a weight average molecular weight of 15,843 Daltons and a number average molecular weight of 7642 Daltons.

Acrylic Polymer Synthesis Example 8

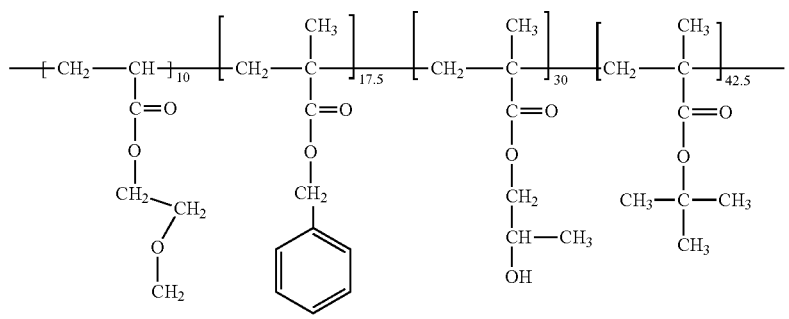

6.5 g of methoxyethyl acylate, 15.4 g of benzyl methacrylate, 21.6 g of hydroxypropyl methacrylate, 30.2 g of tert-butyl methacrylate were mixed in 140.0 g of PGME solvent. The polymerization reaction proceeded in the presence of 1.6 g of AIBN at 90° C., under nitrogen for 18 hours. After cooling down to room temperature, the reaction mixture was precipitated in DI water. The white polymer solid was washed and dried under vacuum at 45° C., yielding 72.45 g (98% yield) with a GPC (using polystyrene standards) weight average molecular weight of 17,525 Daltons. and a number average molecular weight of 8695 Daltons.

Acrylic Polymer Synthesis Example 9

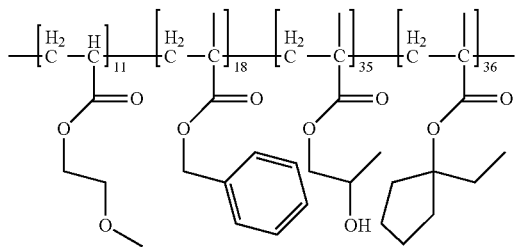

Monomer repeat unit percentages are given as mole percentages. In this example, 7.16 g of methoxyethyl acylate, 15.86 g of benzyl methacrylate, 25.23 g of hydroxypropyl methacrylate, 32.78 g of 1-ethylcyclopentyl methacrylate are mixed in 152.6 g of PGME solvent. The polymerization reaction proceeds in the presence of 1.2 g of AIBN at 90° C., under nitrogen for 18 hours. After cooling down to room temperature, the reaction mixture is precipitated in DI water. The polymer solid is washed and dried under vacuum at 45° C., yielding 79.3 g (98% yield) with a GPC (using polystyrene standards) weight average molecular weight of 17,888 Daltons and a number average molecular weight of 9502.

Acrylic Polymer Synthesis Example 10

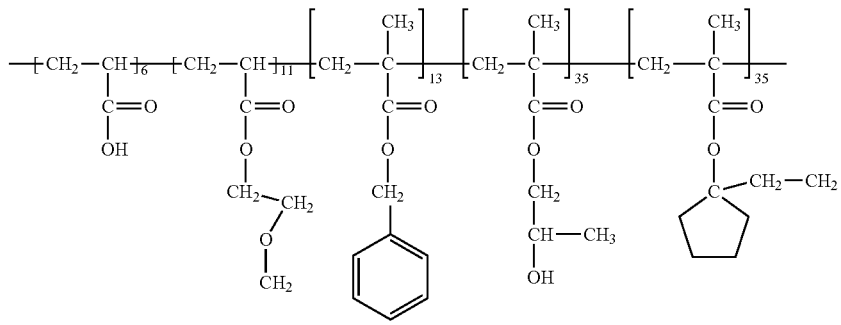

4.32 g of acrylic acid, 14.32 g of methoxyethyl acylate, 22.91 g of benzyl methacrylate, 50.46 g of hydroxypropyl methacrylate, 63.75 g of 1-ethylcyclopentyl methacrylate are mixed in 158.5 g of PGME solvent. The polymerization reaction proceeds in the presence of 2.71 g of AIBN at 90° C., under nitrogen for 18 hours. After cooling down to room temperature, the reaction mixture is precipitated in DI water. The polymer solid is washed and dried under vacuum at 45° C., yielding 153.45 g (98.5% yield) with a GPC (using polystyrene standards) weight average molecular weight of 17,103 Daltons and a number average molecular weight of 8316.

Acrylic Polymer Synthesis Example 11

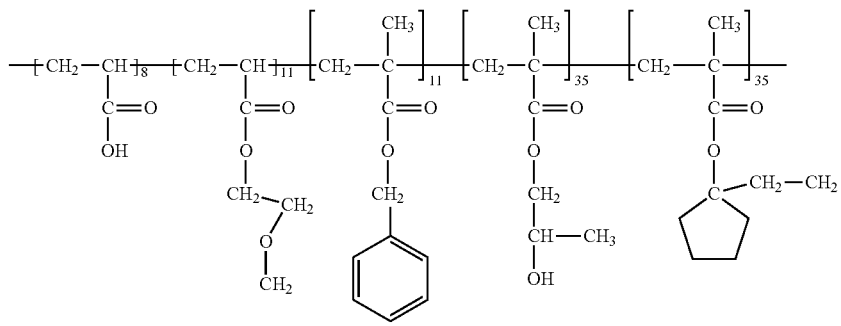

5.76 g of acrylic acid, 14.32 g of methoxyethyl acylate, 19.38 g of benzyl methacrylate, 50.46 g of hydroxypropyl methacrylate, 63.75 g of 1-ethylcyclopentyl methacrylate are mixed in 156.4 g of PGME solvent. The polymerization reaction proceeds in the presence of 2.71 g of AIBN at 90° C., under nitrogen for 18 hours. After cooling down to room temperature, the reaction mixture is precipitated in DI water. The polymer solid is washed and dried under vacuum at 45° C., yielding 150.2 g (97.7% yield) with a GPC (using polystyrene standards) weight average molecular weight of 15,557 Daltons and a number average molecular weight of 7795.

Acrylic Polymer Synthesis Example 12

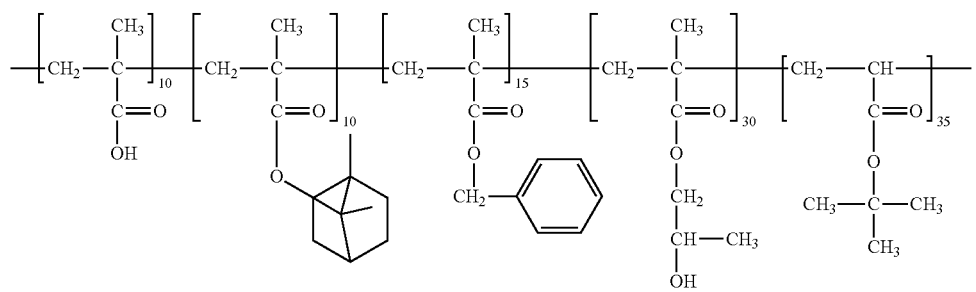

8.61 g of methacrylic acid, 22.23 g of isobornyl methacylate, 26.43 g of benzyl methacrylate, 43.25 g of hydroxypropyl methacrylate, 44.36 g of tert-butyl acrylate are mixed in 156.4 g of PGME solvent. The polymerization reaction proceeds in the presence of 2.46 g of AIBN at 90° C., under nitrogen for 18 hours. After cooling down to room temperature, the reaction mixture is precipitated in DI water. The polymer solid is washed and dried under vacuum at 45° C., yielding 142.5 g (98.3% yield) with a GPC (using polystyrene standards) weight average molecular weight of 25,535 Daltons and a number average molecular weight of 12,215.

Novolak polymers: For the following formulation examples, three Novolak polymers were used. Novolak-1 (SPN-560S) was synthesized from m-cresol and formaldehyde and had a bulk dissolution rate in 2.38% aqueous TMAH developer of 700 Å/sec. Novolak-2 (SPN 560F) was synthesized from m-cresol and formaldehyde and had a bulk dissolution rate in 2.38% aqueous TMAH developer of 1,600 Å/sec. Novolak-3 is a 1/1 blend of Novolak-1 and Novolak-2, with a bulk dissolution rate in 2.38% aqueous TMAH developer of 1,000 Å/sec.

FORMULATION EXAMPLES

Chemicals

α,α-Bis(4-hydroxyphenyl)-4-(4-hydroxy-α,α-dimethyl-benzypethylbenzene, (TPPA) was obtained from Honshu Chemical Chemical Co, Ltd, Yaesu-Daibiru Bldg., 1-1, Kyobashi 1-chome, Chuo-ku, Tokyo 104-0031, Japan;

N-hydroxy-naphthylimide triflate (NIT), obtained from Heraues Daychem (Vandalia, OH).

3-Mercapto-1,2,4-triazole (or also named as 1H-1,2,3-triazole-3-thiol) (MTA) from Sigma-Aldrich Corp. (St. Louis, MO, USA).

The surfactant, APS-437, was obtained from ShinEtsu Chemical Co. LTd, Tokyo, Japan Company).

Novolak components are m-cresol/formaldehyde Novolak (SPN-560F and SPN-560S), supplied by Allnex, Brussels, Belgium.

Tetrabutylammonium oxalate was obtained from Merck Performance Materials, Wiesbaden, Germany.

NK-280 is a diazonaphthoquinone photoactive compound (DNQ-PC) sold under this name by TOYO GOSEI., LTD and having the following general structure:

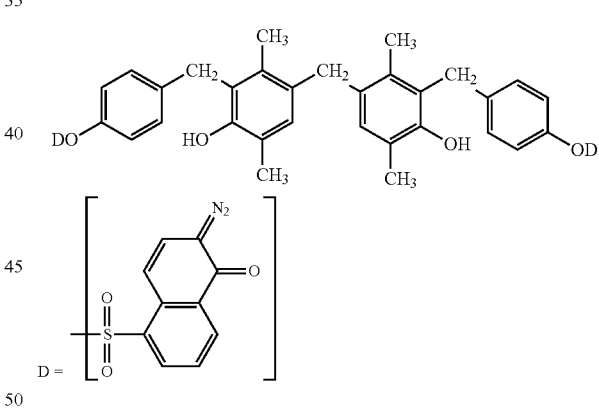

Formulation Example 1

4.2 g glycidyl hydroxy benzoic acid condensate material of additive Synthesis Example 1, 16.5 g of acrylic polymer resin of Acrylic polymer synthesis example 12, 20.9 g of Novolak-3, 0.42 g of 1,3-dioxo-1H-benzo[de]isoquinolin-2 (3H)-yl trifluoromethanesulfonate [also called naphthalene dicarboximidyl triflate, NIT] (NIT PAG), 0.075 g of 1H-1,2,4-triazole-3-thiol, 0.055 g of tetrabutyl ammonium oxalate and 0.050 g of APS-437 were dissolved in 57.8 g of PGMEA solvent to obtain a resist solution at 42.2% solid. This solution was coated on copper wafers and produced 10 um films dried at 110° C. for 180 seconds. The resist was processed to produce patterned images post exposure baked at 90° C. for 60 seconds and developed for 120 seconds.

Formulation Examples 2-8

In these formulations additive synthesis example 1 in formulation example 1 was replaced respectively with additive synthesis examples 2, 3, 4, 5, 6, 7 and 8.

Formulation Example 9 (Comparative Example)

16.5 g of acrylic polymer resin of Acrylic polymer synthesis example 12, 25.1 g of Novolak-3, 0.42 g of NIT PAG, 0.075 g of 1H-1,2,4-triazole-3-thiol, 0.055 g of tetrabutyl ammonium oxalate and 0.050 g of APS-437 were dissolved in 57.8 g of PGMEA solvent to obtain a resist solution at 42.2% solid. This solution was coated on copper wafers and produced 10 um films dried at 110° C. for 180 seconds. The resist was processed to produce patterned images post exposure baked at 90° C. for 60 seconds and developed for 120 seconds. The resulting resist pattern profiles shows no undercut. This example is used to compare with Example 1-8 to show the significant influence of additive of condensates of multifunctional glycidyl compounds and 4-hydroxybenzoic acid or 3,5-dihydroxybenzoic acid or gallic acid on resist undercut profile on copper substrates.

Formulation Example 10, 11, 12, 13, 14, 15, 16, 17, 18, 19, 20

In these formulations the acrylic synthesis polymer 12 used in formulation example 1 where respectively replaced with acrylic synthesis examples 1, 2, 3, 4, 5, 6, 7, 8, 9, 10, 11 to obtain the resist solutions. Those resists were tested under the same processing condition as mentioned above.

TABLE 1

Formulations Containing different synthesized additives

| Component type | Component name | 1 Wt. % | 2 Wt. % | 3 Wt. % | 4 Wt. % | 5 Wt. % | 6 Wt. % | 7 Wt % | 8 Wt. % | 9 Wt. % |
|---|---|---|---|---|---|---|---|---|---|---|
| Synthesized additive | Additive synthesis example 1 | 4.2 | | | | | | | | |
| | 2 | | 4.2 | | | | | | | |
| | 3 | | | 4.2 | | | | | | |
| | 4 | | | | 4.2 | | | | | |
| | 5 | | | | | 4.2 | | | | |
| | 6 | | | | | | 4.2 | | | |
| | 7 | | | | | | | 4.2 | | |
| | 8 | | | | | | | | 4.2 | |
| Acrylic polymer | Acrylic polymer synthesis example 12 | 16.5 | 16.5 | 16.5 | 16.5 | 16.5 | 16.5 | 16.5 | 16.5 | 16.5 |
| Novolak | Novolak-3 | 20.9 | 20.9 | 20.9 | 20.9 | 20.9 | 20.9 | 20.9 | 20.9 | 25.1 |
| PAG | NIT PAG | 0.42 | 0.42 | 0.42 | 0.42 | 0.42 | 0.42 | 0.42 | 0.42 | 0.42 |
| Additive | MTA | 0.075 | 0.075 | 0.075 | 0.075 | 0.075 | 0.075 | 0.075 | 0.075 | 0.075 |
| Quencher | TBA-Oxalate | 0.055 | 0.055 | 0.055 | 0.055 | 0.055 | 0.055 | 0.055 | 0.055 | 0.055 |
| Surfactant | APS437 | 0.05 | 0.05 | 0.05 | 0.05 | 0.05 | 0.05 | 0.05 | 0.05 | 0.05 |
| Solvent | PGMEA | 57.8 | 57.8 | 57.8 | 57.8 | 57.8 | 57.8 | 57.8 | 57.8 | 57.8 |
| | Total Wt. | 100 | 100 | 100 | 100 | 100 | 100 | 100 | 100 | 100 |

TABLE 2

Formulations containing different acrylic polymers.

| Component type | Component name | 10 Wt. % | 11 Wt. % | 12 Wt. % | 13 Wt. % | 14 Wt. % | 15 Wt. % | 16 Wt. % | 17 Wt. % | 18 Wt. % | 19 Wt. % | 20 Wt. % |
|---|---|---|---|---|---|---|---|---|---|---|---|---|
| Synthesized additive | Additive synthesis example 1 | 4.2 | 4.2 | 4.2 | 4.2 | 4.2 | 4.2 | 4.2 | 4.2 | 4.2 | 4.2 | 4.2 |
| Synthesized Acrylic polymer | synthesis example 1 | 16.5 | | | | | | | | | | |
| | 2 | | 16.5 | | | | | | | | | |
| | 3 | | | 16.5 | | | | | | | | |
| | 4 | | | | 16.5 | | | | | | | |
| | 5 | | | | | 16.5 | | | | | | |
| | 6 | | | | | | 16.5 | | | | | |
| | 7 | | | | | | | 16.5 | | | | |
| | 8 | | | | | | | | 16.5 | | | |
| | 9 | | | | | | | | | 16.5 | | |
| | 10 | | | | | | | | | | 16.5 | |
| | 11 | | | | | | | | | | | 16.5 |

TABLE 2-continued

Formulations containing different acrylic polymers.

| | | Examples | | | | | | | | | | |
|---|---|---|---|---|---|---|---|---|---|---|---|---|
| Component type | Component name | 10 Wt. % | 11 Wt. % | 12 Wt. % | 13 Wt. % | 14 Wt. % | 15 Wt. % | 16 Wt. % | 17 Wt. % | 18 Wt. % | 19 Wt. % | 20 Wt. % |
| Novolak | Novolak-3 | 20.9 | 20.9 | 20.9 | 20.9 | 20.9 | 20.9 | 20.9 | 20.9 | 20.9 | 20.9 | 20.9 |
| PAG | NIT PAG | 0.42 | 0.42 | 0.42 | 0.42 | 0.42 | 0.42 | 0.42 | 0.42 | 0.42 | 0.42 | 0.42 |
| Additive | MTA | 0.075 | 0.075 | 0.075 | 0.075 | 0.075 | 0.075 | 0.075 | 0.075 | 0.075 | 0.075 | 0.075 |
| Quencher | TBA-Oxalate | 0.055 | 0.055 | 0.055 | 0.055 | 0.055 | 0.055 | 0.055 | 0.055 | 0.055 | 0.055 | 0.055 |
| Surfactant | APS437 | 0.05 | 0.05 | 0.05 | 0.05 | 0.05 | 0.05 | 0.05 | 0.05 | 0.05 | 0.05 | 0.05 |
| Solvent | PGMEA | 57.8 | 57.8 | 57.8 | 57.8 | 57.8 | 57.8 | 57.8 | 57.8 | 57.8 | 57.8 | 57.8 |
| | Total Wt. | 100 | 100 | 100 | 100 | 100 | 100 | 100 | 100 | 100 | 100 | 100 |

TABLE 3

Formulations Containing different additives.

| | | Examples | | |
|---|---|---|---|---|
| Component type | Component name | 21 Wt. % | 22 Wt. % | 23 Wt. % |
| Synthesized additive | Additive synthesis example 1 | 4.2 | 4.2 | 4.2 |
| Acrylic polymer | Acrylic polymer synthesis example 12 | 16.5 | 16.5 | 16.5 |
| Novolak | Novolak-3 | 20.9 | 20.9 | 20.9 |
| PAG | NIT PAG | 0.42 | 0.42 | 0.42 |
| Additive | MT | 0.075 | | |
| | AT | | 0.075 | |
| | MI | | | 0.075 |
| Quencher | TBA-Oxalate | 0.055 | 0.055 | 0.055 |
| Surfactant | APS437 | 0.05 | 0.05 | 0.05 |
| Solvent | PGMEA | 57.8 | 57.8 | 57.8 |
| | Total Wt. | 100 | 100 | 100 |

Thiol additives, 6-methyl-2-thiouracil (or named as 2-mercapto-6-methylpyrimidine-4-ol) (MT) purchased from Millipore Sigma. 2-thiobarbituric acid (or named as 2-mercapto-pyrimidine-4,6-diol) (TA) purchased from Millipore Sigma; 2-Mercaptobenzimidazole (or named as 1H-benzo[d]imidazole-2-thiol) (MI) purchased from Millipore Sigma. Structures are as follows:

Structures of Thiol Additives

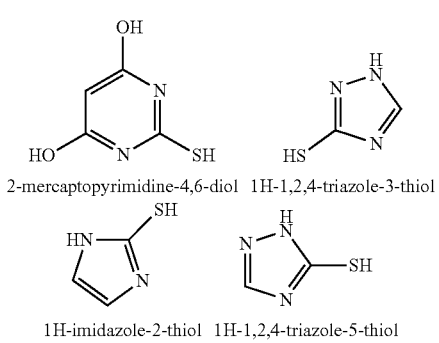

2-mercaptopyrimidine-4,6-diol     1H-1,2,4-triazole-3-thiol 1H-imidazole-2-thiol     1H-1,2,4-triazole-5-thiol

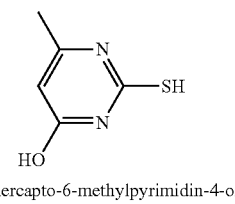

2-mercapto-6-methylpyrimidin-4-ol

TABLE 4

Comparative examples with commercial dissolution promoter.

| Examples Component type | Component name | 24 Wt. % | 25 Wt. % | 26 Wt. % |
|---|---|---|---|---|
| Dissolution Promotor | TPPA | 4.2 | | |
| | B126X-SA | | 4.2 | |
| | THPE | | | 4.2 |
| Acrylic polymer | Acrylic polymer synthesis example 12 | 16.5 | 16.5 | 16.5 |
| Novolak | Novolak-3 | 20.9 | 20.9 | 20.9 |
| PAG | NIT PAG | 0.42 | 0.42 | 0.42 |
| Additive | MTA | 0.075 | 0.075 | 0.075 |
| Quencher | TBA-Oxalate | 0.055 | 0.055 | 0.055 |
| Surfactant | APS437 | 0.05 | 0.05 | 0.05 |
| Solvent | PGMEA | 57.8 | 57.8 | 57.8 |
| | Total Wt. | 100 | 100 | 100 |

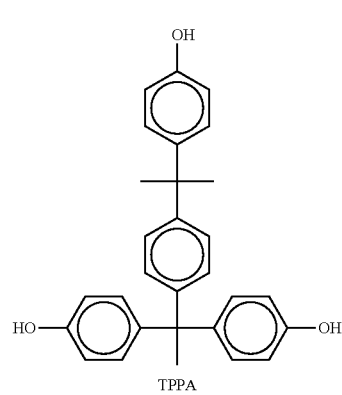

TPPA

TABLE 4-continued

Comparative examples with commercial dissolution promoter.

| Component type | Component name | Examples 24 Wt. % | 25 Wt. % | 26 Wt. % |
|---|---|---|---|---|

[Structure: B126X-SA — a triphenylmethane derivative with multiple OH and methyl substituents]

[Structure: THPE — 1,1,1-tris(4-hydroxyphenyl)ethane]

Formulation Example 27: (as Comparative Example in DNQ-Type Resist)

4.2 g glycidyl hydroxy benzoic acid condensate material of additive Synthesis Example 1, 30.575 g of Novolak SPN560 resin, 7.3 g of diazonaphtoquinonesulfonic ester [also called NK280], 0.075 g of 1H-1,2,4-triazole-3-thiol [also called 3-mercapto-1,2,4-triazole] and 0.050 g of APS-437 were dissolved in 57.8 g of PGMEA solvent to make a solution. The solution was filtered for tests.

Coating Procedure

Formulations 1-27 were tested on 6" diameter Si and Cu wafers. The Si wafers were dehydration baked and vapor primed with hexamethyldisilazane (HMDS). The Cu wafers were silicon wafers coated with 5,000 Angstroms of silicon dioxide, 250 Angstroms of tantalum nitride, and 3,500 Angstroms of Cu (PVD electroplated).

The resist coatings were prepared by spin coating the resist samples and applying a soft bake for 180 seconds at 110° C. on standard wafer track hot plate in contact mode. The spin speed was adjusted to obtain 10 microns thick resist films. All film thickness measurements were conducted on Si wafers using optical measurements.

Imaging Procedure:

The wafers were exposed on ASML 250 i-line stepper. The resist was post exposure baked at 90° C. for 60 seconds and puddle developed for 120 seconds in AZ® 300 MIF developer (0.26N aqueous solution of tetramethylammonium hydroxide=TMAH) (EMD Performance Materials, AZ Products, Somerville, NJ) at 23° C. The developed resist images were inspected using Hitachi 54700 or AMRAY 4200L electron microscopes.

Cu Electroplating

Cu electroplating was performed in a cup with Enthone GSW Copper Plating Solution. The Current density was controlled at 1 ASD; the plating temperature is 25° C.; the plating time 12 mins After plating, the resist was removed by acetone. The copper wire images were inspected using Hitachi 54700 or AMRAY 4200L electron microscopes.

Formulations 1 resulting resist pattern profiles undercut about 1.0-2.5 um. The resist formulations 2, 3, 4, 7 and 8 show the same undercut as formulation example 1. The resist formulation 5 and 6 show scums and undevelopable. Thus, the glycidyl hydroxy benzoic acid condensate material as additive example 5 and 6 having low dissolution rate cannot be used in resist formulation. The resist formulations 10-20 in Table 2 show undercut, indicating the glycidyl hydroxy benzoic acid condensate material additive can generate the undercut profile with various acrylic polymer resin. Formulations are not limited to those in the Table 1 and 2 tested. Replace additive synthesis example 1 in Table 2 with additive synthesis examples 2, 3, 4, 7 and 8 were also performed. The combination with additive synthesis resin examples 2, 3, 4, 7 and 8 with various acrylic polymer resin example 2-11 also show the undercut profiles.

Formulation in Table 3 were also tested. The profile show undercuts. The thiol additive does not affect the undercut profile.

Formulations in Table 4 were also tested. The commercial available phenolic resin does not generate undercut or tiny undercut <0.05 um at limited dose.

The formulation example 27 which was a comparative example was tested on ASML steeper. DNQ type photoresist with the additive synthesis example 1 resin did show the undercut profile.

After copper plated with the patterned undercut resist, it was found that the copper wire has footing. The copper wire with footing makes the wire stable (a.k.a. not easy to peel off) and because the contact area on the substrate was bigger, this is beneficial to the conductivity of any device made with these metallic lines having a footing.

Figure 2:
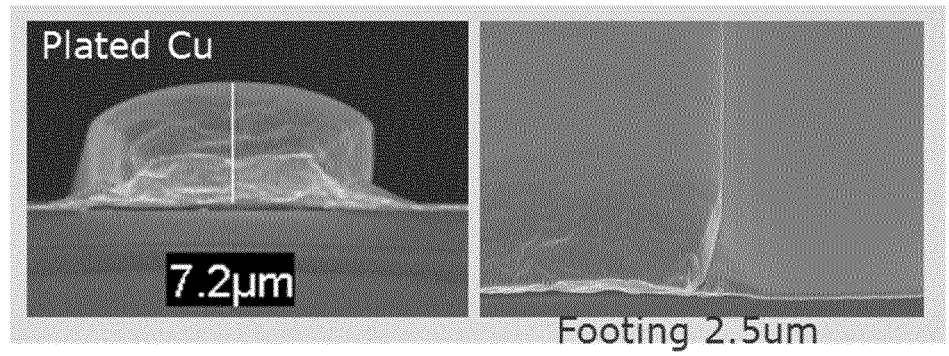
FIG. 2 Plated Cu wire with foot.

FIG. 1 shows the resist image produced with formulation example 20 which shows in 10 microns lines in a 12 microns thick resist film showing an undercut profile of 0.98 microns. In FIG. 1 the SEM image of the left shows the resist lines while the SEM image on the right shows an expansion of one of the lines showing a 0.98 micron undercut. FIG. 2 shows copper metal lines produced by electroplating copper onto the substrate with these undercut profiles after the resist was stripped off. This shows the beneficial footing produced in the metal lines which makes these resistant to adhesion loss and also improve the conductivity.

Table 5 shows further examples of the novel compositions for the thicker film over 50 microns.

TABLE 5

Thicker photoresist with undercut profile.

| Component type | Component name | Examples 28 Wt. % | 29 Wt. % | 30 Wt. % | 31 Wt. % | 32 Wt. % | 33 Wt. % | 34 Wt. % |
|---|---|---|---|---|---|---|---|---|
| Dissolution Promotor | Additive Synthesize Example 1 | 4.85 | | | | | | |
| | Additive Synthesize Example 2 | | 4.85 | | | | | |

TABLE 5-continued

Thicker photoresist with undercut profile.

| | | Examples | | | | | | |
|---|---|---|---|---|---|---|---|---|
| Component type | Component name | 28 Wt. % | 29 Wt. % | 30 Wt. % | 31 Wt. % | 32 Wt. % | 33 Wt. % | 34 Wt. % |
| | Additive Synthesize Example 3 | | 4.85 | | | | | |
| | Additive Synthesize Example 4 | | | 4.85 | | | | |
| | Additive Synthesize Example 7 | | | | 4.85 | | | |
| | TPPA | | | | | | 4.85 | |
| | B126X-SA | | | | | | | 4.85 |
| Acrylic polymer | Acrylic polymer synthesis example 9 | 19.4 | 19.4 | 19.4 | 19.4 | 19.4 | 19.4 | 19.4 |
| Novolak | Novolak-3 | 24.22 | 24.22 | 24.22 | 24.22 | 24.22 | 24.22 | 24.22 |
| PAG | NIT PAG | 0.36 | 0.36 | 0.36 | 0.36 | 0.36 | 0.36 | 0.36 |
| Additive 1 | MTA | 0.02 | 0.02 | 0.02 | 0.02 | 0.02 | 0.02 | 0.02 |
| Additive 2 | MP Triazine | 0.08 | 0.08 | 0.08 | 0.08 | 0.08 | 0.08 | 0.08 |
| Surfactant | APS437 | 0.07 | 0.07 | 0.07 | 0.07 | 0.07 | 0.07 | 0.07 |
| Solvent | PGMEA | 31.6 | 31.6 | 31.6 | 31.6 | 31.6 | 31.6 | 31.6 |
| | 3MBA* | 19.4 | 19.4 | 19.4 | 19.4 | 19.4 | 19.4 | 19.4 |
| | Total Wt. | 100 | 100 | 100 | 100 | 100 | 100 | 100 |

*3-methoxybutyl acetate

Coating: Formulation 28-34 were tested on 8" diameter Si and Cu wafers. The Si wafers were dehydration baked and vapor primed with hexamethyldisilazane (HMDS). The Cu wafers were silicon wafers coated with 5,000 Angstroms of silicon dioxide, 250 Angstroms of tantalum nitride, and 3,500 Angstroms of Cu (PVD electroplated).

The resist coatings were prepared by spin coating the resist samples and applying a soft bake for 300 seconds at 130° C. on standard wafer track hot plate in contact mode. The spin speed was adjusted to obtain 50-microns thick resist films. The film thickness measurement was conducted on Si wafers using optical measurements.

Imaging: The wafers were exposed on SUSS MA200 CC Mask Aligner. The resist was post exposure baked at 100° C. for 100 seconds and puddle developed for 240 seconds in AZ® 300 MIF Developer (0.26N aqueous solution of tetramethyl ammonium hydroxide=TMAH) at 23° C. The developed resist images were inspected using Hitachi S4700 or AMRAY 4200L electron microscopes.

The undercut size was measured by the enlarged SEM image. Formulations 28-32 show the undercut from 2.1 to 2.5 micron in exposure dosage range 500-1000 mJ/cm². As comparison, Formulation 33 and 34 did not show undercut. TPPA and B126X-SA is not efficient to generate undercut in this formulation.

What is claimed is:

1. A positive working photosensitive composition comprising:
   a) at least one photoacid generator wherein said photoacid generator ranges from about 0.1 wt % to about 6 wt % as part of the total mass of solid components;
   b) at least one Novolak polymer;
   c) at least one acrylate polymer, comprising a component having structure (I),

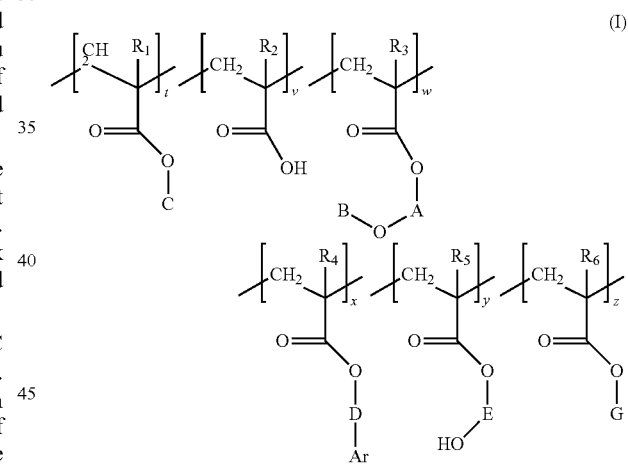

wherein $R_1$ to $R_6$ are, independently, —H, or —$CH_3$, A is a linear or branched $C_2$ to $C_{10}$ alkylene group, B is a $C_1$ to $C_{12}$ primary or secondary unsubstituted linear, branched, cyclic or alicyclic alkyl group, C is a $C_1$ to $C_{12}$ primary or secondary unsubstituted linear, branched, cyclic or alicyclic alkyl group, D is a linking group that is a direct valence bond, or a linear or branched $C_1$ to $C_{10}$ alkylene group, Ar is a substituted or unsubstituted aromatic group or heteroaromatic group, E is a linear or branched $C_2$ to $C_{10}$ alkylene group, G is an acid cleavable group, t is 0 mole % to about 40 mole %, v is 0 mole % to about 15 mole %, w is 0 mole % to about 45 mole %, x is 0 mole % to about 80 mole %, y is about 20 mole % to about 50 mole % and z is about 20 mole % to about 50 mole %, and further wherein the sum of t, v, w, x, y and z equals 100 mole %;

d) at least one glycidyl hydroxy benzoic acid condensate material comprising one or more compounds having structure (II),

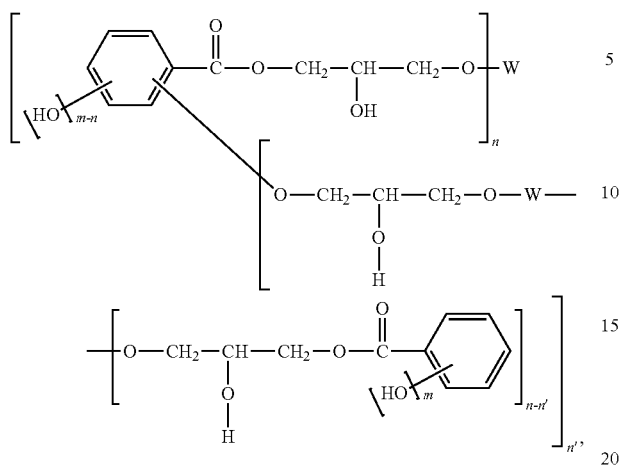

wherein,
W is an organic moiety having a molecular weight of 600 or less, wherein W forms an ether bond with the oxygen to which it is bound,
m is an integer from 1 to 3 and
n is an integer from 1 to 4, and further provided that when m is 1, n is 3 or 4,
and when m is 2 or 3, n is an integer from 1 to 4,
n' is 0 or 1, where further said component d) ranges from about 1 wt % to about 30 wt % of total solid components a) b), c), d) and e),
e) at least one heterocyclic thiol compound comprising a ring structure chosen from the general structures (III), (IIIa) or (IIIb), or tautomers thereof; and

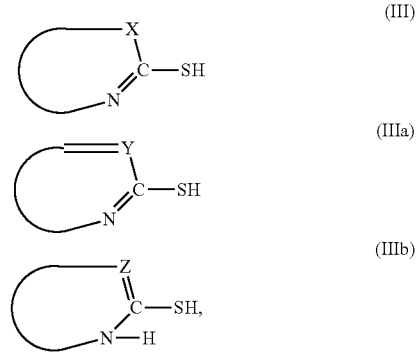

wherein,
said ring structure is a single ring structure having from 4 to 8 atoms, or a multi ring structure having from 5 to 20 atoms; and wherein the single ring structure, or the multi ring structure comprises an aromatic, non-aromatic, or heteroaromatic ring, and in said structure (III), X is selected from the group consisting of $C(Rt_1)$ $(Rt_2)$, O, S, Se, and Te;

in said structure (IIIa), Y is selected from the group consisting of $C(Rt_3)$ and N;

in said structure (IIIb), Z is selected from the group consisting of $C(Rt_3)$ and N; and $Rt_1$, $Rt_2$, and $Rt_3$ are independently selected from the group consisting of H, a substituted alkyl group having 1 to 8 carbon atoms, an unsubstituted alkyl group having 1 to 8 carbon atoms, a substituted alkenyl group having 2 to 8 carbon atoms, unsubstituted alkenyl group having 2 to 8 carbon atoms, a substituted alkynyl group having 2 to 8 carbon atoms, unsubstituted alkynyl group having 2 to 8 carbon atoms, a substituted aromatic group having 6 to 20 carbon atoms, a substituted heteroaromatic group having 3 to 20 carbon atoms, unsubstituted aromatic group having 6 to 20 carbon atoms and unsubstituted heteroaromatic group having 3 to 20 carbon atoms;

f) at least one solvent, and said composition does not contain any diazonaphthoquinone sulfonates.

2. The positive working photosensitive composition of claim 1, wherein said glycidyl hydroxy benzoic acid condensate material having structure (II) is one wherein the moiety W is an aliphatic moiety selected from the group consisting of an aliphatic hydrocarbon, an aliphatic alkyl ether, a bis(alkyl)sulfone, and a bis(alkyl) ketone.

3. The positive working photosensitive composition of claim 1, wherein glycidyl hydroxy benzoic acid condensate material having structure (II) is one wherein the moiety W is an aromatic moiety selected from an arene, a polycyclic arene, a bis(aryl) ether, a biphenyl, a bis(aryl)sulfone, bis(phenyl)alkylene, an (alkyl)(aryl)ketone, a bis(aryl)ketone, a bis(aryl)sulfone, and an (alkyl)(aryl)sulfone.

4. The positive working photosensitive composition of claim 1, wherein said glycidyl hydroxy benzoic acid condensate material comprises at least one compound having structure (IVa-1), wherein n is 3 to 4, and Rw is OH or the moiety (IVb-1), wherein ∿ represents the point of attachment in this moiety;

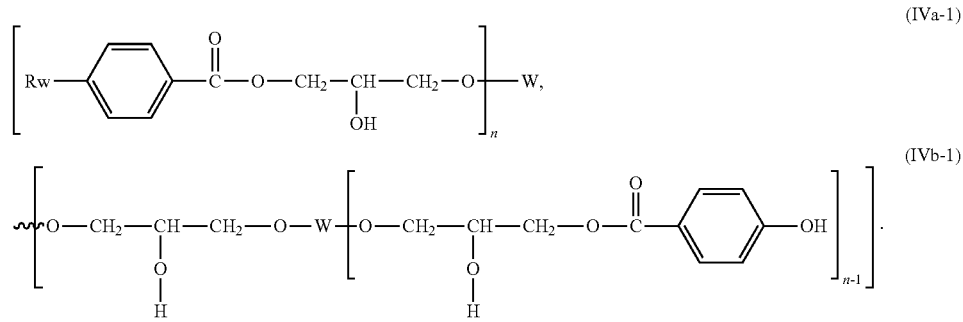

5. The positive working photosensitive composition of claim 1, wherein said glycidyl hydroxy benzoic acid condensate material comprises at least one compound having structure (IVa-2), wherein n is 1 to 4, and Rw1 is OH or the moiety (IVb-2), wherein 〰 represents the point of attachment in this moiety;

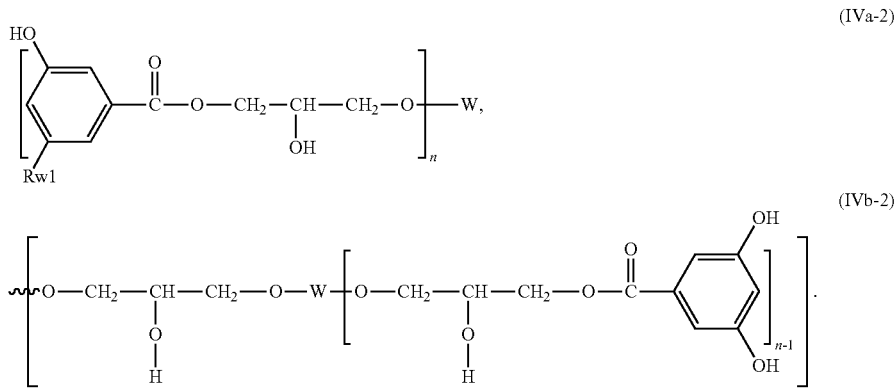

(IVa-2)

(IVb-2)

6. The positive working photosensitive composition of claim 1, wherein said glycidyl hydroxy benzoic acid condensate material comprises at least one compound having structure (IVa-3), wherein n is 1 to 4, and Rw2 is OH or the moiety (IVa), provided that no more than one Rw2 is the moiety (IVb-3), wherein 〰 represents the point of attachment in this moiety;

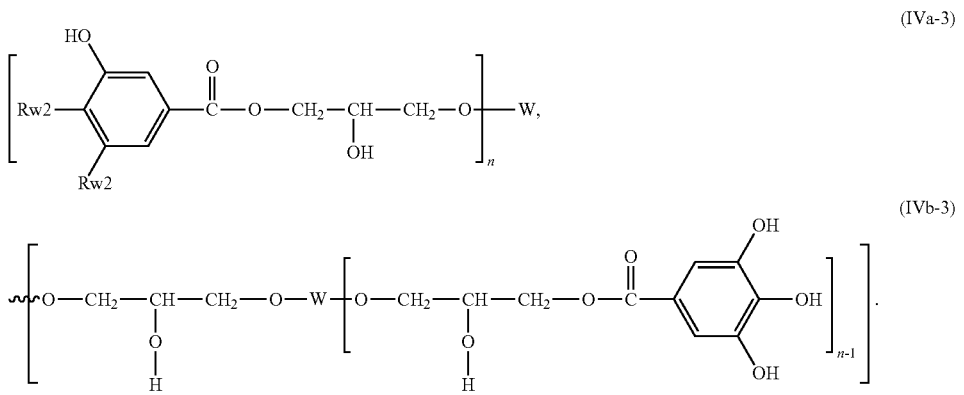

(IVa-3)

(IVb-3)

7. The positive working photosensitive composition of claim 1, wherein said organic moiety W is selected from the group consisting of moieties of structures (Wa), (Wb), (Wc), (Wd), (We) and (Wf); wherein 〰 represents an attachment point within each of these organic moieties, where it forms an ether bond with the oxygen in said glycidyl hydroxy benzoic acid condensate material of structure (II);

Xa is a moiety selected from the group consisting of a direct valence bond, alkylene, —SO$_2$—, —C(=O)— and —O—;

Ra1, Rb1 and Rc are independently selected from a $C_1$ to $C_5$ alkyl or $C_2$ to $C_5$ alkyleneoxyalkyl;

Ra2 is selected from a $C_1$ to $C_5$ alkyl an $C_2$ to $C_5$ alkyleneoxyalkyl, a $C_1$ to $C_5$ alkyloxy, a halide, a $C_1$ to $C_5$ alkylsulfonyl a $C_1$ to $C_5$ alkylcarbonyl, and a $C_1$ to $C_5$ alkylcarbonyloxy, and n" ranges from 0 to 12;

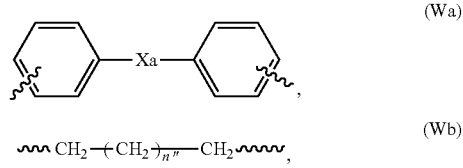

(Wa)

(Wb)

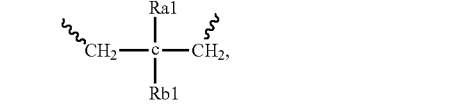

(Wc)

-continued (Wd) 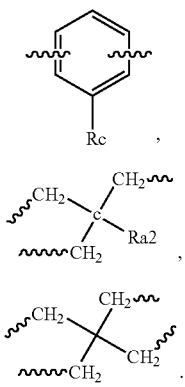

(We), (Wf) 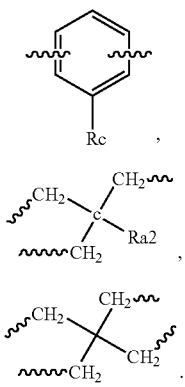

8. The positive working photosensitive composition of claim 1, wherein said glycidyl hydroxy benzoic acid condensate material comprises at least one compound having structure (Va-1), wherein Rw3 is OH, or a moiety of structure (Vb-1), wherein ⌇ represents the point of attachment in this moiety, provided m is 2 to 3, n' is 1 or 0; and Xa is selected from the group consisting of a direct valence bond, alkylene, —$SO_2$—, —C(=O)— and —O—;

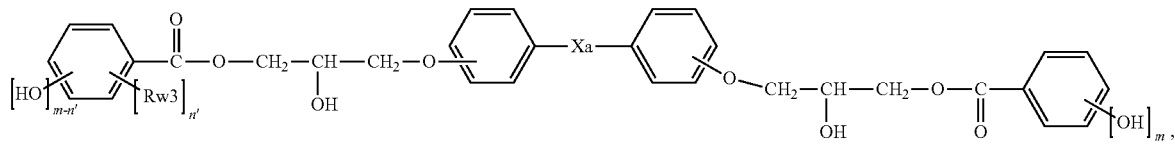

(Va-1)

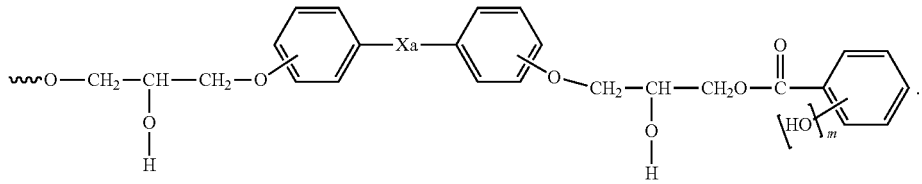

(Vb-1)

9. The positive working photosensitive composition of claim 1, wherein said glycidyl hydroxy benzoic acid condensate material comprises at least one compound having structure (VIa-1), wherein Rw20 is OH, or a moiety of structure (VIb-1), wherein ⌇ represents the point of attachment in this moiety, provided that m is 2 to 3, n' is 0 or 1, and further wherein, Ra1 and Rb1 are independently selected from a $C_1$ to $C_5$ alkyl or a $C_2$ to $C_5$-alkylene-O-alkyl moiety,

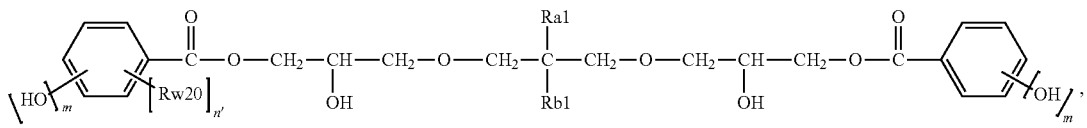

(VIa-1)

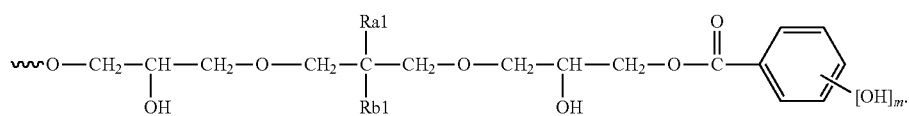

(VIb-1)

10. The positive working photosensitive composition of claim 1, wherein said glycidyl hydroxy benzoic acid condensate material comprises at least one compound of structure (VIIa-1), wherein Rw23 is OH, or a moiety of structure (VIIb-1), wherein ∿ represents the point of attachment in this moiety, provided m is 1, 2 or 3, and n' is 0 or 1, and further wherein,
Ra2 is selected from a $C_1$ to $C_5$ alkyl or a $C_2$ to $C_5$-alkylene-O-alkyl moiety;

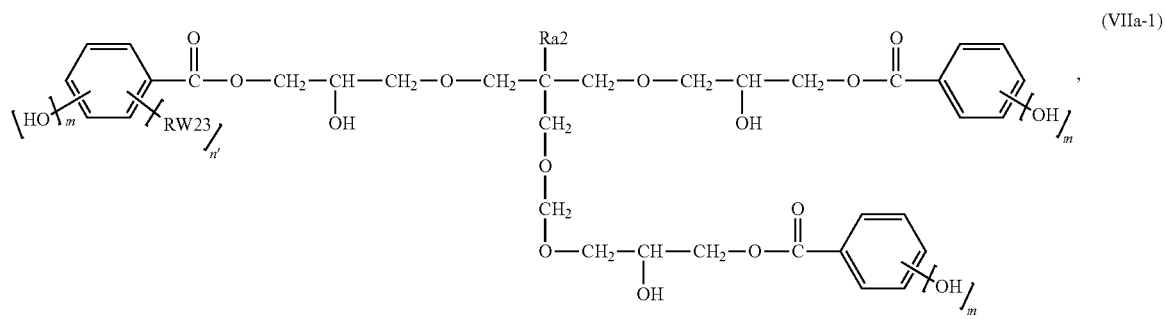

(VIIa-1)

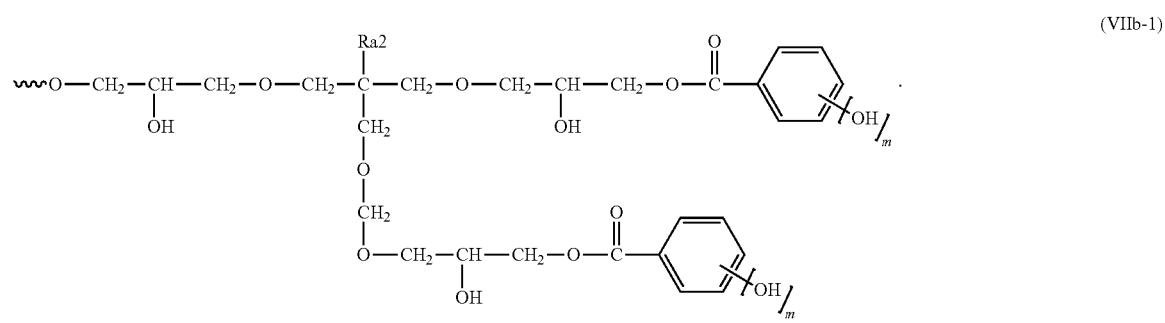

(VIIb-1)

11. The positive working photosensitive composition of claim 1, wherein said glycidyl hydroxy benzoic acid condensate material comprises at least one compound of structure (VIIa-2), wherein Rw24 is OH or the moiety (VIIb-2), wherein ∿ represents the point of attachment in this moiety, provided that no more than one Rw24 is the moiety (VIIb-2), and further wherein, Ra2 is a $C_1$ to $C_5$ alkyl or a $C_2$ to $C_5$-alkylene-O-alkyl moiety,

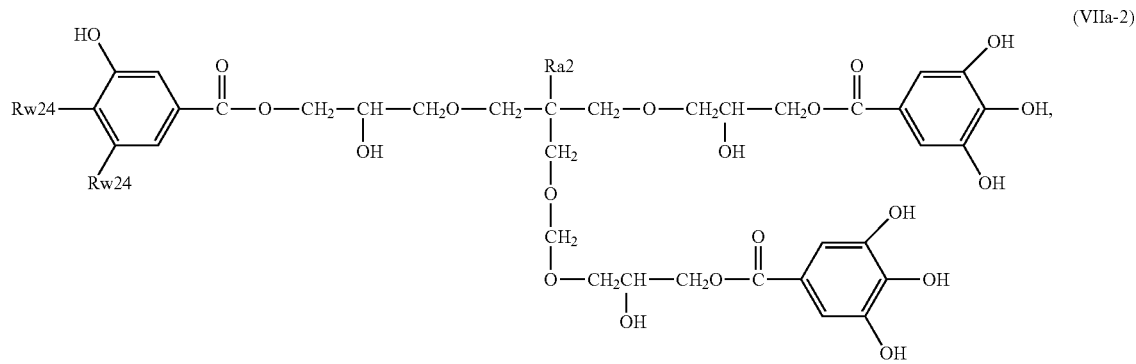

(VIIa-2)

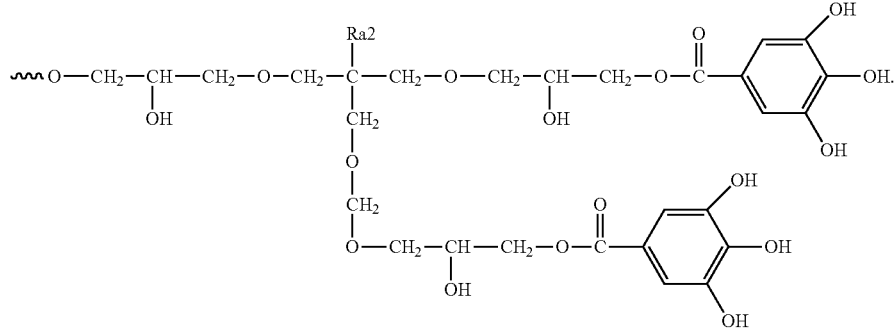
(VIIb-2)

12. The positive working photosensitive composition of claim 1, wherein said glycidyl hydroxy benzoic acid condensate material comprises at least one compound of structure (VIIa-3), wherein Rw25 is OH or the moiety (VIIb-3), wherein ∿ represents the point of attachment in this moiety, provided that no more than one Rw25 is the moiety (VIIb-3), and further wherein, Ra2 is a $C_1$ to $C_5$ alkyl or a $C_2$ to $C_5$-alkylene-O-alkyl moiety,

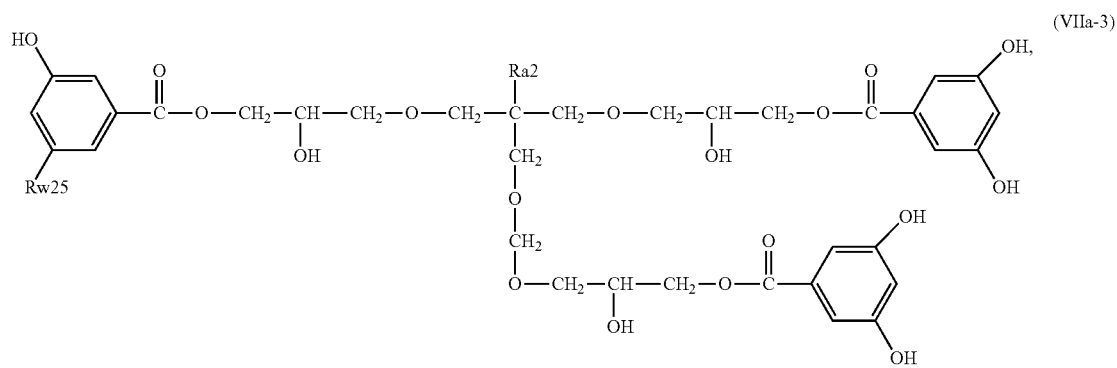
(VIIa-3)

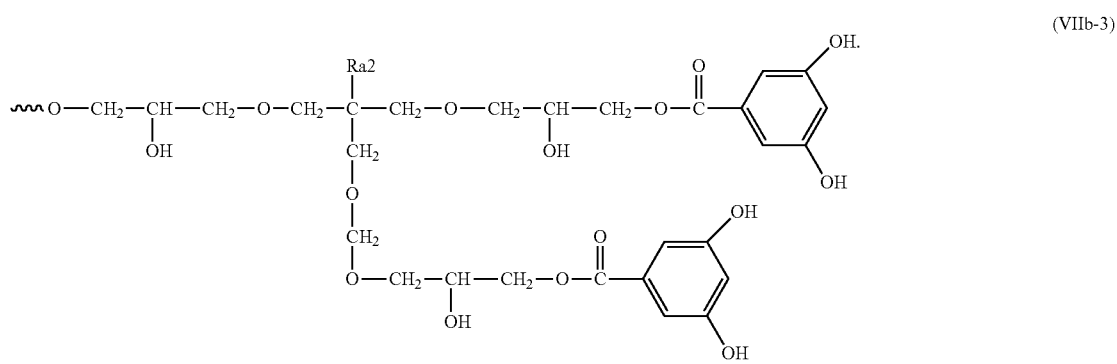
(VIIb-3)

13. The positive working photosensitive composition of claim 1, wherein said glycidyl hydroxy benzoic acid condensate material comprises at least one compound of structure (VIIa-4), wherein Rw26 is OH or the moiety (VIIb-4), wherein ∿ represents the point of attachment in this moiety, provided that no more than one Rw26 is the moiety (VIIb-4), and further wherein, Ra2 is a $C_1$ to $C_5$ alkyl or a $C_2$ to $C_5$-alkylene-O-alkyl moiety,

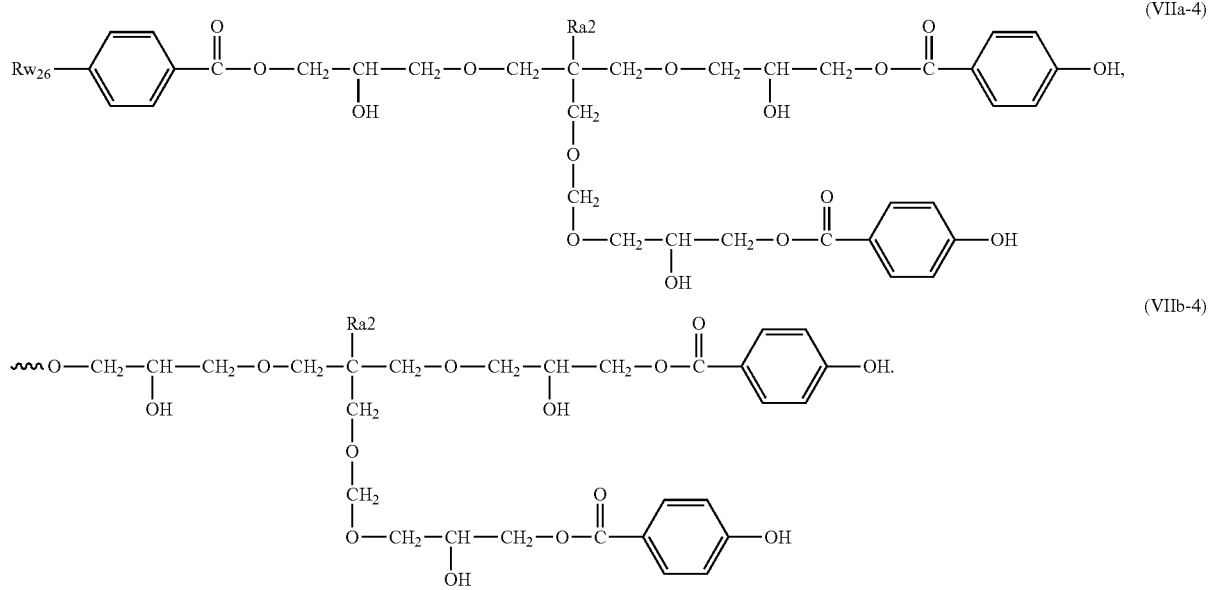

14. The composition of claim 1 where further said component d) ranges from about 3 wt % to about 20 wt % of total solid components a) b), c), d) and e).

15. The composition of claim 1 where further said component d) ranges from about 5 wt % to about 15 wt % of total solid components a) b), c), d) and e).

16. A method of forming a positive relief image comprising:
 a) forming a photosensitive layer by applying the positive working photosensitive composition of claim 1, to a substrate, thus forming a film and then baking the film;
 b) image-wise exposing the photosensitive layer to actinic radiation to form a latent image;
 c) developing the latent image in a developer.

17. A method of forming a positive relief image comprising:
 a') forming a photosensitive layer by applying the positive working photosensitive composition of claim 1, to a substrate thus forming a film and then baking the film;
 b') image-wise exposing the photosensitive layer to actinic radiation to form a latent image;
 c') thermally treating the image-wise exposed photosensitive layer forming a baked latent image;
 d') developing the baked latent image in a developer.

18. A method of forming a metal pattern on a substrate comprising:
 a") forming a photosensitive layer by applying the positive working photosensitive composition of claim 1, to a substrate thus forming a film, and then baking the film;
 b") image-wise exposing the photosensitive layer to actinic radiation to form a latent image;
 c") developing the latent image in a developer to form a resist pattern on the substrate;
 d") selectively electroplating on the substrate using the resist pattern as a barrier
 e") stripping the resist pattern leaving behind the selectively electroplated metal, thereby creating a metal pattern on the substrate.

19. A method of forming a metal pattern on a substrate comprising:
 a''') forming a photosensitive layer by applying the positive working photosensitive composition of claim 1, to a substrate thus forming a film and then baking the film;
 b''') image-wise exposing the photosensitive layer to actinic radiation to form a latent image;
 c''') thermally treating the image-wise exposed photosensitive layer forming a baked latent image;
 d''') developing the baked latent image in a developer to form a resist pattern on the substrate;
 e''') selectively electroplating on the substrate using the resist pattern as a barrier
 f''') stripping the resist pattern leaving behind the selectively electroplated metal, thereby creating a metal pattern on the substrate.

* * * * *